(12) United States Patent
Dinarello et al.

(10) Patent No.: US 9,457,070 B2
(45) Date of Patent: *Oct. 4, 2016

(54) COMPOSITIONS, METHODS AND USES OF ALPHA 1-ANTITRYPSIN FOR EARLY INTERVENTION IN BONE MARROW TRANSPLANTATION AND TREATMENT OF GRAFT VERSUS HOST DISEASE

(75) Inventors: Charles A. Dinarello, Boulder, CO (US); Eli C. Lewis, Be'er Sheva (IL)

(73) Assignee: THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 404 days.

This patent is subject to a terminal disclaimer.

(21) Appl. No.: 13/209,349

(22) Filed: Aug. 12, 2011

(65) Prior Publication Data

US 2012/0045449 A1 Feb. 23, 2012

Related U.S. Application Data

(63) Continuation-in-part of application No. 11/916,521, filed as application No. PCT/US2006/022436 on Jun. 7, 2006, now abandoned.

(60) Provisional application No. 60/687,850, filed on Jun. 7, 2005.

(51) Int. Cl.
| | |
|---|---|
| *A61K 38/57* | (2006.01) |
| *A61K 31/60* | (2006.01) |
| *A61K 38/12* | (2006.01) |
| *A61K 38/17* | (2006.01) |
| *C12Q 1/37* | (2006.01) |
| *C07K 7/64* | (2006.01) |

(52) U.S. Cl.
CPC ............... *A61K 38/57* (2013.01); *C12Q 1/37* (2013.01); *A61K 31/60* (2013.01); *A61K 38/12* (2013.01); *A61K 38/179* (2013.01); *G01N 2333/81* (2013.01); *G01N 2333/96433* (2013.01); *G01N 2800/245* (2013.01)

(58) Field of Classification Search
None
See application file for complete search history.

(56) References Cited

U.S. PATENT DOCUMENTS

| | | | |
|---|---|---|---|
| 6,022,855 | A | 2/2000 | Thomas et al. |
| 6,127,145 | A | 10/2000 | Sutliff et al. |
| 6,645,934 | B1 | 11/2003 | Rodemann et al. |
| 6,924,267 | B2 * | 8/2005 | Daemen et al. ............ 514/14.9 |
| 7,034,033 | B2 | 4/2006 | Boyce et al. |
| 7,304,033 | B2 | 12/2007 | Larsen et al. |
| 7,790,685 | B2 | 9/2010 | Kiss |
| 2003/0053998 | A1 | 3/2003 | Daemen et al. |
| 2003/0105027 | A1 | 6/2003 | Rosenbloom |
| 2004/0220242 | A1 | 11/2004 | Shapiro |
| 2005/0074848 | A1 * | 4/2005 | Schwabe ............ 435/69.1 |
| 2009/0118162 | A1 | 5/2009 | Shapiro et al. |
| 2009/0203580 | A1 | 8/2009 | Dinarello et al. |
| 2009/0214467 | A1 | 8/2009 | Shakhov et al. |
| 2009/0220518 | A1 | 9/2009 | Dinarello et al. |
| 2009/0289182 | A1 | 11/2009 | Pevsner |
| 2010/0087436 | A1 | 4/2010 | Bardwell et al. |
| 2012/0045449 | A1 | 2/2012 | Dinarello et al. |

FOREIGN PATENT DOCUMENTS

| | | |
|---|---|---|
| EP | 0511188 B1 | 6/1997 |
| WO | WO0051624 A2 | 9/2000 |
| WO | WO02053092 A2 | 7/2002 |
| WO | 2006133403 A2 | 12/2006 |
| WO | 2010088415 A2 | 8/2010 |

OTHER PUBLICATIONS

Korngold et al (Biol. Bld. Marrow Transpl., 2003, 9: 292-303).*
Janciauskiene (Biochem. Biophys. Res. Comm., 2004, 321: 592-600).*
Yamane et al (abstract of Leuk Lymphoma, 2003, 44(12): 2095-2097).*
Hill et al (JCI, 1999, 104: 459-467).*
Zeiser (Hematology Education: the education program for the annual congress of the European Hematology Association, 2014, 8(1): 359-365).*
Soucie and Blazar (Blood, 2009 114: 4327-4336).*
Barrett and Melenhorst (world wide web at moleculartherapy.org 19(2): 2011.*
OmniBio (Dec. 9, 2014, world wideweb at omnibiopharma.com).*
OmniBio (2014, Interim Phase 1/2 Data presented at the American Society of Hematology).*
Marcondes et al (2014, 56th ASH Annual Meeting and Exposition, San Francisco, CA, oral and poster abstracts, abstract 3927).*
Kamada (2016, kamada.com/news_item.php?ID=217).*
Marcondes et al (2014, 56th ASH Annual Meeting and Exposition, San Francisco, CA, poster presentation).*
BioSpace, 2014, worldwideweb at biospace.com/News/omni-biopharmaceutical-announces-encouraging/357849.*

(Continued)

*Primary Examiner* — Michael Szperka
*Assistant Examiner* — Marianne Dibrino
(74) *Attorney, Agent, or Firm* — Faegre Baker Daniels LLP

(57) ABSTRACT

Embodiments of the present invention relate to compositions and methods for treatment of subjects in need of or having a bone marrow transplant. Certain embodiments describe compositions and methods for treatment of conditions associated with bone marrow transplantations in a subject, for example, Graft versus Host Disease (GvHD) or bone marrow transplantation rejection. Some embodiments concern early or immediate bone marrow transplantation rejection. Certain embodiments relate to compositions and uses of alpha1-antitrypsin (α1-antitrypsin, AAT) and carboxyterminal peptide derivatives thereof and/or compositions and uses of serine protease inhibitors, immunomodulators or anti-inflammatory agent activity similar to that of AAT.

5 Claims, 25 Drawing Sheets

(56) References Cited

OTHER PUBLICATIONS

Brantly, et al. Phase I trial of intramuscular injection of a recombinant adena-associated virus serotype 2 alpha1-antitrypsin (AAT) vector in AAT-deficient adults. Hum Gene Ther. 2006, 17(12):1177-1186; Abstract.
Flotte, et al. Phase I trial of intramuscular injection of a recombinant adena-associated virus 1-antitrypsin (rAAV2-Cb-hAAT) gene vector to AAT-deficient adults. Hum. Gene Ther. 2004, 15(1):93-128;.
Hagen, et al. High alpha-1 antitrypsin clearance predicts severity of gut graft-versus-host disease (GVHD) in children. Pediatr Transplant. ePub Jul. 29, 2011, 15(6):659-663.
Marcondes, et al. Inhibition of IL-32 activation by A-1 antitrypsin suppresses alloreactivity and increases survival in an allogeneic murine marrow transplantation model. Blood. ePub Sep. 6, 2011, 118(18):5031-5039.
Shahaf, et al. Alpha-1-antitrypsin gene delivery reduces inflammation, increases T-regulatory cell population'size and prevents islet allograft rejection. Mol Med. ePub Jun. 9, 2011, 17(9-10).
Tawara, et al. Alpha-1-antitrypsin monotherapy reduces graft-versus-host disease after experimental allogeneic bone marrow transplantation. Proc Natl Acad Sci USA ePub Dec. 27, 2011, 109(2):564-569.
Vanhove, et al. Selective blockade of CD28 and not CTLA-4 with a single-chain Fv-alpha1- antitrypsin fusion antibody. Blood 2003, 102(2):564-570.
Couriel et al. A Phase III Study of Infliximab and Corticosteroids Fo the Initial Treatment of Acute Graft-Versus-Disease; Biol Blood Marrow Transplant, Dec. 2009, 15(12): pp. 1555-1562.
Hamadani et al. Addition of Infliximab to Standard Acute Graft-Versus- Host Disease Prophylaxis Following Allogeneic Peripheral Blood Cell Transplantation; Biol Blood Marrow Transplant, Jul. 2008; 14(7): pp, 783-789.
Anonymous, "Graft-Versus-Host-Disease Clinical Trials", Dana-Farber Cancer Institute, May 2011, dana-farber.org/Research/Chnical-Trials-by-Diagnosis.aspx?did=31, 4 pages.
Extended European Search Report issued in 12823623.9, PCT/US2012/050420, mailed Mar. 3, 2015, 9 pages.
Marcondes, Mario et al., Database Biosis, Biosciences Information Services, Nov. 2010, vol. 116 No. 21, 4 pages.
Andus et al, Suspected cases of severe side effects after infliximab (Remicade) in Germany. Med Klin (Munich) Aug. 15, 2003; 98(8):429-36. (Abstract Only).
Arora, Prince K. et al. "Alpha-1 Antitrypsin is an Effector of Immunological Stasis." Nature 274:589-590, Aug. 10, 1978.
Baecher-Allan, Clare, Human regulatory T cells and their role in autoimmune disease. Immunological Reviews, vol. 212, Issue 1, pp. 203-216.
Bell, J. Jeremiah, et al., In Trans T Cell Tolerance Diminishes Autoantibody Responses and Exacerbates Experimental Allergic Encephalomyelitis, The Journal of Immunology, (2008) pp. 1508-1516.
Camussi, Giovanni et al. Synthesis and Release of Platelet-Activating Factor is Inhibited by Plasma Alpha 1-Proteinase Inhibitor or Alpha 1-Antichymotrypsin and is Stimulated by Proteinases. J. Exp. Med. 168:1293-1306, Oct. 1988.
Churg, Andrew et al. Alpha-1-Antitrypsin and a Broad Spectrum Metalloprotease Inhibitor, RS113456, Have Similar Acute Anti-Inflammatory Effects. Laboratory Investigation, vol. 81, No. 8. (Aug. 2001), pp. 1119-1131.
Dong, VM, et al., Transplantation tolerance: The concept and its applicability; The Pediatric Transplantation, 3, (1999), pp. 181-192.

Ellerin et al, Review "Infections and Anti-Tumor Necrosis Factor •Therapy" Arthritis & Rheumatism vol. 48, No. 11 Nov. 2003, pp. 3013-3022.
Goodnow, Christopher C. Pathways for self-tolerance and the treatment of autoimmune diseases. The Lancet, vol. 357 (Jun. 30, 2001), pp. 2115-2121.
Hill et al (JCI, 1999, 104:459-467).
International Search Report and Written Opinion of the International Searching Authority, PCT/US08/60848, Dec. 22, 2008.
Keane et al, "Tuberculosis Associated with Infliximab, a Tumor Necrosis Factor •-NeutralizinAgent," New Engl. J. Med., vol. 345, No. 15 Oct. 11, 2001.
Kirani, K.R.L., Co-Existence of Pulmonary Tuberculosis and Diabetes Mellitus: Some Observations. Department of Microbiology, Rangaraya Medical College, Kakinada, Lakshi Mansion, Plot No. 164, 3-16-2, Shanti Nagar, Kakinada 533 003; Ind J Tub,vol. 45, 1998, pp. 47-48.
Kraus, Thomas A., et al., Oral tolerance and inflammatory bowel disease. Current Opinion in Gastroenterology, vol. 21 (2005), pp. 692-696.
Libert, Claude et al. Alpha 1-Antitrypsin Inhibits the Lethal Response to TNF in Mice. The Journal of Immunology, 157 (11): 5126-5126, 1996.
Lieberman, J., Augmentation therapy reduces frequency of lung infections in antitrypsin deficiency: a new hypothesis with supporting data, Chest, 2000, vol. 118, No. 5, pp. 1480-1485.
Lomas, David A., et al., Preparation and Characterization of Latent alpha-1 antitrypsin. Journal of Biological Chemistry, vol. 270, No. 10, (Mar. 10, 1995) pp. 5282-5288.
Marketletter Publications Ltd. Newsletter (Sep. 13, 1999), 2 pages.
Molloy et al "Morbidity and mortality in rheumatoid patients during treatment with adalimumab and infliximab," Rheumatology (2004) 43 (4) 522-523.
O'Riordan, K., et al., Alpha 1—antitrypsin deficiency-associated panniculitis. Transplantation, vol. 63, No. 3 (Feb. 15, 1997), pp. 480-482.
Panasyuk, A.V., et al., Disseminated Pulmonary Tuberculosis, Sugar Diabetes, and Amyloidosis in a Patient with Hereditary alpha 1-antitrypsin deficiency. Probl. Tuberk., No. 1, (1988), pp. 72-74.
PCT Publication issued in WO 2006/133403, mailed Dec. 14, 2006, 1 page.
Pozzilli, P., et al., No effect of oral insulin on residual beta-cell function in recent-onset Type I diabetes (the IMDIAB VII). Diabetologia (2000) 43, pp. 1004-1004.
Rothe, Helga, et al., IL-18 Inhibits Diabetes Development in Nonobese Diabetic Mice by Counterregulation of Th1-Dependent Destructive Insulitis, The Journal of Immunology, 163 (1999), pp. 1230-1236.
Schroeder, Rebecca A., M.D., et al., Tolerance and the "Holy Grail" of Transplantation. Journal of Surgical Research, 111, (2003), pp. 109-119.
Siegel et al. "Safety & Efficacy Update on Approved TNF-Blocking Agents" OTRR, CBER/FDA Arthritis Advisory Committee Mar. 4, 2003, 19 pages.
Skyler, Jay S., et al. Use of Inhaled Insulin in a Basal/Bolus Insulin Regimen in Type 1 Diabetic Subjects. Diabetes Care, vol. 28, No. 7, (Jul. 2005) pp. 1630-1635.
Strom, Terry B., Saving islets from allograft rejection, vol. 102, No. 36 (Sep. 6, 2005), pp. 12651-12652.
Vidal et al "Severe neutropenia and thrombocytopenia associated with infliximab." Ann Intern. Med Aug. 5, 2003 139 (3): W-W63. (Abstract only).
Warris et al, "Invasive Pulmonary Aspergillosis Associated with Infliximab Therapy," New England Journal of Medicine, vol. 344, No. 14 Apr. 5, 2001 pp. 1099-1100.

* cited by examiner

Fig. 3C
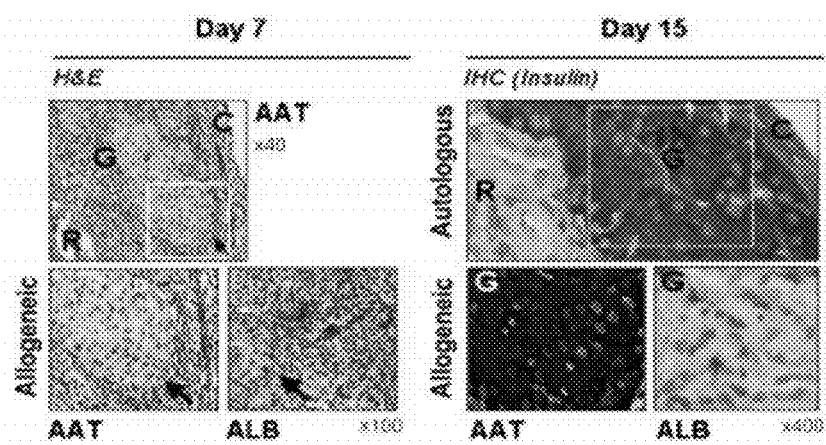
Figs. 4A-4B
A
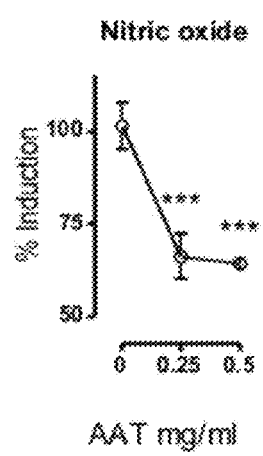
B
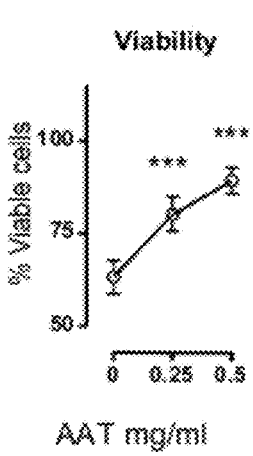

Figs. 6A-6C
A
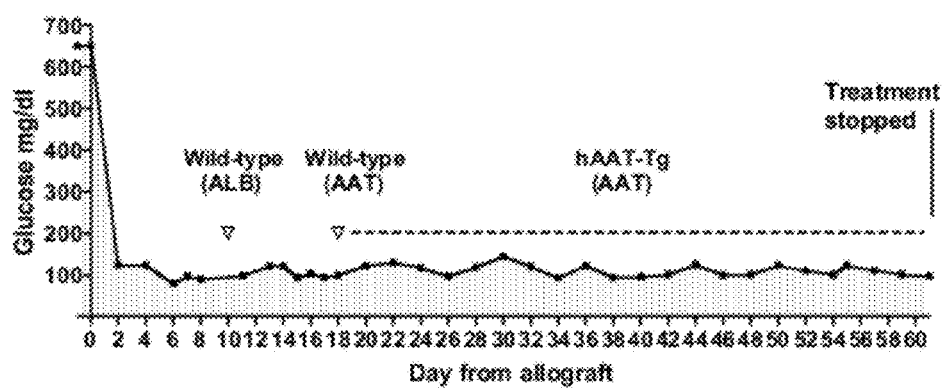
B
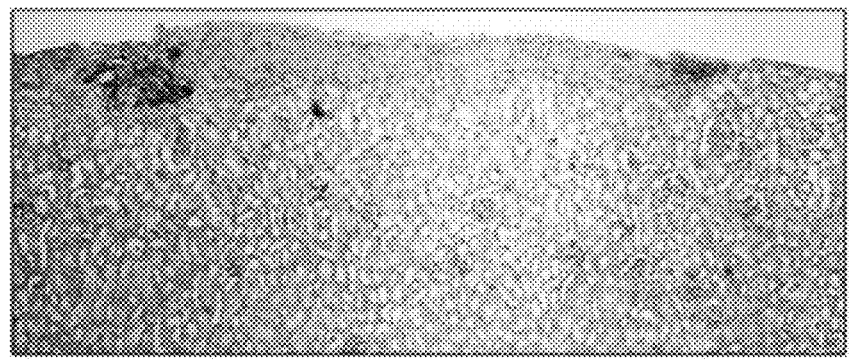
C
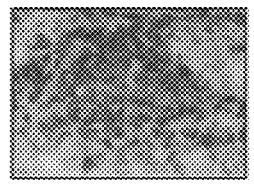
CD4
(Lymphocytes)
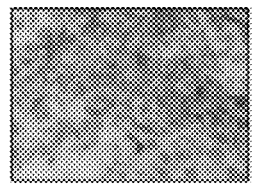
CD11b
(Monocytes/PMN)

Fig. 6D
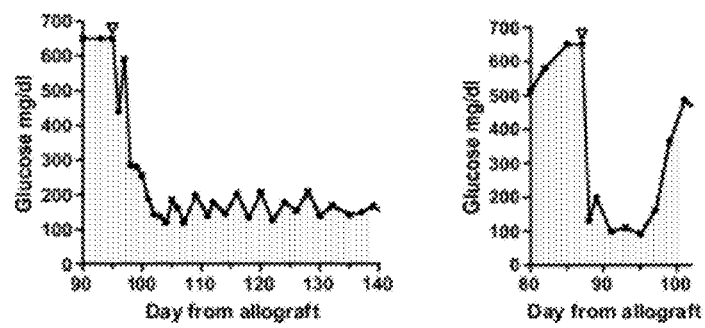
Figs. 7A-7B
A
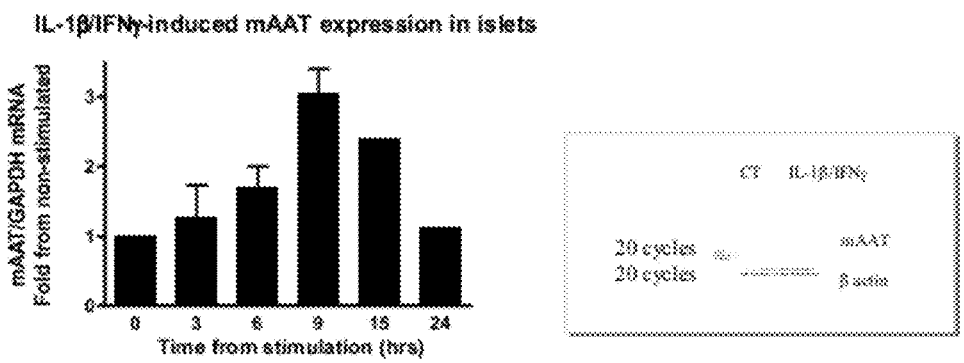
B
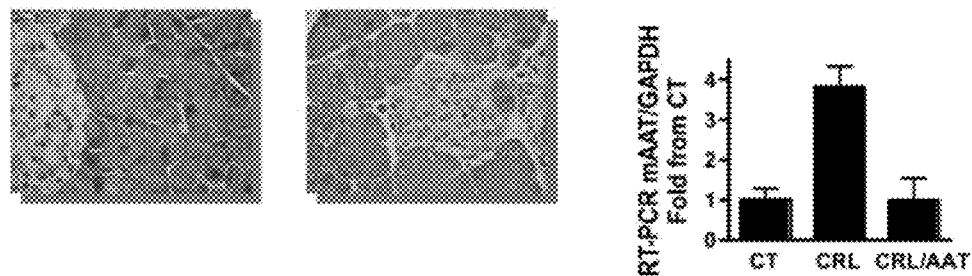

Figs. 7C-7D
C
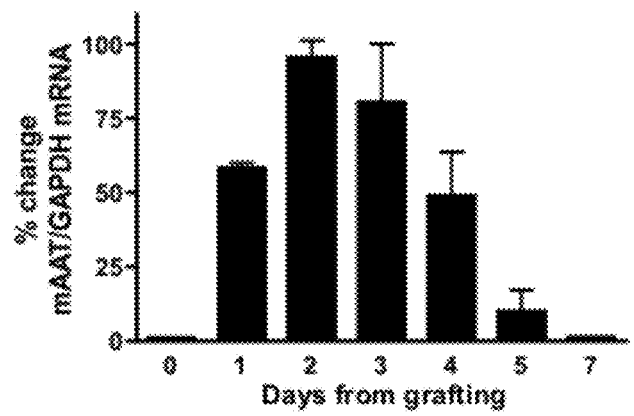
D
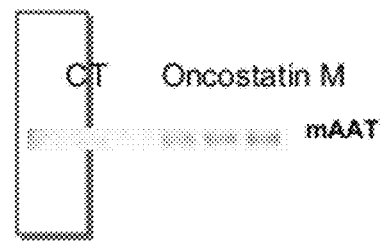
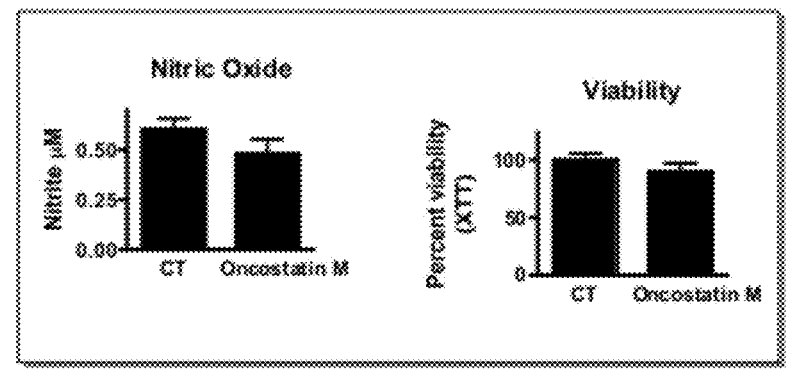

Fig. 7E
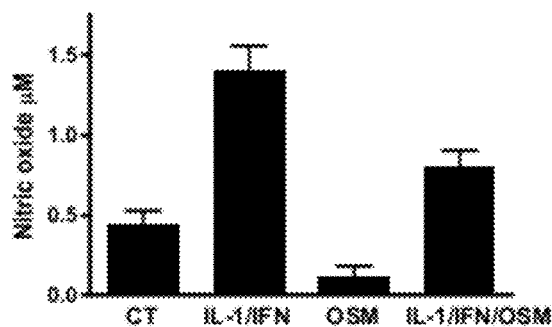
Figs. 8A-8B
A
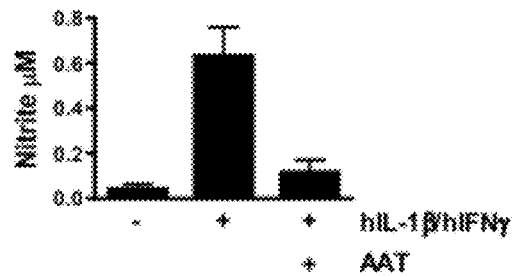
B
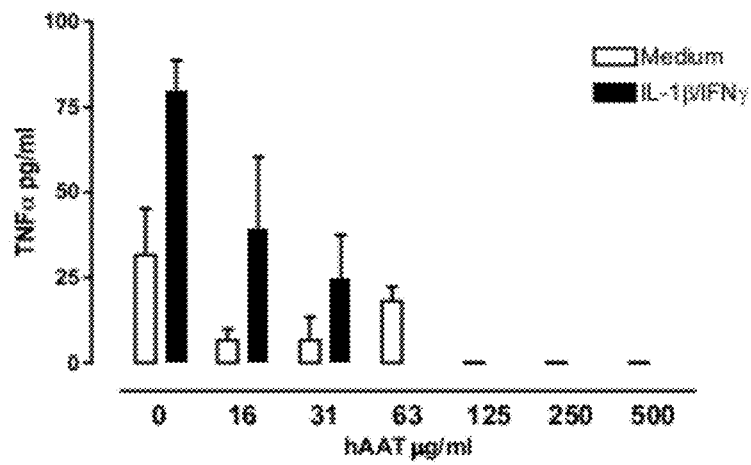

C

D

SEQUENCE LISTING

```
<160> NUMBER OF SEQ ID NOS: 63

<210> SEQ ID NO 1
<211> LENGTH: 5
<212> TYPE: PRT
<213> ORGANISM: Artificial
<220> FEATURE:
<223> OTHER INFORMATION: synthetic peptide

<400> SEQUENCE: 1

Phe Val Phe Leu Met
1               5

<210> SEQ ID NO 2
<211> LENGTH: 5
<212> TYPE: PRT
<213> ORGANISM: Artificial
<220> FEATURE:
<223> OTHER INFORMATION: synthetic peptide

<400> SEQUENCE: 2

Phe Val Phe Ala Met
1               5

<210> SEQ ID NO 3
<211> LENGTH: 5
<212> TYPE: PRT
<213> ORGANISM: Artificial
```

<220> FEATURE:
<223> OTHER INFORMATION: synthetic peptide

<400> SEQUENCE: 3

Phe Val Ala Leu Met
1               5

<210> SEQ ID NO 4
<211> LENGTH: 5
<212> TYPE: PRT
<213> ORGANISM: Artificial
<220> FEATURE:
<223> OTHER INFORMATION: synthetic peptide

<400> SEQUENCE: 4

Phe Val Phe Leu Ala
1               5

<210> SEQ ID NO 5
<211> LENGTH: 5
<212> TYPE: PRT
<213> ORGANISM: Artificial
<220> FEATURE:
<223> OTHER INFORMATION: synthetic peptide

<400> SEQUENCE: 5

Phe Leu Val Phe Ile
1               5

<210> SEQ ID NO 6
<211> LENGTH: 5
<212> TYPE: PRT
<213> ORGANISM: Artificial
<220> FEATURE:
<223> OTHER INFORMATION: synthetic peptide

<400> SEQUENCE: 6

Phe Leu Met Ile Ile
1               5

<210> SEQ ID NO 7
<211> LENGTH: 5
<212> TYPE: PRT
<213> ORGANISM: Artificial
<220> FEATURE:
<223> OTHER INFORMATION: synthetic peptide

<400> SEQUENCE: 7

Phe Leu Phe Val Leu
1               5

<210> SEQ ID NO 8
<211> LENGTH: 5
<212> TYPE: PRT
<213> ORGANISM: Artificial
<220> FEATURE:
<223> OTHER INFORMATION: synthetic peptide

<400> SEQUENCE: 8

Phe Leu Phe Val Val
1               5

<210> SEQ ID NO 9
<211> LENGTH: 5
<212> TYPE: PRT
<213> ORGANISM: Artificial

<220> FEATURE:
<223> OTHER INFORMATION: synthetic peptide

<400> SEQUENCE: 9

Phe Leu Phe Leu Ile
1               5

<210> SEQ ID NO 10
<211> LENGTH: 5
<212> TYPE: PRT
<213> ORGANISM: Artificial
<220> FEATURE:
<223> OTHER INFORMATION: synthetic peptide

<400> SEQUENCE: 10

Phe Leu Phe Phe Ile
1               5

<210> SEQ ID NO 11
<211> LENGTH: 5
<212> TYPE: PRT
<213> ORGANISM: Artificial
<220> FEATURE:
<223> OTHER INFORMATION: synthetic peptide

<400> SEQUENCE: 11

Phe Leu Met Phe Ile
1               5

<210> SEQ ID NO 12
<211> LENGTH: 5
<212> TYPE: PRT
<213> ORGANISM: Artificial
<220> FEATURE:
<223> OTHER INFORMATION: synthetic peptide

<400> SEQUENCE: 12

Phe Met Leu Leu Ile
1               5

<210> SEQ ID NO 13
<211> LENGTH: 5
<212> TYPE: PRT
<213> ORGANISM: Artificial
<220> FEATURE:
<223> OTHER INFORMATION: synthetic peptide

<400> SEQUENCE: 13

Phe Ile Ile Met Ile
1               5

<210> SEQ ID NO 14
<211> LENGTH: 5
<212> TYPE: PRT
<213> ORGANISM: Artificial
<220> FEATURE:
<223> OTHER INFORMATION: synthetic peptide

<400> SEQUENCE: 14

Phe Leu Phe Cys Ile
1               5

<210> SEQ ID NO 15
<211> LENGTH: 5
<212> TYPE: PRT
<213> ORGANISM: Artificial

```
<220> FEATURE:
<223> OTHER INFORMATION: synthetic peptide

<400> SEQUENCE: 15

Phe Leu Phe Ala Val
1               5

<210> SEQ ID NO 16
<211> LENGTH: 5
<212> TYPE: PRT
<213> ORGANISM: Artificial
<220> FEATURE:
<223> OTHER INFORMATION: synthetic peptide

<400> SEQUENCE: 16

Phe Val Tyr Leu Ile
1               5

<210> SEQ ID NO 17
<211> LENGTH: 5
<212> TYPE: PRT
<213> ORGANISM: Artificial
<220> FEATURE:
<223> OTHER INFORMATION: synthetic peptide

<400> SEQUENCE: 17

Phe Ala Phe Leu Met
1               5

<210> SEQ ID NO 18
<211> LENGTH: 5
<212> TYPE: PRT
<213> ORGANISM: Artificial
<220> FEATURE:
<223> OTHER INFORMATION: synthetic peptide

<400> SEQUENCE: 18

Ala Val Phe Leu Met
1               5

<210> SEQ ID NO 19
<211> LENGTH: 10
<212> TYPE: PRT
<213> ORGANISM: Homo sapiens

<400> SEQUENCE: 19

Met Pro Ser Ser Val Ser Trp Gly Ile Leu
1               5                   10

<210> SEQ ID NO 20
<211> LENGTH: 10
<212> TYPE: PRT
<213> ORGANISM: Homo sapiens

<400> SEQUENCE: 20

Leu Ala Gly Leu Cys Cys Leu Val Pro Val
1               5                   10

<210> SEQ ID NO 21
<211> LENGTH: 10
<212> TYPE: PRT
<213> ORGANISM: Homo sapiens

<400> SEQUENCE: 21

Ser Leu Ala Glu Asp Pro Gln Gly Asp Ala
1               5                   10
```

```
<210> SEQ ID NO 22
<211> LENGTH: 10
<212> TYPE: PRT
<213> ORGANISM: Homo sapiens

<400> SEQUENCE: 22

Ala Gln Lys Thr Asp Thr Ser His His Asp
1               5                   10

<210> SEQ ID NO 23
<211> LENGTH: 10
<212> TYPE: PRT
<213> ORGANISM: Homo sapiens

<400> SEQUENCE: 23

Gln Asp His Pro Thr Phe Asn Lys Ile Thr
1               5                   10

<210> SEQ ID NO 24
<211> LENGTH: 10
<212> TYPE: PRT
<213> ORGANISM: Homo sapiens

<400> SEQUENCE: 24

Pro Asn Leu Ala Glu Phe Ala Phe Ser Leu
1               5                   10

<210> SEQ ID NO 25
<211> LENGTH: 10
<212> TYPE: PRT
<213> ORGANISM: Homo sapiens

<400> SEQUENCE: 25

Tyr Arg Gln Leu Ala His Gln Ser Asn Ser
1               5                   10

<210> SEQ ID NO 26
<211> LENGTH: 10
<212> TYPE: PRT
<213> ORGANISM: Homo sapiens

<400> SEQUENCE: 26

Thr Asn Ile Phe Phe Ser Pro Val Ser Ile
1               5                   10

<210> SEQ ID NO 27
<211> LENGTH: 10
<212> TYPE: PRT
<213> ORGANISM: Homo sapiens

<400> SEQUENCE: 27

Ala Thr Ala Phe Ala Met Leu Ser Leu Gly
1               5                   10

<210> SEQ ID NO 28
<211> LENGTH: 10
<212> TYPE: PRT
<213> ORGANISM: Homo sapiens

<400> SEQUENCE: 28

Thr Lys Ala Asp Thr His Asp Glu Ile Leu
1               5                   10
```

```
<210> SEQ ID NO 29
<211> LENGTH: 10
<212> TYPE: PRT
<213> ORGANISM: Homo sapiens

<400> SEQUENCE: 29

Glu Gly Leu Asn Phe Asn Leu Thr Glu Ile
1               5                   10

<210> SEQ ID NO 30
<211> LENGTH: 10
<212> TYPE: PRT
<213> ORGANISM: Homo sapiens

<400> SEQUENCE: 30

Pro Glu Ala Gln Ile His Glu Gly Phe Gln
1               5                   10

<210> SEQ ID NO 31
<211> LENGTH: 10
<212> TYPE: PRT
<213> ORGANISM: Homo sapiens

<400> SEQUENCE: 31

Glu Leu Leu Arg Thr Leu Asn Gln Pro Asp
1               5                   10

<210> SEQ ID NO 32
<211> LENGTH: 10
<212> TYPE: PRT
<213> ORGANISM: Homo sapiens

<400> SEQUENCE: 32

Ser Gln Leu Gln Leu Thr Thr Gly Asn Gly
1               5                   10

<210> SEQ ID NO 33
<211> LENGTH: 10
<212> TYPE: PRT
<213> ORGANISM: Homo sapiens

<400> SEQUENCE: 33

Leu Phe Leu Ser Glu Gly Leu Lys Leu Val
1               5                   10

<210> SEQ ID NO 34
<211> LENGTH: 10
<212> TYPE: PRT
<213> ORGANISM: Homo sapiens

<400> SEQUENCE: 34

Asp Lys Phe Leu Glu Asp Val Lys Lys Leu
1               5                   10

<210> SEQ ID NO 35
<211> LENGTH: 10
<212> TYPE: PRT
<213> ORGANISM: Homo sapiens

<400> SEQUENCE: 35

Tyr His Ser Glu Ala Phe Thr Val Asn Phe
1               5                   10
```

```
<210> SEQ ID NO 36
<211> LENGTH: 10
<212> TYPE: PRT
<213> ORGANISM: Homo sapiens

<400> SEQUENCE: 36

Gly Asp His Glu Glu Ala Lys Lys Gln Ile
1               5                   10

<210> SEQ ID NO 37
<211> LENGTH: 10
<212> TYPE: PRT
<213> ORGANISM: Homo sapiens

<400> SEQUENCE: 37

Asn Asp Tyr Val Glu Lys Gly Thr Gln Gly
1               5                   10

<210> SEQ ID NO 38
<211> LENGTH: 10
<212> TYPE: PRT
<213> ORGANISM: Homo sapiens

<400> SEQUENCE: 38

Lys Ile Val Asp Leu Val Lys Glu Leu Asp
1               5                   10

<210> SEQ ID NO 39
<211> LENGTH: 10
<212> TYPE: PRT
<213> ORGANISM: Homo sapiens

<400> SEQUENCE: 39

Arg Asp Thr Val Phe Ala Leu Val Asn Tyr
1               5                   10

<210> SEQ ID NO 40
<211> LENGTH: 10
<212> TYPE: PRT
<213> ORGANISM: Homo sapiens

<400> SEQUENCE: 40

Ile Phe Phe Lys Gly Lys Trp Glu Arg Pro
1               5                   10

<210> SEQ ID NO 41
<211> LENGTH: 10
<212> TYPE: PRT
<213> ORGANISM: Homo sapiens

<400> SEQUENCE: 41

Phe Glu Val Lys Asp Thr Glu Asp Glu Asp
1               5                   10

<210> SEQ ID NO 42
<211> LENGTH: 10
<212> TYPE: PRT
<213> ORGANISM: Homo sapiens

<400> SEQUENCE: 42

Phe His Val Asp Gln Val Thr Thr Val Lys
1               5                   10
```

```
<210> SEQ ID NO 43
<211> LENGTH: 10
<212> TYPE: PRT
<213> ORGANISM: Homo sapiens

<400> SEQUENCE: 43

Val Pro Met Met Lys Arg Leu Gly Met Phe
1               5                   10

<210> SEQ ID NO 44
<211> LENGTH: 10
<212> TYPE: PRT
<213> ORGANISM: Homo sapiens

<400> SEQUENCE: 44

Asn Ile Gln His Cys Lys Lys Leu Ser Ser
1               5                   10

<210> SEQ ID NO 45
<211> LENGTH: 10
<212> TYPE: PRT
<213> ORGANISM: Homo sapiens

<400> SEQUENCE: 45

Trp Val Leu Leu Met Lys Tyr Leu Gly Asn
1               5                   10

<210> SEQ ID NO 46
<211> LENGTH: 10
<212> TYPE: PRT
<213> ORGANISM: Homo sapiens

<400> SEQUENCE: 46

Ala Thr Ala Ile Phe Phe Leu Pro Asp Glu
1               5                   10

<210> SEQ ID NO 47
<211> LENGTH: 10
<212> TYPE: PRT
<213> ORGANISM: Homo sapiens

<400> SEQUENCE: 47

Gly Lys Leu Gln His Leu Glu Asn Glu Leu
1               5                   10

<210> SEQ ID NO 48
<211> LENGTH: 10
<212> TYPE: PRT
<213> ORGANISM: Homo sapiens

<400> SEQUENCE: 48

Thr His Asp Ile Ile Thr Lys Phe Leu Glu
1               5                   10

<210> SEQ ID NO 49
<211> LENGTH: 10
<212> TYPE: PRT
<213> ORGANISM: Homo sapiens

<400> SEQUENCE: 49

Asn Glu Asp Arg Arg Ser Ala Ser Leu His
1               5                   10
```

```
<210> SEQ ID NO 50
<211> LENGTH: 10
<212> TYPE: PRT
<213> ORGANISM: Homo sapiens

<400> SEQUENCE: 50

Leu Pro Lys Leu Ser Ile Thr Gly Thr Tyr
1               5                   10

<210> SEQ ID NO 51
<211> LENGTH: 10
<212> TYPE: PRT
<213> ORGANISM: Homo sapiens

<400> SEQUENCE: 51

Asp Leu Lys Ser Val Leu Gly Gln Leu Gly
1               5                   10

<210> SEQ ID NO 52
<211> LENGTH: 10
<212> TYPE: PRT
<213> ORGANISM: Homo sapiens

<400> SEQUENCE: 52

Ile Thr Lys Val Phe Ser Asn Gly Ala Asp
1               5                   10

<210> SEQ ID NO 53
<211> LENGTH: 10
<212> TYPE: PRT
<213> ORGANISM: Homo sapiens

<400> SEQUENCE: 53

Leu Ser Gly Val Thr Glu Glu Ala Pro Leu
1               5                   10

<210> SEQ ID NO 54
<211> LENGTH: 10
<212> TYPE: PRT
<213> ORGANISM: Homo sapiens

<400> SEQUENCE: 54

Lys Leu Ser Lys Ala Val His Lys Ala Val
1               5                   10

<210> SEQ ID NO 55
<211> LENGTH: 10
<212> TYPE: PRT
<213> ORGANISM: Homo sapiens

<400> SEQUENCE: 55

Leu Thr Ile Asp Glu Lys Gly Thr Glu Ala
1               5                   10

<210> SEQ ID NO 56
<211> LENGTH: 10
<212> TYPE: PRT
<213> ORGANISM: Homo sapiens

<400> SEQUENCE: 56

Ala Gly Ala Met Phe Leu Glu Ala Ile Pro
1               5                   10
```

```
<210> SEQ ID NO 57
<211> LENGTH: 10
<212> TYPE: PRT
<213> ORGANISM: Homo sapiens

<400> SEQUENCE: 57

Met Ser Ile Pro Pro Glu Val Lys Phe Asn
1               5                   10

<210> SEQ ID NO 58
<211> LENGTH: 10
<212> TYPE: PRT
<213> ORGANISM: Homo sapiens

<400> SEQUENCE: 58

Lys Pro Phe Val Phe Leu Met Ile Glu Gln
1               5                   10

<210> SEQ ID NO 59
<211> LENGTH: 10
<212> TYPE: PRT
<213> ORGANISM: Homo sapiens

<400> SEQUENCE: 59

Asn Thr Lys Ser Pro Leu Phe Met Gly Lys
1               5                   10

<210> SEQ ID NO 60
<211> LENGTH: 7
<212> TYPE: PRT
<213> ORGANISM: Homo sapiens

<400> SEQUENCE: 60

Val Val Asn Pro Thr Gln Lys
1               5

<210> SEQ ID NO 61
<211> LENGTH: 417
<212> TYPE: PRT
<213> ORGANISM: Homo sapiens

<400> SEQUENCE: 61

Met Pro Ser Ser Val Ser Trp Gly Ile Leu Leu Ala Gly Leu Cys Cys
1               5                   10                  15

Leu Val Pro Val Ser Leu Ala Glu Asp Pro Gln Gly Asp Ala Ala Gln
                20                  25                  30

Lys Thr Asp Thr Ser His His Asp Gln Asp His Pro Thr Phe Asn Lys
            35                  40                  45

Ile Thr Pro Asn Leu Ala Glu Phe Ala Phe Ser Leu Tyr Arg Gln Leu
        50                  55                  60

Ala His Gln Ser Asn Ser Thr Asn Ile Phe Phe Ser Pro Val Ser Ile
65                  70                  75                  80

Ala Thr Ala Phe Ala Met Leu Ser Leu Gly Thr Lys Ala Asp Thr His
                85                  90                  95

Asp Glu Ile Leu Glu Gly Leu Asn Phe Asn Leu Thr Glu Ile Pro Glu
            100                 105                 110

Ala Gln Ile His Glu Gly Phe Gln Glu Leu Leu Arg Thr Leu Asn Gln
        115                 120                 125

Pro Asp Ser Gln Leu Gln Leu Thr Thr Gly Asn Gly Leu Phe Leu Ser
    130                 135                 140
```

```
Glu Gly Leu Lys Leu Val Asp Lys Phe Leu Glu Asp Val Lys Lys Leu
145                 150                 155                 160

Tyr His Ser Glu Ala Phe Thr Val Asn Phe Gly Asp His Glu Glu Ala
                165                 170                 175

Lys Lys Gln Ile Asn Asp Tyr Val Lys Gly Thr Gln Gly Lys Ile
            180                 185                 190

Val Asp Leu Val Lys Glu Leu Asp Arg Asp Thr Val Phe Ala Leu Val
        195                 200                 205

Asn Tyr Ile Phe Phe Lys Gly Lys Trp Glu Arg Pro Phe Glu Val Lys
        210                 215                 220

Asp Thr Glu Asp Glu Asp Phe His Val Asp Gln Val Thr Thr Val Lys
225                 230                 235                 240

Val Pro Met Met Lys Arg Leu Gly Met Phe Asn Ile Gln His Cys Lys
                245                 250                 255

Lys Leu Ser Ser Trp Val Leu Leu Met Lys Tyr Leu Gly Asn Ala Thr
            260                 265                 270

Ala Ile Phe Phe Leu Pro Asp Glu Gly Lys Leu Gln His Leu Glu Asn
        275                 280                 285

Glu Leu Thr His Asp Ile Ile Thr Lys Phe Leu Glu Asn Glu Asp Arg
    290                 295                 300

Arg Ser Ala Ser Leu His Leu Pro Lys Leu Ser Ile Thr Gly Thr Tyr
305                 310                 315                 320

Asp Leu Lys Ser Val Leu Gly Gln Leu Gly Ile Thr Lys Val Phe Ser
                325                 330                 335

Asn Gly Ala Asp Leu Ser Gly Val Thr Glu Glu Ala Pro Leu Lys Leu
            340                 345                 350

Ser Lys Ala Val His Lys Ala Val Leu Thr Ile Asp Glu Lys Gly Thr
        355                 360                 365

Glu Ala Ala Gly Ala Met Phe Leu Glu Ala Ile Pro Met Ser Ile Pro
    370                 375                 380

Pro Glu Val Lys Phe Asn Lys Pro Phe Val Phe Leu Met Ile Glu Gln
385                 390                 395                 400

Asn Thr Lys Ser Pro Leu Phe Met Gly Lys Val Val Asn Pro Thr Gln
                405                 410                 415

Lys

<210> SEQ ID NO 62
<211> LENGTH: 394
<212> TYPE: PRT
<213> ORGANISM: Homo sapiens
<220> FEATURE:
<221> NAME/KEY: MISC_FEATURE
<222> LOCATION: (355)..(358)
<223> OTHER INFORMATION: novel sequence
<220> FEATURE:
<221> NAME/KEY: MISC_FEATURE
<222> LOCATION: (356)..(357)
<223> OTHER INFORMATION: Xaa=any amino acid

<400> SEQUENCE: 62

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45
```

```
Asn Ile Phe Phe Ser Pro Val Ser Ile Ala Thr Ala Phe Ala Met Leu
 50                  55                  60

Ser Leu Gly Thr Lys Ala Asp Thr His Asp Glu Ile Leu Glu Gly Leu
 65                  70                  75                  80

Asn Phe Asn Leu Thr Glu Ile Pro Glu Ala Gln Ile His Glu Gly Phe
                 85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
130                 135                 140

Val Asn Phe Gly Asp His Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Asp Glu Asp Phe
        195                 200                 205

His Val Asp Gln Val Thr Thr Val Lys Val Pro Met Met Lys Arg Leu
210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285

Pro Lys Leu Ser Ile Thr Gly Thr Tyr Asp Leu Lys Ser Val Leu Gly
290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
            340                 345                 350

Leu Glu Arg Xaa Xaa Arg Ser Ile Pro Pro Glu Val Lys Phe Asn Lys
        355                 360                 365

Pro Phe Val Phe Leu Met Ile Glu Gln Asn Thr Lys Ser Pro Leu Phe
370                 375                 380

Met Gly Lys Val Val Asn Pro Thr Gln Lys
385                 390

<210> SEQ ID NO 63
<211> LENGTH: 394
<212> TYPE: PRT
<213> ORGANISM: Homo sapiens
<220> FEATURE:
<221> NAME/KEY: MISC_FEATURE
<222> LOCATION: (355)..(358)
<223> OTHER INFORMATION: native sequence
```

```
<400> SEQUENCE: 63

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
        195                 200                 205

His Val Asp Gln Val Thr Thr Val Lys Val Pro Met Met Lys Arg Leu
    210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285

Pro Lys Leu Ser Ile Thr Gly Thr Tyr Asp Leu Lys Ser Val Leu Gly
    290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
            340                 345                 350

Leu Glu Ala Ile Pro Met Ser Ile Pro Pro Glu Val Lys Phe Asn Lys
        355                 360                 365

Pro Phe Val Phe Leu Met Ile Glu Gln Asn Thr Lys Ser Pro Leu Phe
    370                 375                 380

Met Gly Lys Val Val Asn Pro Thr Gln Lys
385                 390
```

COMPOSITIONS, METHODS AND USES OF ALPHA 1-ANTITRYPSIN FOR EARLY INTERVENTION IN BONE MARROW TRANSPLANTATION AND TREATMENT OF GRAFT VERSUS HOST DISEASE

PRIORITY

This Application is a continuation-in-part (CIP) of U.S. application Ser. No. 11/916,521, now abandoned, filed Dec. 4, 2007, which is a national stage application of PCT Application No. PCT/US2006/22436, filed Jun. 7, 2006, which claims priority to U.S. Provisional Application No. 60/687,850 filed Jun. 7, 2005. All prior applications are incorporated herein in their entirety by reference for all purposes.

FIELD

Embodiments of the present invention relate to compositions and methods for treatment of subjects in need of or having a bone marrow transplant. Certain embodiments describe compositions and methods for treatment of conditions associated with bone marrow transplantations in a subject, for example, Graft versus Host Disease (GvHD) or bone marrow transplantation rejection. Some embodiments concern early or immediate bone marrow transplantation rejection. Certain embodiments relate to compositions and uses of alpha1-antitrypsin (α1-antitrypsin, AAT) and carboxyterminal peptide derivatives thereof and/or compositions and uses of serine protease inhibitors, immunomodulators or anti-inflammatory agent activity similar to that of AAT.

BACKGROUND

Serine Proteases

Serine proteases serve an important role in human physiology by mediating the activation of vital functions. In addition to their normal physiological function, serine proteases have been implicated in a number of pathological conditions in humans. Serine proteases are characterized by a catalytic triad consisting of aspartic acid, histidine and serine at the active site.

Naturally occurring serine protease inhibitors have been classified into families primarily on the basis of the disulfide bonding pattern and the sequence homology of the reactive site. Serine protease inhibitors, including the group known as serpins, have been found in microbes, in the tissues and fluids of plants, animals, insects and other organisms. At least nine separate, well-characterized proteins are now identified, which share the ability to inhibit the activity of various proteases. Several of the inhibitors have been grouped together, namely α1-antitrypsin-proteinase inhibitor, secretory leukocyte protease inhibitor or SLPI, anti-thrombin III, antichymotrypsin, C1-inhibitor, and α2-anti-plasmin, which are directed against various serine proteases, i.e., leukocyte elastase, thrombin, cathepsin G, chymotrypsin, plasminogen activators, and plasmin. These inhibitors are members of the α1-antitrypsin-proteinase inhibitor class. The protein α2-macroglobulin inhibits members of all four classes of endogenous proteases: serine, cysteine, aspartic, and metalloproteases. However, other types of protease inhibitors are class specific. For example, the α1-antitrypsin-proteinase inhibitor (also known as (α1-antitrypsin or AAT) and inter-alpha-trypsin inhibitor inhibit only serine proteases, α1-cysteine protease inhibitor inhibits cysteine proteases, and α1-anticollagenase inhibits collagenolytic enzymes of the metalloenzyme class.

The normal plasma concentration of ATT ranges from 1.3 to 3.5 mg/ml although it can behave as an acute phase reactant and increase 3-4-fold during host response to inflammation and/or tissue injury such as with pregnancy, acute infection, and tumors. It easily diffuses into tissue spaces and forms a 1:1 complex with target proteases, principally neutrophil elastase. Other enzymes such as trypsin, chymotrypsin, cathepsin G, plasmin, thrombin, tissue kallikrein, and factor Xa can also serve as substrates. The enzyme/inhibitor complex is then removed from circulation by binding to serpin-enzyme complex (SEC) receptor and catabolized by the liver and spleen. ATT appears to represent an important part of the defense mechanism against activity by serine proteases.

α1-antitrypsin is one of few naturally occurring mammalian serine protease inhibitors currently approved for the clinical therapy of protease imbalance. Therapeutic α1-antitrypsin has been commercially available since the mid 1980's and is prepared by various purification methods (see for example Bollen et al., U.S. Pat. No. 4,629,567; Thompson et al., U.S. Pat. Nos. 4,760,130; 5,616,693; WO 98/56821). Prolastin is a trademark for a purified variant of α1-antitrypsin and is currently sold by Talectris/Grifols Company (U.S. Pat. No. 5,610,285 Lebing et al., Mar. 11, 1997). Recombinant unmodified and mutant variants of α1-antitrypsin produced by genetic engineering methods are also known (U.S. Pat. No. 4,711,848); methods of use are also known, e.g., (α1-antitrypsin gene therapy/delivery (U.S. Pat. No. 5,399,346).

Graft Rejection

There are many diseases that culminate in organ dysfunction or failure. Representative non-limiting examples include renal failure due to diabetes melitus, hypertension, urinary output obstruction, drug-induced toxicity, or hypoperfusion, as well as cardiac dysfunction due to ischemic coronary artery disease, cardiomyopathy/infection, or valvulopathy. Pulmonary diseases include substantial damage due to chronic obstructive pulmonary disease (COPD, including chronic bronchitis and emphysema), AAT deficiency, cystic fibrosis, and interstitial fibrosis. Under certain conditions, the only therapeutic option for treatment of a subject may be organ transplantation. Pancreatic-islet transplantation provides diabetic patients with the only option for a tightly-controlled blood glucose level, as proven to be essential for prevention of diabetic complications. In the case of islets, post-transplant inflammation, which precedes immune rejection, is a critical determinant of graft survival. This early inflammation is mediated by cells other than the impending allospecific immune cells.

One challenge to therapeutic transplantation is the damaging effects of the host immune system on the transplant. MHC molecules exist on the surfaces of cells and the particular structures of MHC molecules are typically unique for each individual (with the exception of identical twins, where the MHC molecule complements are identical). The immune system is programmed to attack foreign or "non-self" MHC-bearing tissues. For these reasons, when an organ or tissue is transplanted into a recipient, an effort is made to optimize the degree of tissue matching between donor and recipient. MHC antigens are characterized for the recipient and donors. Matching a donor to an allograft recipient by MHC structure reduces the magnitude of the rejection response. An archetypal example is blood group matching. Most transplants are allografts that occur between non-identical members of the same species. Since these matches are imperfect, there is an expected graft rejection immune response associated with allografts. Current methods used, in order to enhance graft survival, include medications to suppress the immune response which can result in graft rejection. These medications are referred to immunosuppressant or antirejection drugs, such as prednisone, cyclosporine A, and cyclophosphamide, to name a few. As mentioned above, local inflammation is experienced immediately after grafting, and cells that are particularly sensitive to non-specific inflammation, such as islets, can endure graft dysfunction more severely than other types.

Despite advances in the field of antirejection therapy, graft maintenance remains a challenge since the available antirejection therapies are imperfect. For example, immunosuppression enhances the risk for opportunistic infection or neoplasia. Toxicities abound and include, but are not limited to, diabetes, organ dysfunction, renal failure, hepatic dysfunction, hematological defects, neuromuscular and psychiatric side effects, and many others. Therefore, there is a need for a more effective anti-rejection medical treatment that prolong graft survival and improve the quality of life.

Bone marrow transplantation is a unique kind of transplant where immune cells from a donor are transferred into a recipient, thereby conferring the donor immune system into the recipient. Here, the graft is capable of generating an immune response against the host, and this is termed "graft versus host" disease (GvHD). Immunosuppressive and antimicrobial treatment is required to block adverse consequences of GvHD, and a need exists for safer and more effective inhibitors of the adverse effects by the graft. In certain embodiments, a subject undergoing a bone marrow transplantation can be administered a therapeutically effective amount of AAT or carboxyterminal derivative thereof, to treat a subject early or immediately after bone marrow transplantation. In some embodiments, a therapeutically effective amount of AAT or carboxyterminal derivative thereof, can be used to treat a subject having GvHD or suspected of developing GvHD wherein the treatment reduces the incidence of or prevents mortality of a subject.

Because of some of the difficulties and inadequacies of conventional therapy for treating transplantation complications and associated side-effects, new therapeutic modalities are needed.

SUMMARY

Embodiments of the present invention provide for methods for treating a subject having or in need of a transplant. In accordance with these embodiments, a subject may be treated with a composition for reducing the risk of a transplant rejection or a side-effect of a transplant rejection in a subject. In accordance with this method the subject can be administered a composition including a compound that is capable of significantly reducing serine protease activity. The composition may be administered before transplantation, during transplantation, after transplantation or combination thereof. In addition, the composition may further include one or more anti-transplant rejection agent, anti-inflammatory agent, immunosuppressive agent, immunomodulatory agent, anti-microbial agent, or a combination thereof.

In certain embodiments of the invention, a composition capable of significantly reducing serine protease activity can include alpha-1-antitrypsin, an analog thereof or a combination thereof. A transplant of the present invention may include an organ transplant and/or a non-organ transplant. For example lung, kidney, heart, liver, cornea, skin, stem cells, soft tissue (e.g. facial component transplant), intestinal transplants, bone marrow, pancreatic islet, pancreas transplant or combination thereof are contemplated.

Embodiments of the present invention provide for methods for ameliorating symptoms or signs experienced by a subject having or in need of a transplant. In accordance with these embodiments, symptoms or signs may include conditions associated with graft versus host disease (GVHD), or graft rejection. In one example, methods disclosed herein may be used to treat a subject undergoing bone marrow transplantation. In another embodiment, symptoms or signs may include but is not limited to one or more of the following, kidney failure, lung failure, heart failure, malaise, fever, dry cough, anorexia, weight loss, myalgias, and chest pains, ventilatory compromise, sweating, nausea, vomiting, fever, abdominal pain, bloody diarrhea, mucosal ulcerations, reduced renal function (increased creatinine, decreased urine output), reduced pulmonary function (increased shortness of breadth, fever, cough, sputum, hypoxemia), reduced cardiac function (shortness of breach, chest pain, fatigue, pulmonary or peripheral edema, valvulopathy), reduced islet function (increased glucose, diabetes melitus), graft versus host disease (gastrointestinal (GI) ulceration, pulmonary failure, skin ulceration, coagulopothy, CNS dysfunction (mental status changes, coma) CMV (cytomeglovirus infection, viral, fungal parasitic infection)).

In some embodiments, a subject in need of a bone marrow transplant can be administered AAT or a carboxyterminal derivative of AAT before, during, or after bone marrow transplantation. In certain embodiments, bone marrow cells can be pretreated with a composition of AAT or a carboxyterminal derivative of AAT prior to introduction to a subject. In other embodiments, any cellular transplant matter can be pre-treated with a composition of AAT or a carboxyterminal derivative of AAT prior to introduction to a subject in need of a cellular transplant. Certain embodiments concern treating a subject with compositions disclosed herein in order to prevent a subject from developing GvHD. In accordance with these embodiments, a subject can be treated early or immediately after bone marrow transplantation. In other embodiments, a subject having had bone marrow transplantation demonstrating symptoms or signs of GvHD as recognized in the art can be given a composition of AAT and/or a carboxyterminal derivative of AAT in order to reduce or prevent mortality of the subject.

In certain embodiments, administration of a composition comprising AAT and/or carboxyterminal derived peptides of AAT reduced serum levels of proinflammatory cytokines in allogeneic recipients compared to a control not receiving the compositions. It was demonstrated that AAT treatment reduced the expansion of alloreactive T effector cells but enhanced the recovery of regulatory T cells (Tregs). In certain embodiments, AAT compositions were capable of altering the ratio of donor T effector to T regulatory cells in favor of reducing the pathological process. However, despite altering the ratio in vivo, AAT had no direct effects on either the donor T effector cells or Tregs in vitro. In contrast, AAT suppressed LPS-induced in vitro secretion of pro-inflammatory cytokines such as TNFα and IL-1β, enhanced the production of the anti-inflammatory cytokine IL-10 and impaired NFκB translocation in the host dendritic cells. In light of its long history of safety in humans, these findings suggest that administration of AAT represents a novel and viable strategy to mitigate clinical GvHD.

In other embodiments, it is contemplated that specific interleukins such as IL-32 can be inhibited in a subject in need of such a therapy. Compositions disclosed herein can be used to inhibit IL-32 in a subject having increased activity of this and other cytokines.

It is contemplated herein that AAT can include naturally occurring AAT harvested from human or other mammalian plasma and/or commercially available formulations such as Aralast™, Zemaira™, Kamada's agents and Prolastin™ and ProlastinC.™ Therapeutically effective doses of AAT can include those doses administered to AAT deficient patients or in a range of about 1 to about 100 mg/kg in a single or multiple dose regimen. It is contemplated herein that AAT or derivative thereof can be administered to a subject in need thereof and blood can be drawn from the subject in order to assess the level of AAT in the subject. In addition, once the level of AAT is determined, a health professional may administer more or less AAT to the subject depending on need.

Embodiments of the present invention provide methods for promoting prolonged graft survival and function in a subject including administering to a subject in need thereof a therapeutically effective amount of a composition including a substance exhibiting α1-antitrypsin or α1-antitrypsin analog or inhibitor of serine protease activity or a functional derivative thereof.

Embodiments of the present invention provide for methods for treating a subject in need of an immunotolerance therapy. In accordance with these embodiments, a subject may be treated with a composition for reducing the risk of a dysfunctional immune responses or a side-effect of a dysfunctional immune response in a subject. In another embodiment, methods herein provide for inducing immune tolerance specific for a graft and/or reduce the need for immunosuppressive therapy. In accordance with this embodiment, the immune system of the transplant recipient may have reduced or lost the specific ability to attack the graft while maintaining its ability to mount any other type of immune attack. In accordance with this method the subject can be administered a composition including a compound that is capable of significantly reducing serine protease activity or other activity associated with α1-antitrypsin or α1-antitrypsin analog. In certain embodiments, a composition capable of significantly reducing serine protease activity can include alpha-1-antitrypsin, an analog thereof or a combination thereof. In accordance with these embodiments, one example for immunotolerance therapy can include inhibiting cytokine production.

Embodiments of the present invention provide for methods for reducing TNFα (tumor necrosis factor alpha) levels in a subject including administering a composition including alpha-1-antitrypsin, an analog thereof or a combination thereof to a subject in need of such a treatment.

Embodiments of the present invention provide for methods for treating a subject in need of an immunotolerance therapy. In accordance with these embodiments methods are provided for reducing NO production and/or reducing apoptosis and/or inhibiting cytomegleovirus (infection and reactivation) including administering a composition including a compound that is capable of significantly reducing serine protease activity and/or other alpha-1-antitrypsin activity. In certain embodiments of the invention, a composition capable of significantly reducing serine protease activity and/or mimicking other alpha-1-antitrypsin activity can include alpha-1-antitrypsin, an analog thereof, or a combination thereof.

In certain embodiments of the present invention, the anti-inflammatory compound or immunomodulatory drug can include but is not limited to one or more of interferon, interferon derivatives including betaseron, beta-interferon, prostane derivatives including iloprost, cicaprost; glucocorticoids including cortisol, prednisolone, methyl-prednisolone, dexamethasone; immunsuppressives including cyclosporine A, FK-506, methoxsalene, thalidomide, sulfasalazine, azathioprine, methotrexate; lipoxygenase inhibitors comprising zileutone, MK-886, WY-50295, SC-45662, SC-41661A, BI-L-357; leukotriene antagonists; peptide derivatives including ACTH and analogs thereof; soluble TNF-receptors; TNF-antibodies; soluble receptors of interleukins, other cytokines, T-cell-proteins; antibodies against receptors of interleukins, other cytokines, T-cell-proteins; and calcipotriols; Celcept®, mycophenolate mofetil, and analogues thereof taken either alone or in combination.

Embodiments of the present invention provide for methods for reducing graft rejection in a subject. In accordance with these embodiments, a subject may be treated with a composition for reducing the risk of graft rejection responses or a side-effect of a graft rejection response in a subject. In accordance with this method, the subject can be administered a composition including a compound that is capable of significantly reducing serine protease activity. In certain embodiments, a composition capable of significantly reducing serine protease activity can include α1-antitrypsin, an analog thereof or a combination thereof. In one example, reducing graft rejection may include reducing the symptoms associated with graft rejection in a subject having an organ transplant, such as a kidney transplant or a bowel transplant or a non-organ transplant, such as a bone marrow transplant soft tissue transplant.

In yet another embodiment, the present invention may include combination therapies including compositions exhibiting α1-antitrypsin, an analog thereof, or substance with serine protease inhibitor activity. For example, a composition may include α1-antitrypsin and another serine protease inhibitor administered simultaneously or in separate compositions.

In accordance with embodiments disclosed herein, any of the disclosed compositions may be used to ameliorate symptoms associated with a transplant. These symptoms may include but are not limited to, infiltration of graft with cells and/or serum factors (for example, complement, anti-graft antibodies), increased cytokine and/or chemokine production, increased nitric oxide production, increased apoptosis and cell death, and increased immune response against the transplant tissue and/or cells.

In another aspect, the present invention provides for a method of ameliorating a symptom or sign associated with transplantation in a subject in need of said amelioration. In accordance with this embodiment, a composition may be administered to a subject such as a pharmaceutically effective amount of a substance of α1-antitrypsin, an analog thereof or serine protease inhibitor activity, wherein the composition is capable of reducing, preventing or inhibiting serine protease or protease activity and/or binds to the sec receptor or other activity.

In certain embodiments, synthetic and/or naturally occurring peptides may be used in compositions and methods of the present invention for example, providing serine protease inhibitor activity. Homologues, natural peptides, with sequence homologies to AAT including peptides directly derived from cleavage of AAT may be used or other peptides such as, peptides that inhibit serine proteases or have AAT-like activity. Other peptidyl derivatives, e.g., aldehyde or ketone derivatives of such peptides are also contemplated herein. Without limiting to AAT and peptide derivatives of AAT, compounds like oxadiazole, thiadiazole and triazole peptoids and substances comprising certain phenylenedialkanoate esters, CE-2072, UT-77, and triazole peptoids may be used. Examples of analogues are TLCK (tosyl-L-lysine chloromethyl ketone) or TPCK (tosyl-L-phenylalanine chloromethyl ketone).

In other embodiments, an agent that reduces the occurrence of graft rejection, promotes prolonged graft function or promotes prolonged allograft survival can also be an inhibitor of serine protease activity, an inhibitor of elastase, or an inhibitor of proteinase-3. An inhibitor of serine protease activity can include, but is not limited to, small organic molecules including naturally-occurring, synthetic, and biosynthetic molecules, small inorganic molecules including naturally-occurring and synthetic molecules, natural products including those produced by plants and fungi, peptides, variants of α1-antitrypsin, chemically modified peptides, and proteins.

In some embodiments, AAT peptides contemplated for use in the compositions and methods of the present invention are also intended to include any and all of those specific AAT peptides other than the 10 amino acid AAT peptides of SEQ ID NO. 1 depicted supra. Any combination of consecutive amino acids depicting a portion of AAT or AAT-like activity may be used, such as amino acids 2-12, amino acids 3-13, 4-14, etc. of SEQ ID NO. 1, as well as any and all AAT peptide fragments corresponding to select amino acids of SEQ ID NO. 1. Applicants are herein entitled to compositions based upon any and all AAT peptide variants based upon the amino acid sequence depicted in SEQ ID NO. 1.

In one aspect of the invention, the pharmaceutical compositions of the present invention are administered orally, systemically, via an implant, intravenously, topically, intrathecally, intratracheally, intracranially, subcutaneously, intravaginally, intraventricularly, intranasally such as inhalation, mixed with grafts by flushing of organ or suspension of cells, or any combination thereof.

As such, those skilled in the art will appreciate that the conception, upon which this disclosure is based, can readily be used as a basis for designing other methods for carrying out the several features and advantages of the present invention.

BRIEF DESCRIPTION OF THE DRAWINGS

The following drawings form part of the present specification and are included to further demonstrate certain embodiments of the present invention. The embodiments may be better understood by reference to one or more of these drawings in combination with the detailed description of specific embodiments presented herein.

FIGS. 3A-3C illustrates an exemplary method of the effect of AAT on MHC-incompatible, NIH-3T3-fibroblast-elicited peritoneal cellular infiltrates. (A) Cell numbers. The number of cells in each subpopulation was calculated from the percentages obtained by FACS analysis, and total number of cells in the infiltrate. (B) Representative FACS analysis. (C) Effect of AAT on intensity and function of infiltrate elicited by islet allograft. Left, Hematoxilyn and Eosin (H&E) staining of day 7 islet allografts. Right, Immunohistochemistry (IHC) with anti-insulin antibodies of day 15 islet grafts. R, renal parenchyma, G, graft, C, renal capsule.

FIGS. 4A-4H illustrates an exemplary method of the effect of AAT on islet responses. (A-D) Mean±SEM of A. nitric levels, B. Cell viability and C. MIP-1α levels. Dashed line represents islets incubated at one-30th the concentration of IFNγ/IL-1β. D. TNFα levels. (E) Insulin induction assay. (F) Streptozotocin toxicity. Each image depicts a representative islet from one pancreas. (G) Cellular content of islets. (H) MHC class II expression.

FIGS. 6A-6D illustrates the effect of AAT on Islet allograft transplantation. 6A illustrates the time course study after transplantation. 6B illustrates an immune infiltrate found outside the graft area. 6C illustrates an increase in the presence of CD4+ and a comparative decrease in monocytes and neutrophils. 6D illustrates levels of glucose reflecting a level of tolerance with respect to days following allografting of the same donor (left) and a $3^{rd}$ donor re-graft (right), indicating induction of specific immune tolerance.

FIGS. 7A-7E illustrates the production of AAT by islet cell and reflection of islet graft survival. 7A illustrates a time course expression of mouse AAT mRNA after cytokine production (IL-1β and IFNγ) (left) and at 8 hours (right). 7B illustrates an example of islet injury during pancreatitis; the histology of normal islets (top left), the histology of islets of an inflamed pancreas (top right) and expression of mouse AAT in islets obtained from the pancreata in an acute pancreatitis model (bottom). 7C illustrates an example of samples of islet allografts taken post grafting and the percent change in AAT mRNA levels were assessed. 7D illustrates an example of islet protection from cytokine injury with endogenous AAT by introducing oncostatin M (an interleukin 6 (IL-6) family member) that induces AAT expression in islets, oncostatin M and AAT levels (top left); nitric oxide and viability levels assessed (top right) and nitric oxide production representing islet viability after 4 day exposure to oncostatin M and AAT production decreasing cytokine effects on the islets (bottom).

FIGS. 8A-8D illustrates the effect of AAT on human islets and the production of nitric oxide (8A), TNF-α production (8B) IL-6 (8C) and IL-8 (8D).

DESCRIPTION OF ILLUSTRATIVE EMBODIMENTS

Definitions

Figure 1A:
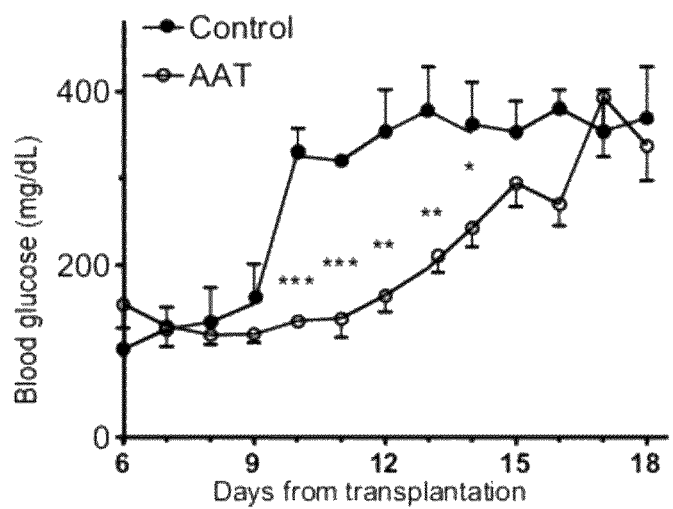
FIGS. 1A-1D illustrates an exemplary method of treating islet allografts with AAT. Islets from DBA/2 mice (H-2d) were transplanted under the renal capsule of streptozotocin-induced hyperglycemic C57BL/6 mice (H-2b). (A) Glucose levels from days 6-18. (B) Treatment protocols. Control and full AAT treatment are described in panel A. Early AAT treatment consists of treatment on days −1, 1 and 3 (2 mg, n=3). Late AAT treatment consists of treatment from day 2 and on every 2 days (2 mg, n=3). (C) Effect of mouse anti-human-AAT antibodies. Dashed line indicates post transplantation glucose levels of a mouse under full AAT treatment protocol (see A, B) that was immunized by multiple administrations of human AAT prior to transplantation (1 representative, n=3). Solid line indicates glucose levels of a non-immunized mouse treated under full AAT treatment protocol (1 representative, n=10). Arrow indicates detection of treatment-induced, anti-human-AAT antibodies in the non-immunized representative mouse. (D) Comparison of day 15 post-transplantation glucose levels in mice that were under full treatment protocol with ALB (n=3) or AAT (non-immunized n=10, immunized n=3). Of the AAT-treated group, antibodies were detected on day 15 in 3/3 immunized mice and in 6/10 non-immunized mice.

Terms that are not otherwise defined herein are used in accordance with their plain and ordinary meaning.

As used herein, "a" or "an" may mean one or more than one of an item.

As used herein "analog of alpha-1-antitrypsin" may mean a compound having alpha-1-antitrypsin-like activity. In one embodiment, an analog of alpha-1-antitrypsin is a functional derivative of alpha-1-antitrypsin. In a particular embodiment, an analog of alpha-1-antitrypsin is a compound capable of significantly reducing serine protease activity. For example, an inhibitor of serine protease activity has the capability of inhibiting the proteolytic activity of trypsin, elastase, kallikrein, thrombin, cathepsin G, chymotrypsin, plasminogen activators, plasmin and/or other serine proteases.

As used herein "immunomodulatory drugs or agents", it is meant, e.g., agents which act on the immune system, directly or indirectly, e.g., by stimulating or suppressing a cellular activity of a cell in the immune system, e.g., T-cells, B-cells, macrophages, or antigen presenting cells (APC, dendritic cells), or by acting upon components outside the immune system which, in turn, stimulate, suppress, or modulate the immune system, e.g. cytokines, e.g., hormones, receptor agonists or antagonists, and neurotransmitters; immunomodulators can be, e.g., immunosuppressants or immunostimulants.

It is to be understood that the terminology and phraseology employed herein are for the purpose of description and should not be regarded as limiting Detailed Description of the Invention In the following sections, various exemplary compositions and methods are described in order to detail various embodiments of the invention. It will be obvious to one skilled in the art that practicing the various embodiments does not require the employment of all or even some of the specific details outlined herein, but rather that concentrations, times and other specific details may be modified through routine experimentation. In some cases, well known methods or components have not been included in the description.

Embodiments of the present invention provide for methods for treating a subject having or in need of a transplant. In accordance with these embodiments, a subject may be treated with a composition capable of significantly reducing serine protease activity. In addition, one embodiment of the present invention provides for methods including treating a subject with a composition comprising a compound having α-1-antitrypsin activity. In one embodiment, the composition can include α-1-antitrypsin, analog thereof or a serine protease inhibitor to for example, promote transplant survival or reduce a side effect of the transplant. Further, the administration of the composition can be before transplantation, during transplantation, after transplantation or combination thereof. In addition, the composition may further include one or more additional therapies such as immunosuppressive therapies. A transplant of the present invention may include transplantation of an organ such as lung, kidney, heart, liver, skin, pancreas, or bowel organ or non-organ such bone marrow, pancreatic islet, cornea, and/or soft tissue.

Serine protease inhibitors, have been found in a variety of organisms. At least nine separate, well-characterized proteins are now identified, which share the ability to inhibit the activity of various proteases. Several of the inhibitors have been grouped together, such as the $\alpha_1$-antitrypsin-proteinase inhibitor. Serine proteases include but are not limited to leukocyte elastase, thrombin, cathepsin G, chymotrypsin, plasminogen activators, and plasmin.

Embodiments of the present invention provide for methods for promoting transplantation, graft survival, reducing graft rejection and/or reducing or preventing side-effects associated with graft rejection. In accordance with these embodiments, side-effects may include conditions associated with graft versus host disease (GVHD), or graft rejection. In one example, methods disclosed herein may be used to treat a subject undergoing bone marrow transplantation. In another embodiment, symptoms or signs may include but is not limited to one or more of the following, malaise, fever, dry cough, myalgias, and chest pains, ventilatory compromise, sweating, nausea, vomiting, fever, abdominal pain, bloody diarrhea, mucosal ulcerations, reduced renal function (increased creatinine, decreased urine output), reduced pulmonary function (increased shortness of breadth, fever, cough, sputum, hypoxemia), reduced cardiac function (shortness of breach, chest pain, fatigue, pulmonary or peripheral edema, valvulopathy), reduced islet function (increased glucose, diabetes mellitus), graft versus host disease (gastrointestinal (GI) ulceration, pulmonary failure, skin ulceration).

Embodiments of the present invention provide for methods for treating a subject in need of an immunotolerance therapy. In accordance with these embodiments, a subject may be treated with a composition for inducing immune tolerance. This achieved while reducing the risk of a dysfunctional immune responses or a side-effect of a dysfunctional immune response in a subject as typically encountered during standard immune suppression. For example, a dysfunctional immune response may be an effect of graft rejection, pneumonia, sepsis, fungal infection, cancer. In accordance with this method the subject can be administered a composition including a compound that is capable of significantly reducing serine protease activity or other activity associated with α1-antitrypsin or α1-antitrypsin analog. In certain embodiments, a composition capable of significantly reducing serine protease activity can include α-1-antitrypsin, an analog thereof or a combination thereof. In accordance with these embodiments, one example for immunotolerance therapy can include inhibiting cytokine production.

Any of the embodiments detailed herein may further include one or more a therapeutically effective amount of anti-microbial drugs anti-inflammatory agent, immunomodulatory agent, or immunosuppressive agent or combination thereof.

Non-limiting examples of anti-rejection agents/drugs may include for example cyclosporine, azathioprine, corticosteroids, FK506 (tacrolimus), RS61443, mycophenolate mofetil, rapamycin (sirolimus), mizoribine, 15-deoxyspergualin, and/or leflunomide or any combination thereof.

In addition, other combination compositions of methods disclosed in the present invention include certain antibody-based therapies. Non-limiting examples include, polyclonal anti-lymphocyte antibodies, monoclonal antibodies directed at the T-cell antigen receptor complex (OKT3, TIOB9), monoclonal antibodies directed at additional cell surface antigens, including interleukin-2 receptor alpha. Antibody-based therapies may be used as induction therapy and/or anti-rejection drugs in combination with the compositions and methods of the present invention.

Embodiments of the present invention provide for methods treating a subject in need of an immunotolerance therapy. In accordance with these embodiments, a subject may be treated with a composition capable of significantly reducing serine protease activity. In one embodiment, the composition can include α-1-antitrypsin, analog thereof or a serine protease inhibitor to for example, to reduce or inhibit the production of cytokines. In accordance with these embodiments, combination therapies are contemplated, such as combining α-1-antitrypsin composition with an anti-inflammatory agent.

In one particular embodiment, the present inventions provide for methods for reducing levels and activities of cytokines such as TNFα (tumor necrosis factor alpha). For example, the composition can include alpha-1-antitrypsin or analog thereof or combination thereof alone or in combination with other therapies.

GvHD

In some embodiments, a subject in need of a bone marrow transplant can be administered AAT or a carboxyterminal derivative of AAT before, during, or after bone marrow transplantation. In certain embodiments, bone marrow cells can be pretreated with a composition of AAT or a carboxyterminal derivative of AAT prior to introduction to a subject. In other embodiments, any cellular transplant matter can be pre-treated with a composition of AAT or a carboxyterminal derivative of AAT prior to introduction to a subject in need of a cellular transplant. Certain embodiments concern treating a subject with compositions disclosed herein in order to prevent a subject from developing GvHD. In accordance with these embodiments, a subject can be treated early or immediately after bone marrow transplantation. In other embodiments, a subject having had bone marrow transplantation demonstrating symptoms or signs of GvHD as recognized in the art can be given a composition of AAT and/or a carboxyterminal derivative of AAT in order to reduce or prevent mortality of the subject.

Acute graft-versus-host disease (GvHD) is a major complication that prevents successful outcomes after allogeneic bone marrow transplantation (BMT), an effective therapy for hematological malignancies and other non-malignant conditions such as leukemia, severe aplastic anemia, lymphoma, multiple myeloma, immune deficiency disorder, solid-tumor cancer, breast, cancer, ovarian cancer among others. Previous studies demonstrated that donor T cells and host antigen presenting cells along with several proinflammatory cytokines induce GvHD and contribute to its severity. Evidence previously presented demonstrates that alpha-1-anti-trypsin (AAT) can reduce production of proinflammatory cytokines, induce anti-inflammatory cytokines and interfere with maturation of dendritic cells. Using well-characterized mouse models of BMT, effects of AAT on GvHD severity have been studied herein. Some embodiments of the present invention concern administration of AAT early or immediately after BMT (early intervention) decreased severity of the disease. In other embodiments, administration of a composition of AAT early or immediately after BMT reduces mortality in a subject having or at risk of developing GvHD. Other embodiments disclosed herein demonstrated that administration of AAT and/or carboxyterminal derived peptides of AAT reduced bone marrow cell rejections if introduced soon after transplantation.

The pathophysiology of GvHD involves donor T cell interactions with host antigen presenting cells and the subsequent production of proinflammatory cytokines (cytokine storm), alongside activation of alloreactive T effector cells (T effectors) that cause target organ damage. By contrast, donor derived mature foxp3+T regulatory cells (Tregs) can downregulate alloreactivity. Thus the ratio between donor T effectors and donor Tregs plays a key role in the severity of GvHD. Attempts to reduce GvHD by T cell depletion have led to significant relapse of malignancy due to the loss of graft versus leukemia (GVL), failure of engraftment, and an increase in the rate of opportunistic infections.

In certain embodiments, administration of a composition comprising AAT and/or carboxyterminal derived peptides of AAT reduced serum levels of proinflammatory cytokines in allogeneic recipients compared to a control not receiving the compositions. It was demonstrated that AAT treatment reduced the expansion of alloreactive T effector cells but enhanced the recovery of regulatory T cells (Tregs). In certain embodiments, AAT compositions were capable of altering the ratio of donor T effector to T regulatory cells in favor of reducing the pathological process. However, despite altering the ratio in vivo, AAT had no direct effects on either the donor T effector cells or Tregs in vitro. In contrast, AAT suppressed LPS-induced in vitro secretion of pro-inflammatory cytokines such as TNFα and IL-1β, enhanced the production of the anti-inflammatory cytokine IL-10 and impaired NFκB translocation in the host dendritic cells. In light of its long history of safety in humans, these findings suggest that administration of AAT represents a novel and viable strategy to mitigate clinical GvHD.

IL-32

Interleukin-32 (IL-32) was originally identified in NK cells and IL-2-activated human T-lymphocytes. As T-cells are activated in allogeneic transplantation, the role of IL-32 in human mixed lymphocyte cultures (MLC) and graft-versus-host-disease (GVHD) was determined. In allogeneic MLC, IL-32 increased 2-fold in responding T-cells, accompanied by 5-fold increases of TNFα, IL-6 and IL-8. After allogeneic hematopoietic cell transplantation, IL-32 mRNA levels in blood leukocytes were statistically significantly higher in patients with acute GVHD (n=10) than in serial samples from patients who did not develop acute GVHD (n=5; p=0.02). No significant changes in IL-32 levels were present in patients with treated (n=14) or untreated (n=8) chronic GVHD, compared to healthy controls (n=8) (p=0.5 and p=0.74, respectively). As IL-32 is activated by proteinase-3 (PR3), the effect of α-1 antitrypsin (AAT) on IL-32 levels and showed suppression of IL-32 and T-lymphocyte proliferation in MLC was examined. In an MHC-minor antigen disparate murine transplant model, pre- and post-conditioning treatment with AAT resulted in attenuation or prevention of GVHD and superior survival compared to albumin-treated controls (e.g. 80% versus 44%; p=0.04). These findings suggest that AAT modulates immune and inflammatory functions and may represent a novel approach to prevent or treat GVHD.

In certain embodiments, it is contemplated that AAT or AAT-related compositions (e.g. mutants and peptide derivatives) can prevent IL-32 activation, thereby interfering with alloactivation. Although this activity is not restricted to IL-32, and, hence AAT will affect additional targets, an inhibitory effect of ATT on alloactivation might prove beneficial in the prevention or therapy of GVHD.

It is contemplated herein that AAT can include naturally occurring AAT harvested from human or other mammalian plasma and/or commercially available formulations such as Aralast™, Zemaira™, Aralast™, Kamada's agents and Prolastin™ and ProlastinC.™ Therapeutically effective doses of AAT can include those doses administered to AAT deficient patients or in a range of about 1 to about 100 mg/kg in a single or multiple dose regimen. It is contemplated herein that AAT or derivative thereof can be administered to a subject in need thereof and blood can be drawn from the subject in order to assess the level of AAT in the subject. In addition, once the level of AAT is determined, a health professional may administer more or less AAT to the subject depending on need and circumstances of the subject.

In one embodiment, the reduction, prevention or inhibition of rejection of transplantation or side effects thereof associated with one or more of each of the above-recited conditions may be about 10-20%, 30-40%, 50-60%, or more reduction or inhibition due to administration of the disclosed compositions.

In one embodiment of the present invention a composition may include compounds that engage molecules for the SEC receptor to treat a subject undergoing a transplantation and/or in need of immunotolerance therapy. In each of the recited methods, an α1-antitrypsin (e.g. mammalian derived) or inhibitor of serine protease activity substance contemplated for use within the methods of the present invention can include a series of peptides including carboxy-terminal amino acid peptides corresponding to AAT. These pentapeptides can be represented by a general formula (I):

I-A-B-C-D-E-F-G-H-II (note: in the Sequence Listing F=X), wherein I is Cys or absent; A is Ala, Gly; Val or absent; B is Ala, Gly, Val, Ser or absent; C is Ser, Thr or absent; D is Ser, Thr, Ans, Glu, Arg, Ile, Leu or absent; E is Ser, Thr, Asp or absent; F is Thr, Ser, Asn, Gln, Lys, Trp or absent; G is Tyr or absent; H is Thr, Gly, Met, Met(O), Cys, Thr or Gly; and II is Cys, an amide group, substituted amide group, an ester group or absent, wherein the peptides includes 4 or more consecutive amino acids and physiologically acceptable salts thereof. Among this series of peptides, several are equally acceptable including FVFLM (SEQ ID NO. 1), FVFAM (SEQ. ID NO. 2), FVALM (SEQ. ID NO. 3), FVFLA (SEQ. ID NO. 4), FLVFI (SEQ. ID NO. 5), FLMII (SEQ. ID NO. 6), FLFVL (SEQ. ID NO. 7), FLFVV (SEQ. ID NO. 8), FLFLI (SEQ. ID NO. 9), FLFFI (SEQ. ID NO. 10), FLMFI (SEQ. ID NO. 11), FMLLI (SEQ. ID NO. 12), FIIMI (SEQ. ID NO. 13), FLFCI (SEQ. ID NO. 14), FLFAV (SEQ. ID) NO. 15), FVYLI (SEQ. ID NO. 16), FAFLM (SEQ. ID NO. 17), AVFLM (SEQ. ID NO. 18), and any combination thereof.

In several embodiments herein, AAT peptides contemplated for use in the compositions and methods of the present invention are also intended to include any and all of those specific AAT peptides of SEQ ID NO. 1 depicted supra. Any combination of consecutive amino acids simulating AAT or AAT-like activity may be used, such as amino acids 2-12, amino acids 3-14, 4-16, etc.

In each of the above-recited methods, α1-antitrypsin or analogs thereof are contemplated for use in a composition herein. These analogs may include peptides. The peptides may include but are not limited to amino acid peptides containing MPSSVSWGIL (SEQ. ID NO. 19); LAGLCCLVPV (SEQ. ID NO. 20) SLAEDPQGDA (SEQ. ID NO. 21); AQKTDTSHHD (SEQ. ID NO. 22) QDHPTFNKIT (SEQ. ID NO. 23); PNLAEFAFSL (SEQ. ID NO. 24); YRQLAHQSNS (SEQ. ID NO. 25); TNIFFSPVSI (SEQ. ID NO. 26); ATAFAMLSLG (SEQ. ID NO. 27); TKADTHDEIL (SEQ. ID NO. 28); EGLNFNLTEI (SEQ. ID NO. 29); PEAQIHEGFQ (SEQ. ID) NO. 30); ELLRTLNQPD (SEQ. ID NO. 31); SQLQLTTGNG (SEQ. ID NO. 32); LFLSEGLKLV (SEQ. ID NO. 33); DKFLEDVKKL (SEQ. ID NO. 34); YHSEAFTVNF (SEQ. ID NO. 35); GDHEEAKKQI (SEQ. ID NO. 36); NDYVEKGTQG (SEQ. ID NO. 37); KIVDLVKELD (SEQ. ID NO. 38); RDTVFALVNY (SEQ. ID NO. 39); IFFKGKWERP (SEQ. ID NO. 40); FEVKDTEDED (SEQ. ID NO. 41); FHVDQVTTVK (SEQ. ID NO. 42); VPMMKRLGMF (SEQ. ID NO. 43); NIQHCKKLSS (SEQ. ID NO. 44); WVLLMKYLGN (SEQ. ID NO. 45); ATAIFFLPDE (SEQ. ID NO. 46); GKLQHLENEL (SEQ. ID NO. 47); THDIITKFLE (SEQ. ED NO. 48); NEDRRSASLH (SEQ. ID NO. 49); LPKLSITGTY (SEQ. ID NO. 50); DLKSVLGQLG (SEQ. ID NO. 51); ITKVFSNGAD (SEQ. ID NO. 52); LSGVTEEAPL (SEQ. ID NO. 53); KLSKAVHKAV (SEQ. ID NO. 54); LTIDEKGTEA (SEQ. ID NO. 55); AGAMFLEAIP (SEQ. ID NO. 56); MSIPPEVKFN (SEQ. ID NO. 57); KPFVFLMIEQ (SEQ. ID NO. 58); NTKSPLFMGK (SEQ. ID NO. 59); VVNPTQK (SEQ. ID NO. 60), or any combination thereof.

In Accordance with embodiments of the present invention, the peptide can be protected or derivitized in by any means known in the art for example, N-terminal acylation, C-terminal amidation, cyclization, etc. In a specific embodiment, the N-terminus of the peptide is acetylated.

Pharmaceutical Compositions

Embodiments herein provide for administration of compositions to subjects in a biologically compatible form suitable for pharmaceutical administration in vivo. By "biologically compatible form suitable for administration in vivo" is meant a form of the active agent (i.e. pharmaceutical chemical, protein, gene, antibody etc of the embodiments) to be administered in which any toxic effects are outweighed by the therapeutic effects of the active agent. Administration of a therapeutically active amount of the therapeutic compositions is defined as an amount effective, at dosages and for periods of time necessary to achieve the desired result. For example, a therapeutically active amount of a compound may vary according to factors such as the disease state, age, sex, and weight of the individual, and the ability of antibody to elicit a desired response in the individual. Dosage regima may be adjusted to provide the optimum therapeutic response.

In one embodiment, the compound (i.e. pharmaceutical chemical, protein, peptide etc. of the embodiments) may be administered in a convenient manner such as subcutaneous, intravenous, by oral administration, inhalation, transdermal application, intravaginal application, topical application, intranasal or rectal administration. Depending on the route of administration, the active compound may be coated in a material to protect the compound from the degradation by enzymes, acids and other natural conditions that may inactivate the compound. In a preferred embodiment, the compound may be orally administered. In another preferred embodiment, the compound may be administered intravenously. In one particular embodiment, the compound may be administered intranasally, such as inhalation.

A compound may be administered to a subject in an appropriate carrier or diluent, co-administered with enzyme inhibitors or in an appropriate carrier such as liposomes. The term "pharmaceutically acceptable carrier" as used herein is intended to include diluents such as saline and aqueous buffer solutions. It may be necessary to coat the compound with, or co-administer the compound with, a material to prevent its inactivation. The active agent may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use may be administered by means known in the art. For example, sterile aqueous solutions (where water soluble) or dispersions and sterile powders for the extemporaneous preparation of sterile injectable solutions or dispersion may be used. In all cases, the composition cant be sterile and can be fluid to the extent that easy syringability exists. It might be stable under the conditions of manufacture and storage and may be preserved against the contaminating action of microorganisms such as bacteria and fungi. The pharmaceutically acceptable carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of microorganisms can be achieved by heating, exposing the agent to detergent, irradiation or adding various antibacterial or antifungal agents.

Sterile injectable solutions can be prepared by incorporating active compound (e.g. a compound that reduces serine protease activity) in the required amount in an appropriate solvent with one or a combination of ingredients enumerated above, as required, followed by filtered sterilization.

Aqueous compositions can include an effective amount of a therapeutic compound, peptide, epitopic core region, stimulator, inhibitor, and the like, dissolved or dispersed in a pharmaceutically acceptable carrier or aqueous medium. Compounds and biological materials disclosed herein can be purified by means known in the art.

Solutions of the active compounds as free-base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. Prolonged absorption of the injectable compositions can be brought about by the use in the compositions of agents delaying absorption, for example, aluminum monostearate and gelatin.

Upon formulation, solutions will be administered in a manner compatible with the dosage formulation and in such amount as is therapeutically effective. The formulations are easily administered in a variety of dosage forms, such as the type of injectable solutions described above. It is contemplated that slow release capsules, timed-release microparticles, and the like can also be employed. These particular aqueous solutions are especially suitable for intravenous, intramuscular, subcutaneous and intraperitoneal administration.

The active therapeutic agents may be formulated within a mixture to comprise about 0.0001 to 1.0 milligrams, or about 0.001 to 0.1 milligrams, or about 0.1 to 1.0 or even about 1 to 10 gram per dose. Single dose or multiple doses can also be administered on an appropriate schedule for a predetermined condition.

In another embodiment, nasal solutions or sprays, aerosols or inhalants may be used to deliver the compound of interest. Additional formulations that are suitable for other modes of administration include suppositories and pessaries. A rectal pessary or suppository may also be used. In general, for suppositories, traditional binders and carriers may include, for example, polyalkylene glycols or triglycerides; such suppositories may be formed from mixtures containing the active ingredient in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate and the like. In certain defined embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such therapeutically useful compositions is such that a suitable dosage will be obtained.

A pharmaceutical composition may be prepared with carriers that protect active ingredients against rapid elimination from the body, such as time-release formulations or coatings. Such carriers include controlled release formulations, such as, but not limited to, microencapsulated delivery systems, and biodegradable, biocompatible polymers, such as ethylene vinyl acetate, polyanhydrides, polyglycolic acid, polyorthoesters, polylactic acid and others are known.

Pharmaceutical compositions are administered in an amount, and with a frequency, that is effective to inhibit or alleviate side effects of a transplant and/or to reduce or prevent rejection. The precise dosage and duration of treatment may be determined empirically using known testing protocols or by testing the compositions in model systems known in the art and extrapolating therefrom. Dosages may also vary with the severity of the condition. A pharmaceutical composition is generally formulated and administered to exert a therapeutically useful effect while minimizing undesirable side effects. In general, an oral dose ranges from about 200 mg to about 1000 mg, which may be administered for example 1 to 3 times per day.

It will be apparent that, for any particular subject, specific dosage regimens may be adjusted over time according to the individual need. The preferred doses for administration can be anywhere in a range between about 0.01 mg and about 100 mg per ml of biologic fluid of treated patient. In one particular embodiment, the range can be between 1 and 100 mg/kg which can be administered daily, every other day, biweekly, weekly, monthly etc. In another particular embodiment, the range can be between 10 and 75 mg/kg introduced weekly to a subject. The therapeutically effective amount of α1-antitrypsin, peptides, or drugs that have similar activities as α1-antitrypsin or peptides can be also measured in molar concentrations and can range between about 1 nM to about 2 mM.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent.

Liposomes can be used as a therapeutic delivery system and can be prepared in accordance with known laboratory techniques. In addition, dried lipids or lyophilized liposomes prepared as previously described may be reconstituted in a solution of active agent (e.g. nucleic acid, peptide, protein or chemical agent), and the solution diluted to an appropriate concentration with a suitable solvent known to those skilled in the art. The amount of active agent encapsulated can be determined in accordance with standard methods.

In a preferred embodiment, a nucleic acid (e.g. α1-antitrypsin or analogs thereof) and the lipid dioleoylphosphatidylcholine may be employed. For example, nuclease-resistant oligonucleotides may be mixed with lipids in the presence of excess t-butanol to generate liposomal-oligonucleotides for administration.

The pharmaceutical compositions containing the α1-antitrypsin, analog thereof, or inhibitor of serine protease activity or a functional derivative thereof may be administered to individuals, particularly humans, for example by subcutaneously, intramuscularly, intranasally, orally, topically, transdermally, parenterally, gastrointestinally, transbronchially and transalveolarly. Topical administration is accomplished via a topically applied cream, gel, rinse, etc. containing therapeutically effective amounts of inhibitors of serine proteases. Transdermal administration is accomplished by application of a cream, rinse, gel, etc. capable of allowing the inhibitors of serine proteases to penetrate the skin and enter the blood stream. In addition, osmotic pumps may be used for administration. The necessary dosage will vary with the particular condition being treated, method of administration and rate of clearance of the molecule from the body.

In each of the aforementioned compositions and methods, a compound having serine protease inhibitor activity and/or having α1-antitrypsin activity or analog thereof may be used in a single therapeutic dose, acute manner or a chronic manner to treat episodes or prolonged bouts, respectively, in promoting graft survival, treating graft rejection and/or associated graft rejection-induced side-effects.

In certain embodiments of the methods of the present invention, the subject may be a mammal such as a human or a veterinary and/or a domesticated animal.

Therapeutic Methods

In one embodiment of the present invention, methods provide for treating a subject in need of or undergoing a transplant. For example, treatments for reducing graft rejection, promoting graft survival, and promoting prolonged graft function by administering to a subject in need thereof a therapeutically effective amount of a composition. The composition can include a compound capable of inhibiting at least one serine protease for example, α1-antitrypsin, or analog thereof.

Preserving the Graft During Transplant Before Engraftment

According to the methods of the present invention, transplantation complications can be reduced or inhibited to obtain important therapeutic benefits. Therefore, administration of a therapeutic composition contemplated by embodiments of the invention, i.e., α1-antitrypsin, derivative or analog thereof, can be beneficial for the treatment of transplantation complications or conditions.

Another beneficial effect of use of the compositions and methods of the present invention include reducing negative effects on an organ or non-organ during explant, isolation, transport and/or prior to implantation. For example, the composition can reduce apoptosis, reduce production of cytokines, reduce production of NO, or combination thereof in an organ for transplant. In one particular embodiment, a composition can include a compound that includes alpha-1-antitrypsin, an analog thereof, a serine protease inhibitor, serine protease inhibitor-like activity, analog thereof or a combination thereof. The transplant organ or non-organ can include but is not limited to, lung, kidney, heart, liver, soft tissue, skin, pancreas, intestine, soft tissue cornea, bone marrow, stem cell, pancreatic islet, and combination thereof.

In a further embodiment, the methods and compositions of the invention are useful in the therapeutic treatment of graft rejection associated side effects. In a yet further embodiment, graft rejection associated side effects can be prevented by the timely administration of the agent of the invention as a prophylactic, prior to onset of one or more symptoms, or one or more signs, or prior to onset of one or more severe symptoms or one or more signs of a graft rejection associated disease. Thus, a patient at risk for a particular graft rejection or graft rejection-associated disease or clinical indication can be treated with serine protease inhibitors, for example, (Benzyloxycarbonyl)-L-Valyl-N-[1-(3-(5-(3-Trifluoromethylbenzyl)-1,2,4-oxadiazolyl)carbonyl)-2-(S)-Methylpropyl]-Prolinamide; as a prophylactic measure.

It is contemplated herein that the present compositions and methods of the present invention can be used to treat patients with one or more grafts who require chronic therapy to maintain graft integrity, and such patients will therefore benefit from indefinite or chronic use of the rejection repressive therapy of the methods of the present invention. Yet another embodiment can be used to treat flairs of acute rejection so as to minimize the effects of acute clinical rejection, organ failure, and/or eventual destruction of the graft.

Desirable blood levels may be maintained by continuous infusion to provide about 0.01-5.0 mg/kg/hr or by intermittent infusions containing about 0.4-20 mg/kg of the active ingredient(s). Buffers, preservatives, antioxidants and the like can be incorporated as required. It is intended herein that the ranges recited also include all those specific percentage amounts between the recited range. For example, the range of about 0.4 to 20 mg/kg also encompasses 0.5 to 19.9%, 0.6 to 19.8%, etc, without actually reciting each specific range therewith, Serine Protease Inhibitors It is to be understood that the present invention is not limited to the examples described herein, and other serine proteases known in the art can be used within the limitations of the invention. For example, one skilled in the art can easily adopt inhibitors as described in WO 98/24806, which discloses substituted oxadiazole, thiadiazole and triazole as serine protease inhibitors. U.S. Pat. No. 5,874,585 discloses substituted heterocyclic compounds useful as inhibitors of serine proteases for example, (benzyloxycarbonyl)-L-valyl-N-[1-(3-(5-(3-trifluoromethylbenzyl)-1,2,4-oxa diazolyl) carbonyl)-2-(S)-methylpropyl]-prolinamide benzyloxycarbonyl)-L-valyl-N-[1-(3-(5-(2-phenylethyl)-1,2,4-oxadiazolyl)carbonyl)-2-(S)-methylpropyl]-L-prolinamide; and (benzyloxycarbonyl)-L-valyl-N-[1-(3-(5-(2-methoxybenzyl)-1,2,4-oxadiazolyl)carbonyl)-2-(S)-methylpropyl]-L-prolinamide.

α1-antitrypsin is a glycoprotein of MW 51,000 with 417 amino acids and 3 oligosaccharide side chains. Human α1-antitrypsin is a single polypeptide chain with no internal disulfide bonds and only a single cysteine residue normally intermolecularly disulfide-linked to either cysteine or glutathione. The reactive site of α1-antitrypsin contains a methionine residue, which is labile to oxidation upon exposure to tobacco smoke or other oxidizing pollutants. Such oxidation reduces the elastase-inhibiting activity of α1-antitrypsin; therefore substitution of another amino acid at that position, i.e. alanine, valine, glycine, phenylalanine, arginine or lysine, produces a form of α1-antitrypsin which is more stable. α1-antitrypsin can be represented by the following formula: SEQ ID 61:

```
MPSSVSWGIL LAGLCCLVPV SLAEDPQGDA AQKTDTSHHD    100

QDHPTFNKITPNLAEFAFSL YRQLAHQSNS TNIFFSPVSI

ATAFAMLSLG TKADTHDEIL

EGLNFNLTEI PEAQIHEGFQ ELLRTLNQPD SQLQLTTGNG    200

LFLSEGLKLVDKFLEDVKKL YHSEAFTVNF GDHEEAKKQI

NDYVEKGTQG KIVDLVKELD

RDTVFALVNY IFFKGKWERP FEVKDTEDED FHVDQVTTVK    300

VPMMKRLGMF NIQHCKKLSS WVLLMKYLGN ATAIFFLPDE

GKLQHLENEL THDIITKFLE

NEDRRSASLH LPKLSITGTY DLKSVLGQLG ITKVFSNGAD    400

LSGVTEEAPL KLSKAVHKAV LTIDEKGTEA AGAMFLEAIP

MSIPPEVKFN KPFVFLMIEQ

NTKSPLFMGK VVNPTQK                             417
```

One important amino acid sequence near the carboxyterminal end of α1-antitrypsin is shown in bold and underlined and is pertinent to this invention (details of the sequence can be found for example in U.S. Pat. No. 5,470,970, as incorporated by reference).

Extrahepatic sites of AAT production include neutrophils, monocytes and macrophages, and the expression of AAT is inducible in response to LPS, TNFα, IL-1 and IL-6 in various cell types. Deficiency in AAT is associated with immune dysfunctional conditions such as rheumatoid arthritis and systemic lupus erythematosus.

Other serine protease inhibitor molecules, which may be used in any of the disclosed compositions may include compounds disclosed in the following: WO 98/20034 disclosing serine protease inhibitors from fleas; WO98/23565 disclosing aminoguanidine and alkoxyguanidine compounds useful for inhibiting serine proteases; WO98/50342 disclosing bis-aminomethylcarbonyl compounds useful for treating cysteine and serine protease disorders; WO98/50420 cyclic and other amino acid derivatives useful for thrombin-related diseases; WO 97/21690 disclosing D-amino acid containing derivatives; WO 97/10231 disclosing ketomethylene group-containing inhibitors of serine and cysteine proteases; WO 97/03679 disclosing phosphorous containing inhibitors of serine and cysteine proteases; WO 98/21186 benzothiazo and related heterocyclic inhibitors of serine proteases; WO 98/22619 disclosing a combination of inhibitors binding to P site of serine proteases with chelating site of divalent cations; WO 98/22098 disclosing a composition which inhibits conversion of pro-enzyme CPP32 subfamily including caspase 3 (CPP32/Yama/Apopain); WO 97/48706 disclosing pyrrolo-pyrazine-diones; and WO 97/33996 disclosing human placental bikunin (recombinant) as serine protease inhibitor.

Other compounds having serine protease inhibitory activity are equally suitable and effective for use in the methods of the present invention, including but not limited to: tetrazole derivatives as disclosed in WO 97/24339; guanidinobenzoic acid derivatives as disclosed in WO 97/37969 and in a number of U.S. Pat. Nos. 4,283,418; 4,843,094; 4,310,533; 4,283,418; 4,224,342; 4,021,472; 5,376,655; 5,247,084; and 5,077,428; phenylsulfonylamide derivatives represented by general formula in WO 97/45402; novel sulfide, sulfoxide and sulfone derivatives represented by general formula in WO 97/49679; novel amidino derivatives represented by general formula in WO 99/41231; other amidinophenol derivatives as disclosed in U.S. Pat. Nos. 5,432,178; 5,622,984; 5,614,555; 5,514,713; 5,110,602; 5,004,612; and 4,889,723 among many others.

Graft Rejection and Graft Survival-Side-Effects and Conditions

One of the beneficial effects of use of the compositions and methods of the present invention include, for example, and not by way of limitation, reduced infiltration of graft with cells or serum factors (including but not limited to, complement, anti graft antibody that generate inflammation and graft rejection), reduced cytokines, reduced nitric oxide, reduced apoptosis, and reduced specific immune response against the graft or any combination thereof.

Management of Graft Rejection

By preventing or reducing the side effects or conditions associated with graft survival or graft rejection using this novel approach, several advantages are obtained compared to alternative approaches, for example, and not by way of limitation:

1. Reduced infiltration of graft with cells or serum factors (for example, and not by way of limitation, complement, anti graft antibody that generate inflammation and graft rejection); reduced production of cytokines or nitric oxide (NO)

that can induce inflammation or apoptosis; inhibits apoptosis; inhibits immune activation, inhibits CMV or any combination thereof.

2. Synthetic inhibitors of serine proteases (AAT-like mimics or analogs) can and have been developed by means known in the art. Such a pharmaceutical agent may be formulated as for example, a cream to treat graft rejection and/or promote graft survival.

3. Commercially available agents already approved for different use in humans will work as a treatment for graft rejection and/or promote graft survival. These agents are currently used for indications other than graft rejection and/or to promote graft survival, and include injectible AAT, plasma preparations, aprotinin and others (American J. of Resp Critical Care Med 1998, Vll 158: 49-59, incorporated herein by reference in its entirety). In one embodiment, serine protease inhibitors may be delivered by inhalation. An inhaled agent (natural AAT or a synthetic AAT-like mimic/or other inhibitor of serine protease) may be especially useful due to elevated local concentrations, ease of drug delivery, and lack of side effects (since administration is not systemic). This mode of focused drug delivery may augment serine protease inhibitor activity within the lung tissues and associated lymphatics, which are two of the principal sites where diseases and/or clinical conditions associated with graft rejection and/or promotion of graft survival develop.

4. By promoting graft survival and/or treating graft rejection, the direct cause of the side effect is disrupted in affected individuals. This invention specifically contemplates inhibiting host cell serine proteases or induce the SEC receptor or combination thereof as a method of treating graft rejection and/or promoting graft survival in a mammal in need thereof in conjunction with administration of one or more anti-rejection and/or anti-microbial.

5. There is an extensive clinical experience using injectible AAT to treat patients with genetic AAT deficiency. No long-term negative effects have been detected to date (American J. of Resp Critical Care Med 1998, Vll 158: 49-59; Wencker et al. Chest 2001 119:737-744). Moreover, a small molecule inhibitor of host serine protease has been administered to patients with Kawasaki's Disease (Ulinistatin, Ono pharmaceuticals).

Isolated Proteins for Use in the Compositions and Methods of the Invention

One aspect of the invention pertains to proteins, and portions thereof, as well as polypeptide fragments suitable for use as immunogens to raise antibodies directed against a polypeptide of the invention. In one embodiment, the native polypeptide can be isolated from cells or tissue sources by an appropriate purification scheme using standard protein purification techniques. In another embodiment, polypeptides of the invention are produced by recombinant DNA techniques. Alternative to recombinant expression, a polypeptide of the invention can be synthesized chemically using standard peptide synthesis techniques.

Recombinant unmodified and mutant variants of .alpha..sub.1-antitrypsin produced by genetic engineering methods are also known (see U.S. Pat. No. 4,711,848). The nucleotide sequence of human alpha.sub.1-antitrypsin and other human alpha.sub.1-antitrypsin variants has been disclosed in international published application No. WO 86/00,337, the entire contents of which are incorporated herein by reference. This nucleotide sequence may be used as starting material to generate all of the AAT amino acid variants and amino acid fragments depicted herein, using recombinant DNA techniques and methods known to those of skill in the art.

An isolated and/or purified or partially purified protein or biologically active portion thereof may be used in any embodiment of the invention. A protein that is substantially free of cellular material includes preparations of protein having less than about 30%, 20%, 10%, or 5% (by dry weight) of heterologous protein. When the protein or biologically active portion thereof is recombinantly produced, it can also be substantially free of culture medium. When the protein is produced by chemical synthesis, it is preferably substantially free of chemical precursors or other chemicals. Accordingly, such preparations of the protein have less than about 30%, 20%, 10%, and 5% (by dry weight) of chemical precursors or compounds other than the polypeptide of interest.

Biologically active portions of a polypeptide of the invention include polypeptides including amino acid sequences sufficiently identical to or derived from the amino acid sequence of the protein (e.g., the amino acid sequence shown in any of SEQ ID Nos: 1 to 60, which exhibit at least one activity of the corresponding full-length protein). A biologically active portion of a protein of the invention can be a polypeptide, which is, for example, 5, 10, 25, 50, 100 or more amino acids in length. Moreover, other biologically active portions, in which other regions of the protein are deleted, can be prepared by recombinant techniques and evaluated for one or more of the functional activities of the native form of a polypeptide of the invention.

Preferred polypeptides have the amino acid sequence of SEQ ID Nos: 1 to 60. Other useful proteins are substantially identical (e.g., at least about 45%, preferably 55%, 65%, 75%, 85%, 95%, or 99%) to any of SEQ ID NOs: 1 to 60, and retain the functional activity of the protein of the corresponding naturally-occurring protein yet differ in amino acid sequence due to natural allelic variation or mutagenesis.

The compounds of the present invention can be used as therapeutic agents in the treatment of a physiological (especially pathological) condition caused in whole or part, by excessive serine protease activity. In addition, a physiological (especially pathological) condition can be inhibited in whole or part. Peptides contemplated herein may be administered as free peptides or pharmaceutically acceptable salts thereof. The peptides should be administered to individuals as a pharmaceutical composition, which, in most cases, will include the peptide and/or pharmaceutical salts thereof with a pharmaceutically acceptable carrier.

When utilizing BLAST, Gapped BLAST, and PSI-Blast programs, the default parameters of the respective programs (e.g., XBLAST and NBLAST) can be used.

The present invention also pertains to variants of the polypeptides of the invention. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a protein of the invention which function as either agonists (mimetics) or as antagonists can be identified by screening combinatorial libraries of mutants, e.g., truncation mutants, of the protein of the invention for agonist or antagonist activity.

Fusion Polypeptides

In other embodiments, compounds having serine protease inhibitor activity such as α1-antitrypsin and/or analog thereof, may be part of a fusion polypeptide. In one example, a fusion polypeptide may include α1-antitrypsin (e.g. mammalian α1-antitrypsin) or an analog thereof and a different amino acid sequence that may be heterologous to the α1-antitrypsin or analog substance.

In yet other embodiments, the fusion polypeptide contemplated for use in the methods of the present invention can additionally include an amino acid sequence that is useful for identifying, tracking or purifying the fusion polypeptide, e.g., a FLAG or HIS tag sequence. The fusion polypeptide can include a proteolytic cleavage site that can remove the heterologous amino acid sequence from the compound capable of serine protease inhibition, such as mammalian α1-antitrypsin or analog thereof.

In one embodiment, fusion polypeptides of the invention are produced by recombinant DNA techniques. Alternative to recombinant expression, a fusion polypeptide of the invention can be synthesized chemically using standard peptide synthesis techniques. The present invention also provides compositions that comprise a fusion polypeptide of the invention and a pharmaceutically acceptable carrier, excipient or diluent.

In particular, in one embodiment the fusion protein comprises a heterologous sequence that is a sequence derived from a member of the immunoglobulin protein family, for example, comprise an immunoglobulin constant region, e.g., a human immunoglobulin constant region such as a human IgG1 constant region. The fusion protein can, for example, include a portion of α1-antitrypsin, analog thereof or inhibitor of serine protease activity polypeptide fused with the amino-terminus or the carboxyl-terminus of an immunoglobulin constant region, as disclosed, e.g., in U.S. Pat. No. 5,714,147, and U.S. Pat. No. 5,116,964. In accordance with these embodiments, the FcR region of the immunoglobulin may be either wild-type or mutated. In certain embodiments, it is desirable to utilize an immunoglobulin fusion protein that does not interact with an Fc receptor and does not initiate ADCC reactions. In such instances, the immunoglobulin heterologous sequence of the fusion protein can be mutated to inhibit such reactions. See, e.g., U.S. Pat. No. 5,985,279 and WO 98/06248.

In yet another embodiment, α1-antitrypsin, analog thereof, or inhibitor of serine protease activity polypeptide fusion protein comprises a GST fusion protein in which is fused to the C-terminus of GST sequences. Fusion expression vectors and purification and detection means are known in the art.

Expression vectors can routinely be designed for expression of a fusion polypeptide of the invention in prokaryotic (e.g., E. coli) or eukaryotic cells (e.g., insect cells (using baculovirus expression vectors), yeast cells or mammalian cells) by means known in the art.

Expression of proteins in prokaryotes may be carried out by means known in the art. Such fusion vectors typically serve three purposes: 1) to increase expression of recombinant protein; 2) to increase the solubility of the recombinant protein; and 3) to aid in the purification of the recombinant protein by acting as a ligand in affinity purification.

In yet another embodiment, a nucleic acid of the invention is expressed in mammalian cells using a mammalian expression vector as described in the art. In another embodiment, the recombinant mammalian expression vector is capable of directing expression of the nucleic acid preferentially in a particular cell type (e.g., tissue-specific regulatory elements are used to express the nucleic acid) such as pancreas-specific promoters (Edlund et al. (1985) Science 230:912-916), and mammary gland-specific promoters (e.g., milk whey promoter; U.S. Pat. No. 4,873,316 and European Application Publication No. 264,166). A host cell can be any prokaryotic (e.g., E. coli) or eukaryotic cell (e.g., insect cells, yeast or mammalian cells). Vector DNA can be introduced into prokaryotic or eukaryotic cells via conventional transformation or transfection techniques.

Combination Therapies

In each of the aforementioned methods of the present invention, the use of a compound capable of inhibiting serine protease or α1-antitrypsin or analog thereof alone or in combination with standard immunosuppressive agents enables transplantation of grafts into immunosuppressed or immunocompromised recipients. This combination therapy will expand the eligible patient population able to receive this form of treatment.

In each of the aforementioned aspects and embodiments of the invention, combination therapies other than those already enumerated above are also specifically contemplated herein. In particular, the compositions of the present invention may be administered with one or more macrolide or non-macrolide antibiotics, anti-bacterial agents, anti-fungals, anti-viral agents, and anti-parasitic agents. Examples of macrolide antibiotics that may be used in combination with the composition of the present invention include but are not limited to synthetic, semi-synthetic or naturally occurring macrolidic antibiotic compounds: methymycin, neomethymycin, YC-17, litorin, TMP-SSX, erythromycin A to F, and oleandomycin. Examples of preferred erythromycin and erythromycin-like compounds include: erythromycin, clarithromycin, azithromycin, and troleandomycin.

Examples of anti-bacterial agents include, but are not limited to, penicillins, quinolonses, aminoglycosides, vancomycin, monobactams, cephalosporins, carbacephems, cephamycins, carbapenems, and monobactams and their various salts, acids, bases, and other derivatives.

Anti-fungal agents include, but are not limited to, caspofungin, terbinafine hydrochloride, nystatin, and selenium sulfide.

Anti-viral agents include, but are not limited to, gancyclovir, acyclovir, valacylocir, amantadine hydrochloride, rimantadin and edoxudine Examples of macrolide antibiotics that may be used in combination with the composition of the present invention include but are not limited to synthetic, semi-synthetic or naturally occurring macrolidic antibiotic compounds: methymycin, neomethymycin, YC-17, litorin, TMP-SSX, erythromycin A to F, and oleandomycin. Examples of preferred erythromycin and erythromycin-like compounds include: erythromycin, clarithromycin, azithromycin, and troleandomycin.

Anti-parasitic agents include, but are not limited to, pirethrins/piperonyl butoxide, permethrin, iodoquinol, metronidazole, co-trimoxazole (sulfamethoxazole/trimethoprim), and pentamidine isethionate.

In another aspect, in the method of the present invention, one may, for example, supplement the composition by administration of a therapeutically effective amount of one or more an anti-inflammatory or immunomodulatory drugs or agents. By "anti-inflammatory drugs", it is meant, e.g., agents which treat inflammatory responses, i.e., a tissue reaction to injury, e.g., agents which treat the immune, vascular, or lymphatic systems.

Anti-inflammatory or immunomodulatory drugs or agents suitable for use in this invention include, but are not limited to, interferon derivatives, (e.g., betaseron); prostane derivatives, (e.g., compounds disclosed in PCT/DE93/0013, iloprost, cortisol, dexamethasone; immunsuppressives, (e.g., cyclosporine A, FK-506 (mycophenylate mofetil); lipoxygenase inhibitors, (e.g., zileuton, MK-886, WY-50295); leukotriene antagonists, (e.g., compounds disclosed in DE 40091171 German patent application P 42 42 390.2); and analogs; peptide derivatives, (e.g., ACTH and analogs); soluble TNF-receptors; TNF-antibodies; soluble receptors of interleukins, other cytokines, T-cell-proteins; antibodies against receptors of interleukins, other cytokines, and T-cell-proteins.

Kits

In still further embodiments, the present invention concerns kits for use with the methods described above. Small molecules, proteins or peptides may be employed for use in any of the disclosed methods. In addition, other agents such as anti-bacterial agents, immunosuppressive agents, anti-inflammatory agents may be provided in the kit. The kits will thus can include, in suitable container means, a protein or a peptide or analog agent, and optionally one or more additional agents.

The kits may further include a suitably aliquoted composition of the encoded protein or polypeptide antigen, whether labeled or unlabeled, as may be used to prepare a standard curve for a detection assay.

The container means of the kits will generally include at least one vial, test tube, flask, bottle, syringe or other container means, into which the antibody or antigen may be placed, and preferably, suitably aliquoted. Where a second or third binding ligand or additional component is provided, the kit will also generally contain a second, third or other additional container into which this ligand or component may be placed. The kits of the present invention will also typically include a means for containing the antibody, antigen, and any other reagent containers in close confinement for commercial sale. Such containers may include injection or blow-molded plastic containers into which the desired vials are retained.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Alpha-1-Antitrypsin Prolongs Graft Islet Graft Survival in Mice

FIG. 1A-1D. Islets from DBA/2 mice (H-2d) were transplanted under the renal capsule of streptozotocin-induced hyperglycemic C57BL/6 mice (H-2b). (A) Glucose levels from days 6-18. Control consists of mice that were untreated (n=3) or treated from day −1 every 3 days with human albumin (ALB, 6 mg, n=3). Prolonged islet graft survival is observed in mice treated from day −1 every 3 days with human AAT (2 mg, n=10). * $P<0.05$,  $P<0.01$, * $P<0.001$ between glucose levels on same day. (B) Treatment protocols. Control and full AAT treatment are described in panel A. Early AAT treatment consists of treatment on days −1, 1 and 3 (2 mg, n=3). Late AAT treatment consists of treatment from day 2 and on every 2 days (2 mg, n=3). Rejection indicates the day that glucose levels exceed 300 mg/dl. (C) Effect of mouse anti-human-AAT antibodies. Dashed line indicates post transplantation glucose levels of a mouse under full AAT treatment protocol (see A, B) that was immunized by multiple administrations of human AAT prior to transplantation (1 representative, n=3). Solid line indicates glucose levels of a non-immunized mouse treated under full AAT treatment protocol (1 representative, n=10). Arrow indicates detection of treatment-induced, anti-human-AAT antibodies in the non-immunized representative mouse. (D) Comparison of day 15 post-transplantation glucose levels in mice that were under full treatment protocol with ALB (n=3) or AAT (non-immunized n=10, immunized n=3). Of the AAT-treated group, antibodies were detected on day 15 in 3/3 immunized mice and in 6/10 non-immunized mice. ** $P=0.005$ between mice that produced antibodies (n=6) and mice that did not produce antibodies (n=4).

Figure 1B:
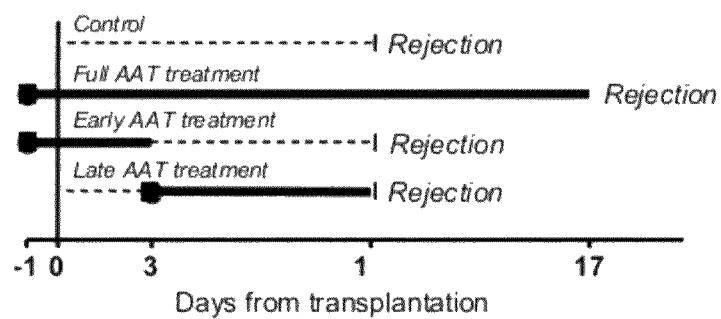

Treatment with human albumin (6 mg) resulted in graft rejection comparable to that of untreated recipient mice. In contrast, recipient mice that received AAT (2 mg) exhibited prolonged graft function. As depicted in FIG. 1b, neither of the partial treatment protocols, i.e., days −1, 1 and 3 ('early treatment') or days 2 and beyond ('late treatment') prolonged allograft survival.

Figure 1C:
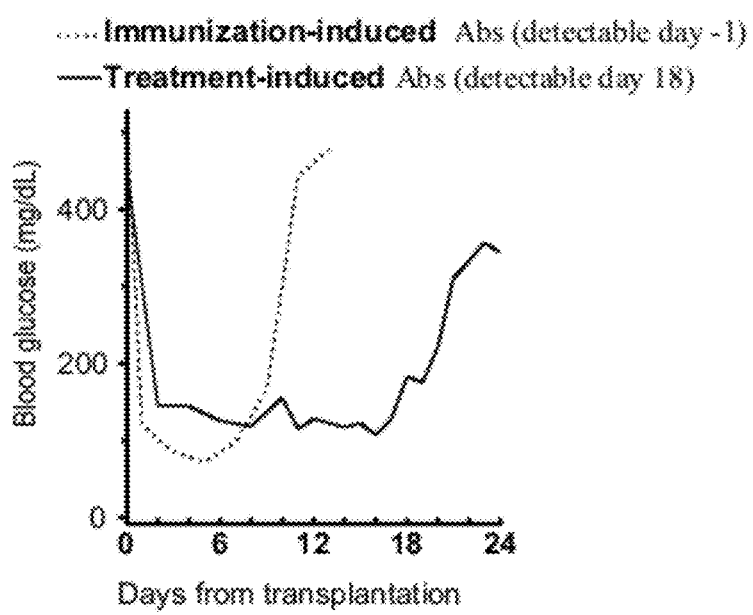
Figure 1D:
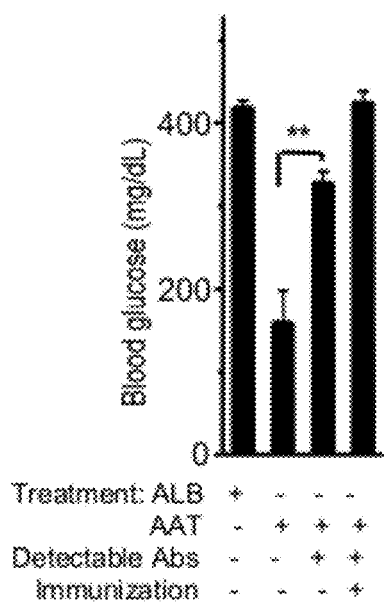

AAT-treated mice developed anti-human-AAT antibodies (FIGS. 1C and D). Individual mice exhibited anti-human-AAT antibodies at various time points (data not shown). To ascertain that the antibodies reduce the protective effect of AAT, a group of mice was pre-exposed ("immunized") to human AAT two months before being rendered hyperglycemic and transplanted with allogeneic islets. These graft recipients were treated with the full AAT protocol, despite exhibiting high titers of specific antibodies before engraftment, and displayed rapid graft rejection (FIG. 1C). Day 15 was chosen to depict an association between antibody formation and loss of AAT protective activity; at this time point AAT-treated mice were divided into positive and negative producers of anti-human-AAT antibodies. As shown in FIG. 1D, on day 15 all antibody-positive mice were hyperglycemic and all antibody-negative mice were normoglycemic.

Example 2

Figures 2A, 2B, 2C, 2D:
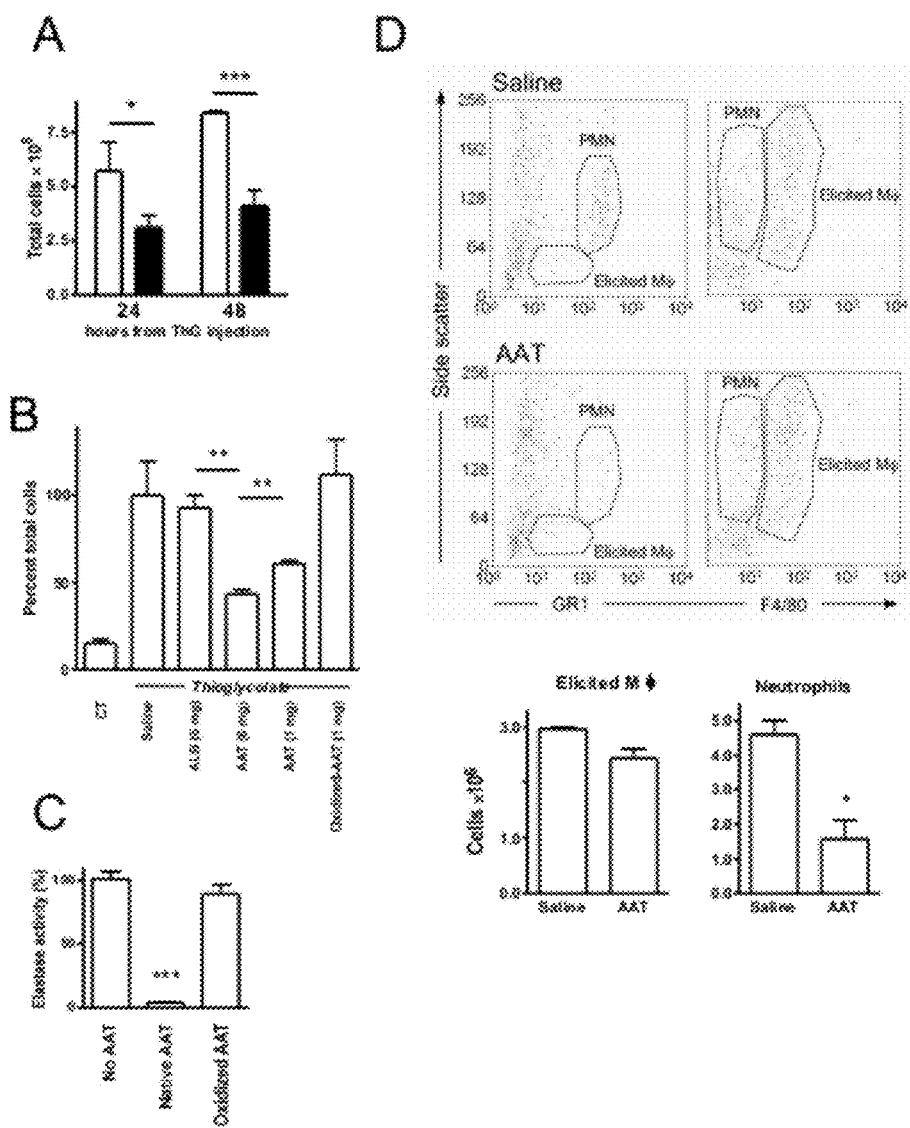
FIGS. 2A-2D illustrates an exemplary method of the effect of AAT on thioglycolate-elicited peritoneal cellular infiltrates. (A) Total cell population of lavaged cells of (o) saline or ( ) AAT-treated ($5^\Delta$ mg) thioglycolate-injected mice. (B) Percent cell population from saline-treated mice at 48 hours. (C) Oxidation of AAT. (D) Identification of elicited macrophages and neutrophils.

FIG. 2A-2D illustrates an exemplary method of the effect of AAT on thioglycolate-elicited peritoneal cellular infiltrates. Mice were administered intraperitoneal 0.1 ml saline, ALB, AAT or oxidized-AAT followed by 1 ml of saline or thioglycolate (ThG, 3% w/v, n=3 per group). Peritoneal lavage was performed on separate groups after 24 and 48 hours. (A) Total cell population of lavaged cells of (open bars) saline or (closed bars) AAT-treated (5 mg) thioglycolate-injected mice.  $P<0.05$. (B) Percent cell population from saline-treated mice at 48 hours.  $P<0.05$. (C) Oxidation of AAT. AAT was subjected to oxidative radicals (see Methods). Loss of serine protease activity of oxidized AAT was assessed in an elastase assay. Activity of elastase in the absence of native AAT was set at 100% and the percentage of activity in the presence of native and oxidized AAT was calculated (n=3). *** P<0.001. In FIG. 2D, elicited macrophages and neutrophils are identified. Peritoneal infiltrates from 48 hour lavages of ALB (6 mg) and AAT-treated (6 mg), thioglycolate-injected mice were stained for FACS analysis by specific antibodies. Macrophages and neutrophils were identified on the basis of F4/80 and GR1 versus side scatter flow cytometry profiles. Top, FACS analysis representative graphs (n=3). Quantified FACS results (n=3) are depicted in the bottom.

AAT Inhibits Cellular Infiltration

To address the possibility that AAT affects effector cell infiltration, two models of cell emigration were examined: thioglycolate (ThG)-elicited peritoneal infiltration, and cellular infiltration due to intraperitoneal injection of MHC-incompatible fibroblasts.

As shown in FIG. 2A, there was a progressive increase in total cell count at 24 and 48 hours in mice injected with ThG, whereas no significant increase was observed in mice injected with AAT and ThG. At 48 hours, total cell count in peritoneal lavage of AAT-treated mice was 50% of that of control (FIG. 2B). Total cell count in mice that received albumin control was similar to that of saline-treated mice. There was a dose-dependent effect of AAT in that one-sixth the dose was found to reduce cell count to a lesser extent in a significant manner. Oxidized AAT, which had lost its in vitro anti-elastase activity (FIG. 2C), did not affect cellular infiltrate at 1 mg (FIG. 2B).

The decrease in total cell count is primarily attributed to a decrease in the number of neutrophils (FIG. 2D), identified by their GR-1high/intermediate side-scatter (SSC) profile. No major difference was observed with the infiltration of macrophages, identified by their F4/80int, GR-1int, intermediate SSC profile[12], which is distinct from the F4/80 very high, GR-1low, high SSC profile of resident macrophages[12] (data not shown).

Example 3

Figure 3A:
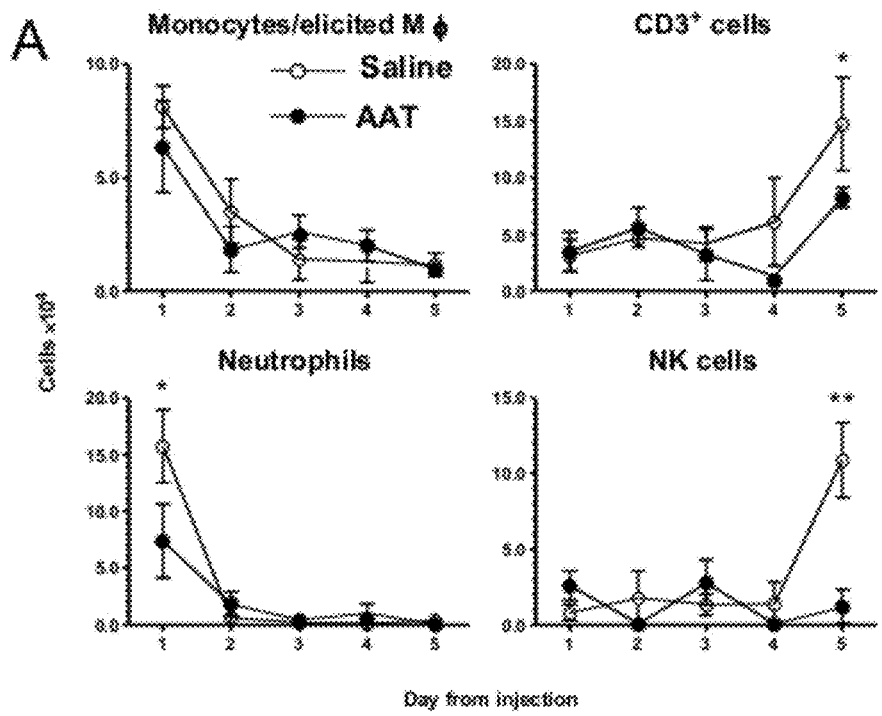
Figure 3B:
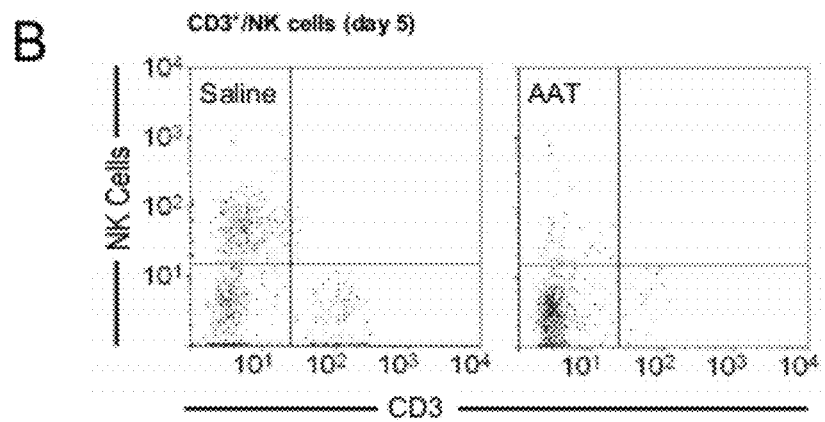

FIG. 3A-3C illustrates an exemplary method of the effect of AAT on MHC-incompatible, NIH-3T3-fibroblast-elicited peritoneal cellular infiltrates. Mice (C57BL/6; H-2b) were injected i.p. 0.1 ml saline or AAT (1 mg) followed by 1 ml NIH-3T3 cells (1'107 cells in saline; H-2d). Peritoneal lavage was performed daily on days 1-5 and cell subpopulations were identified by FACS analysis. (n=3 per treatment). (A) Cell numbers. The number of cells in each subpopulation was calculated from the percentages obtained by FACS analysis, and total number of cells in the infiltrate. * P<0.05, ** P<0.01 between cell numbers on the same day. (B) Representative FACS analysis. (C) Effect of AAT on intensity and function of infiltrate elicited by islet allograft. Left, Hematoxilyn and Eosin (H&E) staining of day 7 islet allografts. A section of AAT-treated islet graft (white frame) is compared to a similar section of ALB-treated diabetic recipient mouse (full treatment protocol, see FIG. 1A). Arrow points at border between islet and surrounding infiltrate. Right, Immunohistochemistry (IHC) with anti-insulin antibodies of day 15 islet grafts. A section of autologous islet graft (white frame) is compared to similar sections of allografts of AAT- and ALB-treated recipient mice. R, renal parenchyma, G, graft, C, renal capsule.

As illustrated in FIG. 3A, introduction of allogeneic cells evoked a cellular infiltrate that consisted of early appearing neutrophils and activated macrophages, and late appearing CD3+ and NK cells (FIG. 3B). AAT-treated mice exhibited a reduction in neutrophils, CD3+ and NK cells, dark color is insulin staining.

To evaluate the level of cellular infiltration into grafted islets, grafts from AAT- and ALB-treated recipient mice were removed on day 7, fixed in paraformaldehyde and stained with Hematoxilin and Eosin. As depicted in FIG. 3C (left), a cellular infiltrate is demonstrable regardless of AAT treatment, and includes neutrophils and lymphocytes. However, the infiltrates evoked by grafts of ALB-treated recipient mice were more massive and cause the disruption of islet borders, compared to intact islets of AAT-treated recipient mice. To evaluate islet function, grafts from AAT- and ALB-treated recipient mice were removed on day 15, and immunohistochemistry was performed with anti-insulin antibodies, dark color is insulin staining. As depicted in FIG. 3C (right), insulin production is preserved on day 15 in islets of AAT-treated recipients.

Example 4

FIG. 4A-4H illustrates an exemplary method of the effect of AAT on islet responses. (A-D) Islets from C57BL/6 mice were cultured at 100 islets/well, in duplicate. AAT was incubated at the indicated concentrations for 1 hour before the addition of IFNγ (5 ng/ml) plus IL-1β (10 ng/ml). 72 hours later, supernatants were collected and islet viability was assessed. Islet cells responses in the absence of AAT were set at 100%. Data are combined from 3 individual experiments, in duplicate.  P<0.01, * P<0.001 between AAT-treated and untreated islets. Mean±SEM of a. nitrite levels, b. Cell viability and c. MIP-1α levels. Dashed line represents islets incubated at one-30th the concentration of IFNγ/IL-1β. d. TNFα levels. (E) Insulin induction assay. Islets were incubated in triplicate (20 islets/well) in the presence of AAT (0.5 mg/ml) or ALB (0.5 mg/ml) 1 hour before addition of IFNγ (5 ng/ml) plus IL-1β (10 ng/ml). 24 hours later, islets were transferred to a 3 mM or 20 mM glucose solution for 30 minutes and insulin levels were measured. Vertical axis depicts the ratio between insulin levels at both glucose concentrations. * P<0.05 between AAT-treated and ALB-treated islets. (F) Streptozotocin toxicity. C57BL/6 mice were injected i.p. with AAT (5 mg) or saline, one day before, on same day and one day after injection of streptozotocin (225 mg/kg) or saline (n=3 per group). 48 hours later, pancreata were removed and insulin-containing cells were identified by immunohistochemistry. Each image depicts a representative islet form one pancreas. Graph, mean±SEM percent change of insulin-containing cells as determined manually from images of 2 islets per pancreas (n=6 per treatment group). * P<0.05. (G) Cellular content of islets. Freshly isolated islets (100 islets in triplicate) and residual non-islet pancreatic debris were dissociated into single cell suspensions and stained for FACS analysis with anti-CD45-APC or isotype control antibody. Shaded area, islets. Open area, debris. (H) MHC class II expression. Islets from C57BL/6 mice were cultured (100 islets/well in duplicate) in the presence of AAT (0.5 mg/ml) 1 hour before the addition of IFNγ (5 ng/ml) plus IL-1β (10 ng/ml). 24 hours later, islets were dissociated into single cell suspensions and double-stained for FACS analysis with anti-CD45-APC and anti-MHCII-PE, or isotype control antibodies. Left, Mean±SEM percent change from control (CT) unstimulated islets. * P<0.05 between AAT-treated and untreated islets. Right, Representative FACS analysis; Shaded area, AAT-treated islets. Open area, stimulated islets. Events are gated for CD45+.

AAT Modifies Islet Response to Proinflammatory Mediators

Figure 4C:
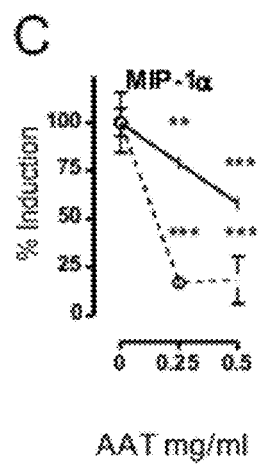
Figure 4D:
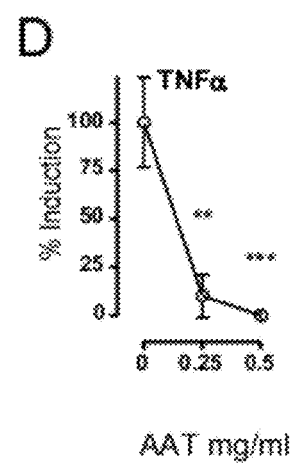
Figure 4E:
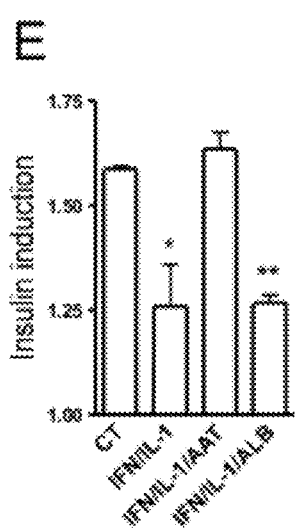
Figure 4F:
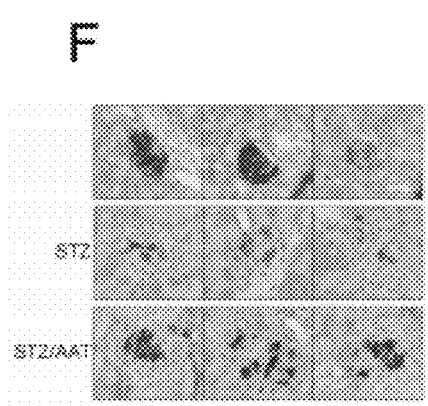
Figure 4G:
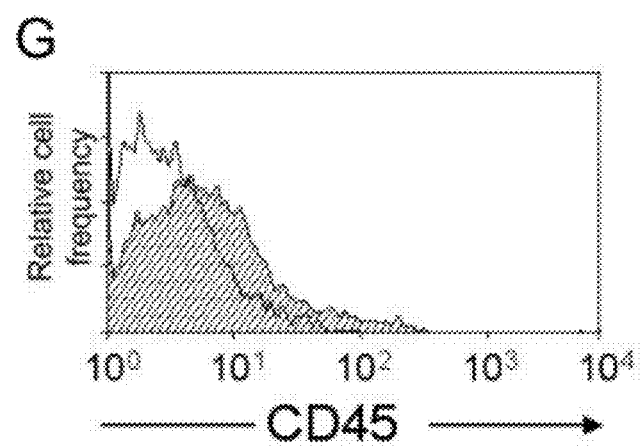
Figure 4H:
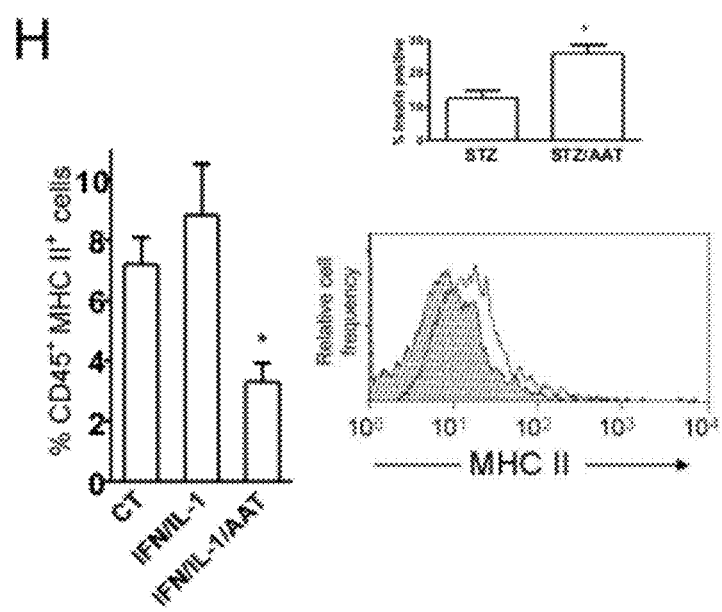

Various islet responses to IL-1β/IFNγ were examined in vitro. Islets exposed to IL-IL-1β/IFNγ for 72 hours produce nitric oxide (NO) in a concentration-dependent manner and exhibit NO-dependent loss of viability. As shown in FIGS. 4A and B, in the presence of AAT, less NO was produced and greater islet viability was obtained. The production of MIP-1α was decreased in the presence of AAT, particularly when stimulated by low concentrations of IL-1β/IFNγ (FIG. 4C). Notably, TNFα level in supernatants was markedly diminished by AAT (FIG. 4D). Insulin induction was inhibited by IL-1β/IFNγ, but was intact in the presence of IL-1β/IFNγ plus AAT (FIG. 4E). To test the effect of AAT on islets in vivo, STZ toxicity was evaluated. AAT (2 mg) was administered one day before, on the same day and a day after STZ injection. Immunohistochemistry of pancreata with anti-insulin antibodies at 48 hours after STZ injection reveals more insulin-producing cells in islets of AAT- than ALB-treated mice (26.3%±2.6 and 12.8%±2.3 insulin-producing cells per islet, respectively, FIG. 4*f*). White cell content of freshly isolated islets was evaluated by FACS analysis. Islets contain CD45+ cells (FIG. 4G) that are also positive for the monocytic/granulocytic markers GR1 and F4/80 (data not shown). This cell population responded to AAT with decreased surface MHC class II (FIG. 4H).

Example 5

FIG. 5A-5D illustrates the effect of AAT on TNFα. (A) Islets from C57BL/6 mice were cultured (100 islets/well in triplicate) in the presence of AAT (0.5 mg/ml) or TACE inhibitor (10 mM) 1 hour before stimulation by IFNγ (5 ng/ml) plus IL-1β (10 ng/ml). Left, mean±SEM change in TNFα in supernatants after 72 hours of incubation. Right, mean±SEM fold change in membrane TNFα on islet cells after 5 hours of incubation, according to FACS analysis. *** $P<0.001$ compared control (CT) levels in the absence of AAT. (B) Representative FACS analysis of membrane TNFα on stimulated islet cells in the absence (open area) or presence (shaded area) of AAT. Events are gated for CD45+. (C) Streptozotocin-induced hyperglycemia. C57BL/6 mice were injected i.p. with saline (n=3), AAT (5 mg, n=3) or TNFα (1 mg/kg, n=3) or administered p.o. with TACE inhibitor (TACEi, 60 mg/kg, n=6) one day before injection of STZ (225 mg/kg, i.p.). Subsequently, AAT and TNFα were injected daily; TACE inhibitor was administered twice a day. At 48 hours, mean±SEM glucose levels are compared to those of normal littermates (n=3). * $P<0.05$, ** $P<0.01$ compared to saline-treated, STZ-injected mice.

AAT Inhibits Release of Membrane TNFα

Figures 5A, 5B:
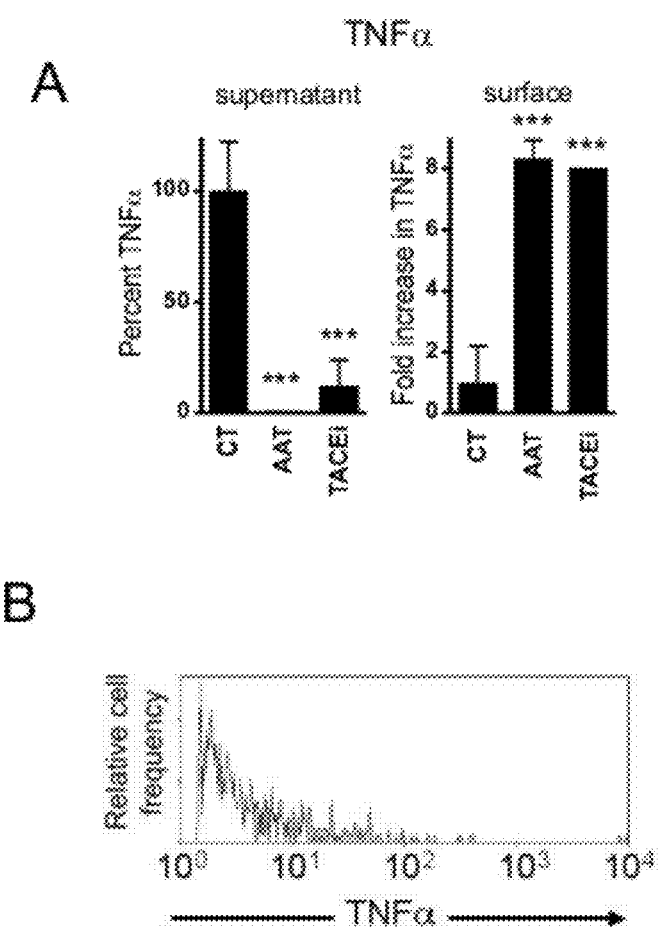
FIGS. 5A-5D illustrates the effect of AAT on TNFα. (A) Islets from C57BL/6 mice were cultured (100 islets/well in triplicate) in the presence of AAT (0.5 mg/ml) or TACE inhibitor (10 mM) 1 hour before stimulation by IFNγ (5 ng/ml) plus IL-1β (10 ng/ml). Left, mean±SEM change in TNFα in supernatants after 72 hours of incubation. Right, mean±SEM fold change in membrane TNFα on islet cells after 5 hours of incubation, according to FACS analysis. (B) Representative FACS analysis of membrane TNFα on stimulated islet cells in the absence (open area) or presence (shaded area) of AAT. (C) Streptozotocin-induced hyperglycemia.

Proteolytic cleavage of membrane TNFα releases soluble TNFα from activated cells by the action of TNFα-converting-enzyme (TACE). The inventors examined the levels of membrane TNFα on stimulated islets in the presence of AAT. The effect of AAT was compared to that of a TACE inhibitor. Both AAT and TACE inhibitor decreased TNFα levels in supernatants of islets exposed to IL-1β/IFNγ (FIG. 5A, left). Under these conditions, membrane TNFα accumulated on the cell surface of CD45+ islet cells (FIG. 5A, right).

Figure 5C:
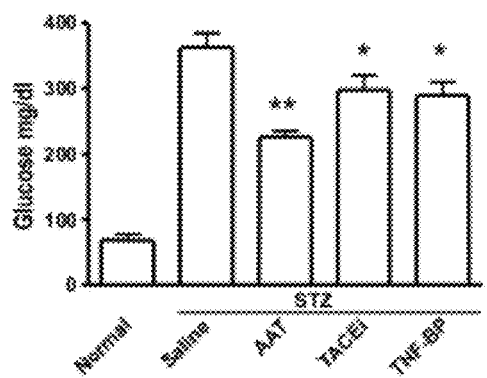

To assess the possibility that islet protection occurs via inhibition of release of membrane TNFα in vivo, TACE inhibitor, p75 TNF receptor (TNF BP) or AAT were introduced to mice prior to STZ injection. Although all mice developed hyperglycemia after day 4, the progression of β-cell toxicity was significantly affected by treatments. As shown in FIG. 5C, the effect of STZ at 48 hours was decreased in the presence of AAT (a decrease of 23.2%±2.3 in fasting glucose levels compared to STZ/saline injected mice). The effect of TACE inhibitor and p75 TNF receptor was not as profound. Similarly, TACE inhibitor prolonged islet graft survival to a lesser extent than AAT (preliminary data not shown).

Figure 5D:
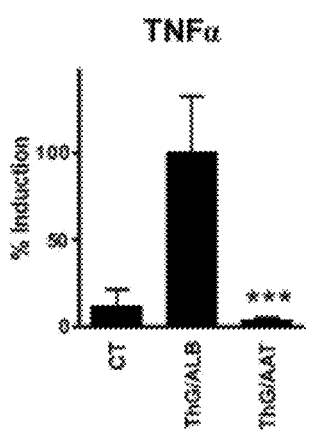
Figure 8C:
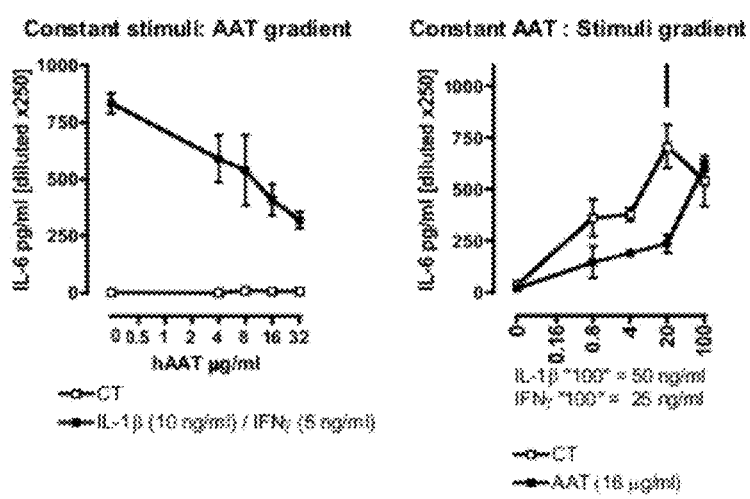
Figure 8D:
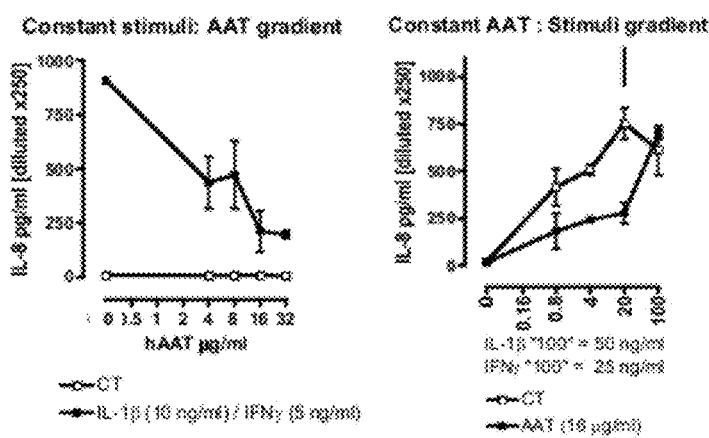

Splenocytes that were harvested 48 hours after ThG injection produced TNFα in culture (FIG. 5D). AAT administered prior to thioglycolate decreased TNFα release from cultured splenocytes. A similar trend was found with IFNγ (data not shown), signifying that the response to ThG had effects that extend beyond the peritoneal compartment and that pretreatment with AAT reduced these effects.

Example 6

FIG. 6A-6D illustrates the effect of AAT on Islet allograft transplantation. 6A illustrates the time course study after transplantation of islet cells. This example indicates that treated mice maintain normoglycemia over a 60 day period (n=4), after the AAT therapy was withdrawn. After withdraw of the therapy, the normoglycemia lasted another 20 days. 6A illustrates the glucose follow-up. Positive insulin staining in a day-85 treated islet graft was also demonstrated (data not shown). 6B illustrates an immune infiltrate found outside the graft area. 6C illustrates an increase in the presence of CD4+ and a comparative decrease in monocytes and neutrophils. It was also shown that massive vascularization was evident inside the graft (data not shown). It has been observed that long-lasting accepted islet grafts can be spared from an immune alloresponse even after therapy removal, whether the therapy had evoked an immune tolerance specific for the strain of donor islets was evaluated. For this, grafts were explanted by nephrectomy and the now-hyperglycemic original recipients were re-transplanted with either the same strain of islets as before (n=2), or a $3^{rd}$ strain which they had never encountered before (n=2). In accordance with established strain specific immune tolerance, mice accepted grafts from original donors, but had acutely rejected $3^{rd}$-strain grafts (6D); the same donor (left) and a $3^{rd}$ donor re-graft (right).

Example 7

FIG. 7A-7E illustrates the production of AAT by islet cell and reflection of islet graft survival. 7A illustrates a time course expression of mouse AAT mRNA after cytokine production (IL-1β and IFNγ) (left) and at 8 hours (right). To demonstrate the relevance of endogenous alpha-1-antitrypsin in physiological conditions, the issue of islet injury during pancreatitis was addressed. In mouse model of acute pancreatitis, isolated islets of pancreata that are inflamed express inducible alpha-1-antitrypsin. 7B illustrates an example of islet injury during pancreatitis; the histology of normal islets (top left), the histology of islets of an inflamed pancreas (top right) and expression of mouse AAT in islets obtained from the pancreata in an acute pancreatitis model (bottom). Alpha-1-antitrypsin levels during pancreatitis (caerulein model for acute pancreatitis). Top, histology of an islet in a normal pancreas (left) and an islet in an inflamed pancreas (right), representative of n=3. Bottom, expression of mouse alpha-1-antitrypsin in islets obtained from pancreata in acute pancreatitis model. Treatment of mice with exogenous alpha-1-antitrypsin resulted in down-regulation of endogenous alpha-1-antitrypsin expression, as well as decrease in serum TNFα levels (not shown).

To demonstrate the relevance of endogenous alpha-1-antitrypsin in islet transplantation, islet allografts from untreated transplanted mice on days 1 through 7 after transplantation (n=3) were excised. These were examined for alpha-1-antitrypsin expression and reveal a pattern which may fit inflammation phase (days 1-3) followed by loss of islet mass (days 4-7). 7C illustrates an example of samples of islet allografts taken post grafting and percent change in AAT mRNA levels were also assessed. Total RNA was extracted and mRNA for alpha-1-antitrypsin evaluated by RT-PCR.

Islet protection from cytokine injury was examined using endogenous alpha-1-antitrypsin by introducing oncostatin M, a member of IL-6 family that induces alpha-1-antitrypsin expression in islets without causing islet death. After 4 days that human islets were incubated with oncostatin M, for the purpose of accumulation of sufficient alpha-1-antitrypsin, islets were added the β-cell-toxic combination of IL-1β/IFNγ. Pretreated islets that had excess alpha-1-antitrypsin were protected from injury, supporting the concept that islet-derived alpha-1-antitrypsin may participate in islet protection during inflammation. 7D illustrates an example of islet protection from cytokine injury with endogenous AAT by introducing oncostatin M (an interleukin 6 (IL-6) family member) that induces AAT expression in islets, oncostatin M and AAT levels (top left); nitric oxide and viability levels assessed (top right). Bottom, human islets exposed to oncostatin M for 4 days produce enough alpha-1-antitrypsin to diminish the effects of IL-1β/IFNγ added for an additional 48 hours.

Example 8

In one exemplary study, alpha-1-antitrypsin on human islets was examined. FIG. 8A-8D illustrates the effect of AAT on human islets. The production of nitric oxide (8A), TNFα production (8B) IL-6 (8C) and IL-8 (8D) was examined 100 human islets per well were seeded in triplicates and added alpha-1-antitrypsin (AAT) 2 hours before stimuli. Supernatants were assayed 72 hours later. 3A, nitric oxide; 3B, TNFα; 3C, IL-6; 3D, IL-8. Results are mean±SEM and are representative of separate islet isolations from three human donors.

Methods

In accordance with the present invention there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition 1989, Cold Spring Harbor Laboratory Press, Cold Spring Harbor, N.Y.; Animal Cell Culture, R. I. Freshney, ed., 1986).

Mice.

C57BL/6 and DBA/2 females were purchased from Jackson Laboratories.

Induction of Hyperglycemia by Streptozotocin, Islet Isolation and Islet Transplantation.

In one exemplary method, 5-6 weeks old C57BL/6 mice were treated intraperitoneally (i.p.) with 225 mg/kg Streptozotocin (STZ) (Sigma). Mice with established hyperglycemia were used at least 5 days after STZ administration. Islets were isolated from DBA/2 mice on day of transplantation, or 24 hours before in vitro assays, by enzymatic digestion of pancreata, by means known in the art, with minor modifications. Briefly, mice were anesthetized with i.p. ketamine (50 mg/kg, Vedco Inc.) and xylazine (10 mg/kg, Vedco Inc.). Each pancreas was inflated with 3.5 ml cold collagenase (1 mg/ml, type XI, Sigma), excised and immersed for 40 minutes at 37° C. in water bath. Pancreata were gently vortexed and filtered through 500-micron metal sieve. The pellet was washed twice in cold HBSS containing 0.5% BSA (Sigma) and reconstituted in RPMI-1640 (Cellgro, Mediatech) supplemented with 10% FCS (Cellgro), 50 IU/ml Penicillin (Cellgro) and 50 μg/ml streptomycin (Cellgro). Islets were collected on a 100-micron nylon cell strainer (BD Falcon), released into a petri dish by rinsing with HBSS (Cellgro, Mediatech) and 0.5% BSA (Sigma) and hand picked under a stereomicroscope. For transplantation, 450 islets were thoroughly washed from residual FCS in HBSS and 0.5% BSA and mounted on 0.2 ml tip for immediate transplantation. For in vitro assays islets were left to incubate for 24 hours at 37° C. Islet transplantation was performed into the left renal subcapsular space. Recipient mice were anesthetized, as described above. An abdominal wall incision was made over the left kidney. Islets were released into the subcapsular space through a puncture and the opening was sealed by means known in the art. Blood glucose follow-up was performed 3 times a week from end-tail blood drop using glucosticks (Roche). (Nanji, S. A. & Shapiro, A. M. Islet transplantation in patients with diabetes mellitus: choice of immunosuppression. BioDrugs 18, 315-28 (2004).)

Development of Anti-Human-AAT Antibodies in Mice.

In another exemplary method, in order to evoke specific antibody production against human AAT, mice were injected i.p. with 10 mg human AAT per 20-gram mouse for four times in intervals of 1 week. Mice were used in experiments 2 months after last administration. Antibody production was evaluated before transplantation experiments were carried out.

In one example, assaying for anti-human-AAT antibody levels was performed as described in the art. Briefly, mouse sera were kept at −70° C. until assayed for anti-human-AAT levels. Plates were coated with human AAT or albumin (2 μg/ml) in PBS at 4° C. overnight, then washed and blocked for 1 hour at 25° C. as described. Negative control serum was used in addition to test serum. Bound anti-AAT antibody using standard TMB substrate solution was measured (Sigma).

Cells.

NIH-3T3 cell line (e.g. ATCC) were cultured. On day of peritoneal inoculation, $1 \times 10^7$ cells were freshly collected by trypsinization and washed with cold PBS. Pellet was resuspended in 1 ml cold PBS for immediate injection.

Infiltration Experiments.

Peritoneal infiltration was elicited by i.p. injection of 1 ml autoclaved thioglycolate (3% w/v, Sigma) or allogeneic cells (NIH-3T3), together with 0.1 ml saline, human albumin, human AAT or oxidized AAT. Peritoneal lavage was performed at 24 and 48 hours (thioglycolate) or on days 1-5 (allogeneic cells). For lavage, mice were anesthetized by isoflurane inhalation and injected immediately with 5.5 ml cold PBS containing 5% FCS and 5 U/ml heparin into the peritoneal cavity. After massaging the abdomen, peritoneal fluid was recovered. Red blood cells were lysed (RBC lysing buffer, BD PharMingen) and cell counts were performed with a hemocytometer. Cells were then isolated. Cells (about $1 \times 10^6$/polypropylene vial) were incubated with FcγRIII/II receptor block antibodies (Table I) for 10 min. Cells were then divided into two groups and incubated with mAbs for leukocytes and either CD3/NK cells or neutrophil/monocytes/macrophages (Table I) for 30 min Cells were washed and fixed. The number of cells expressing a particular marker was calculated by multiplying percentages obtained from flow-cytometry by the concentration of cells in lavage fluid.

TABLE I

Rat Anti-Mouse mAbs Used for Flow Cytometry

| Purpose | mAb | (1) Specificity | (2) Source |
|---|---|---|---|
| Blocking | 2.4G2 | FcγRIII/II | BD PharMingen |
| Leukocytes | 30-F11 (APC) | CD45 (leukocytes) | BD PharMingen |
| Macrophages and Neutrophils | F4/80 (PE) | F4/80 (macrophages/monocytes) | eBiosciences |
|  | RB6-8C5 (FITC) | GR1 (neutrophils/monocytes) | PharMingen |
| CD3 | DX5 (PE) | Pan-NK cells | Miltenyi Biotec |
| NK cells | 17A2 (FITC) | CD3 | BD PharMingen |
| TNFα | MP6-XT22 (PE) | Mouse TNFα | eBiosciences |
| MHC class II | M5/114.15.2 (PE) | I-A$^{b/d}$, I-E$^d$ | BD PharMingen |
| Isotype control | Rat IgG1 (PE) |  | eBiosciences |

An insulin assay and immunohistochemistry were performed by means known in the art.

AAT Oxidation by Myeloperoxidase (MPO) System.

In one example, AAT (4 mg/ml) was incubated at 37° C. for 45 minutes with MPO (1 U/ml, Sigma), $H_2O_2$ (80 μM, Sigma) and NaCl (2.5 mM) in PBS, pH 7.4, by means known in the art. Reaction was terminated by boiling for 1 hour followed by filter-centrifugation of the system products. In this example, boiling was needed for the inactivation of MPO but this did not inactivate AAT (data not shown). Loss of activity of oxidized AAT was confirmed by elastase activity assay.

Elastase Activity Assay.

In another exemplary method, inhibition of a the serine protease elastase was evaluated 30 minutes after co-incubation of AAT or oxidized AAT with porcine elastase (Sigma) in triplicate, by known methods. The ability of elastase to liberate 4-nitroaniline ($A_{410}$) from SucAla$_3$-PNA was determined by kinetic measurement of light absorbance at 410 nm. Activity in the absence of inhibitors was set as 100% at the linear range of the assay.

Cytokine Assays.

An electrochemiluminescence (ECL) assay as known in the art was used for the measurement of mouse TNFα and MIP-1α. Briefly, cytokine-specific goat anti-mouse affinity purified antibodies were labeled with ruthenium (e.g. BioVeris) according to manufacturer's instructions. Biotinylated polyclonal anti-mouse antibodies (e.g. R&D Systems) were used. The amount of TNFα and MIP-1α chemiluminescence was determined using an Origen Analyzer (BioVeris).

Membrane TNFα.

Membrane TNFα on islet cells was detected by modification of a method for the evaluation of membrane TNFα on human PBMC. Briefly, single-cell suspension of islets was incubated with anti-mTNFα-PE mAb (Table I). Cells were washed with FACS buffer and resuspended in 0.5 ml 2% EM-grade formaldehyde.

Nitric Oxide Assay.

Nitrite levels in supernatants were determined using Griess reagent (Promega), as previously described (Chan, E. D. & Riches, D. W. Am J Physiol Cell Physiol 280, C441-50 (2001).

Apoptosis Assay.

The protective effect of AAT on islets may address one of the major obstacles in islet transplantation today, namely the inadequacy of islet mass and post-isolation islet viability. Freshly isolated human islets activate stress signaling pathways and exhibit high rate of apoptosis due to the process of isolation, necessitating the use of more than one islet donor per diabetic patient (Nanji, (2004); Abdelli, S. et al. Intracellular stress signaling pathways activated during human islet preparation and following acute cytokine exposure. Diabetes 53, 2815-23 (2004)).

In this example, apoptosis that follows islet isolation is diminished when islets are cultured with AAT (data not shown) and demonstrate that islets that are cultured with AAT for 24 hours prior to transplantation are able to normalize serum glucose levels of diabetic mice when transplanted autologously at an otherwise sub-functional mass (data not shown).

AAT Dosage.

Normal human plasma contains 0.8-2.4 mg/ml AAT, with a half life of 5-6 days[1]. In gene transfer studies in C57BL/6 mice, plasma levels of 0.8-1.0 mg/ml were achieved and provided protection from type I diabetes in NOD mice (Song, S. et al Gene Therapy 11, 181-6 (2004)). AAT administered intraperitoneally at 0.3-1.0 mg per mouse protected from TNFα-induced lethal response, and 0.8 mg AAT protected from D-galactosamine/LPS induced hepatic injury. Libert, C., et al., J Immunol 157, 5126-9 (1996).

Since AAT levels rise 3- to 4-fold during the acute phase response 1, 2 mg per mouse results in plasma levels that do not exceed physiological levels.

Statistical Analysis.

Comparisons between groups were analyzed by two-sided t-test or ANOVA for experiments with more than two subgroups. Results are presented as mean±SEM.

Prolongation of Islet Graft Survival by AAT.

In the present study, administration of clinical grade AAT to mice transplanted with allogeneic islets prolonged graft survival. In addition, AAT reduced migration of neutrophils and the subsequent infiltration of lymphocytes and NK cells in models of peritonitis. AAT also decreased secretion of TNFα and MIP-1α from islets and inhibited surface MHC class II expression on CD45+ islet cells in vitro. AAT was protective in a model of streptozotocin (STZ)-induced β-cell toxicity. Thus, it appears that AAT monotherapy targets several aspects of an activated inflammatory immune system, culminating in prolongation of islet allograft survival.

Effect of AAT on Cell Infiltration.

AAT diminished neutrophil migration into the peritoneum of mice injected with either thioglycolate or MHC-incompatible fibroblast cells. Other studies demonstrate that AAT inhibits neutrophil infiltration into kidneys during ischemia/reperfusion injury and into lungs following intratracheal administration of silica. In the present study AAT decreased islet production of MIP-1α and TNFα, resulting in islets deficient in chemotactic capabilities and therefore less immunogenic. The detrimental effect of neutrophils recruited to islets has been clearly demonstrated.

The involvement of macrophages in islet destruction is critical; their presence precedes insulitis in NOD mice and in prediabetic BB rat, and their depletion is protective during islet transplantation in rats. Islets are potent recruiters of macrophages; of the 51 gene products identified in freshly isolated human islets by cDNA array, expression of MCP-1 was found to be high. In mice, blockade of MCP-1 prolongs islet allograft survival when combined with a short subtherapeutic course of rapamycin. Islet allograft rejection is associated with a steady increase in intragraft expression of MCP-2, MCP-5, CCL5, CXCL-10 and CXCL9, and the chemokine receptors CCR2, CCR5, CCR1 and CXCR337. Accordingly, CCR2−/− mice and CXCR3−/− mice exhibit prolongation of islet allograft survival. In transplant settings, cytokines that are produced locally, as TNFα and IL-1β, cause damage to proximal cells independent of antigen recognition, and complement activation is critical for graft survival independent of allospecific immunity. The relevance of macrophages during early events in islet graft rejection is strengthened by the identification of CD45, F4/80 and Gr1 positive cells that express MHC class II in freshly isolated islets. In the presence of AAT, MHC class II levels were decreased below those of IL-1β/IFNγ-stimulated and unstimulated islets, supporting the idea that the process of islet isolation is sufficient to provoke activation of inflammatory pathways in islet cells. In light of the involvement of neutrophils and macrophages in graft rejection, interference with their functions by AAT provides an unusually non-inflammatory environment for the survival and recovery of engrafted islets.

As shown in the present study and elsewhere intraperitoneal injection of allogeneic NIH-3T3 cells evokes infiltration of macrophage and neutrophil on days 1-2 and of CD3+ and NK cells on days 4-5. The intensity of the latter infiltration was decreased by administration of AAT prior to allogeneic cell-line injection, but not by administration of AAT on day 3 (data not shown). In transplant settings, early non-specific factors contribute to subsequent specific immune response. It is therefore possible that the decrease in CD3+ and NK cell infiltration in the present study is secondary to the functional failure of the early innate response. However, regardless of AAT treatment, histological examination of islet grafts demonstrated that the infiltrate evoked by allogeneic islets consists of neutrophils and lymphocytes. Nevertheless, day 7 infiltrate was diminished in AAT-treated recipients, and, according to day 15 insulin immunohistochemistry, the infiltrate caused less islet destruction.

AAT Inhibits Release of TNFα.

Supernatants of IL-1β/IFNγ-stimulated islets contained strikingly less TNFα when incubated with AAT (induction of 100.0%±22.0 mean±SEM at 0 mg/ml AAT; 10.2%±11.2 at 0.5 mg/ml and 0.8%±0.1 at 1.0 mg/ml). In stimulated human PBMC, AAT was shown to diminish TNFα release without affecting TNFα-mRNA levels. In mice, accordingly, serum TNFα levels are decreased in LPS-injected AAT-treated mice. Importantly, treatment of mice with AAT blocks TNFα-mediated LPS-induced, but not TNFα-induced lethality in mice. In the present study, cultured mouse splenocytes isolated from thioglycolate-injected mice secreted less TNFα, 48 hours after injection of AAT.

In the presence of AAT, membrane TNFα accumulated in IL-1β/IFNγ-stimulated CD45+ islet cells. TNFα is released from the cell surface of macrophages by the action of TNFα converting enzyme (TACE), a metalloproteinase that cleaves membrane TNFα into the soluble form of TNFα Inhibitors of TACE reduce TNFα release and increase the levels of membrane TNFα, as demonstrated by FACS analysis. Although the regulation of TACE activity is unclear, there is evidence to suggest that extracellular proteases are involved: TACE does not require its cytoplasmic domain for its activation, its activity does not depend on the amount of TACE on the cell surface, co-expression of TACE and transmembrane TNFα is not sufficient for processing of TNFα and the enzyme is expressed constitutively in various cells. Serpins, such as serpin PN-I52, are suggested to possess extracellular regulatory effects on various surface proteins.

TACE is likely to be relevant for graft rejection since TACE inhibitor decreased injury parameters in a rat model of post-transplant lung injury. In addition to a decrease in TNFα levels, the study shows lower expression of MCP-1 and ICAM-1, and a reduction in neutrophil infiltration. Similar findings were obtained with both AAT and a broad spectrum metalloproteinase inhibitor in a model of silica induced neutrophil influx into lungs. However, TACE inhibitor only partially reproduced the protective effect of AAT on islet graft survival (preliminary data). Similarly, AAT protection from STZ-induced hyperglycemia was only partially reproduced by TACE inhibition and by recombinant p75-TNF-receptor. Despite the fact that locally secreted TNFαα is detrimental to islet graft function, there is, to our knowledge, no report that describes protection of islet grafts by neutralization of TNFα activity. This distinction between AAT and TACE inhibition supports the possibility that AAT affects multiple aspects of the immune system, including not only TNFα release but also events that are downstream to TNFα activities.

In one embodiment, it is contemplated that a composition of the present invention may include AAT, an analog thereof, a serine protease, TACE inhibitor (TACEi) or any combination thereof. These compositions may be administered to a subject having or in need of a transplant and or in need of immunotolerance therapy.

Transplanted Islets are Stimulated by the Process of Isolation.

The process of islet isolation initiates in the islets an inflammatory cascade of cytokines and chemokines. Thus, isolated islets contain an intrinsic proinflammatory potential that may affect local host immune responses. The mechanism of cytokine-induced islet toxicity is believed to involve expression of inducible nitric oxide synthase and subsequent production of nitric oxide (NO) by non-β-cells. In the present study, AAT decreased NO production in IL-1β/IFNγ-treated islets. Accordingly, islet viability was increased in a low NO environment, as attained by either incubation with a low concentration of stimulators (data not shown) or by introduction of AAT. Insulin induction, which is typically incomplete in the presence of cytokines, was intact in the presence of AAT and cytokines. In vivo, AAT protected islets in mice injected with STZ, as concluded by lower serum glucose levels. The portion of viable β-cells was visually assessed by insulin immunohistochemistry and was proportional to the decrease in serum glucose levels. The protection of AAT was limited to the initial days that follow STZ administration, suggesting that AAT interferes with NO production and immune activation and not with intracellular DNA alkylation. Freshly isolated non-stimulated CD45+ islet cells expressed MHC class II, which is involved in immune responses against islets. The levels of MHC class II were elevated in the presence of IL-1β/IFNγ and decreased in the presence of AAT. Interestingly, MHCII expression was unaffected by the presence of TACE (TNF alpha converting enzyme) inhibitor (data not shown), confirming that AAT activities extend beyond those of TACE inhibition.

According to the present study, the activities of AAT are directed against multiple components of the innate immune system, culminating in a protective effect on islet graft destruction. Islets in particular exhibited a high degree of protection from inflammatory processes in the presence of AAT. Pretreatment with AAT prior to islet transplantation may reduce both islet loss and the immunological response against the graft.

The terms and expressions that have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed herein, optional features, modification and variation of the concepts herein disclosed may be resorted to by those skilled in the art, and that such modifications and variations are considered to be within the scope of this invention as defined by the appended claims. In addition, where features or aspects of the invention are described in terms of Markush groups, those skilled in the art will recognize that the invention is also thereby described in terms of any individual member or subgroup of members of the Markush group and that other members of the described groups are included but may not be listed.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

Example 9

In one exemplary method to determine whether administration of hAAT affects the severity of GvHD and subsequent mortality from the condition, three models for GvHD were examined. In the first model, hAAT was administered in a dose-dependent manner in a MHC disparate B6 (H-$2^b$)→B6D2F1 (H-$2^{b/d}$) mouse model and the severity of GvHD was examined. Lethally irradiated B6D2F1 mice received BM and splenic T cells from syngeneic (B6D2F1) or allogeneic (B6) donors. BMT recipients were injected i.p. with 1, 2, or 4 mg per mouse of either hAAT or human albumin as control, as of 2 days prior to transplantation and then every other day through day 13 after transplantation. This schedule was chosen in order to modulate the inflammatory cascade of acute GvHD, which is most severe before day 7 after transplantation. In addition, the dose of 2 mg per mouse was reportedly effective in allograft rejection and autoimmune models.

Figures 9A, 9B, 9C:
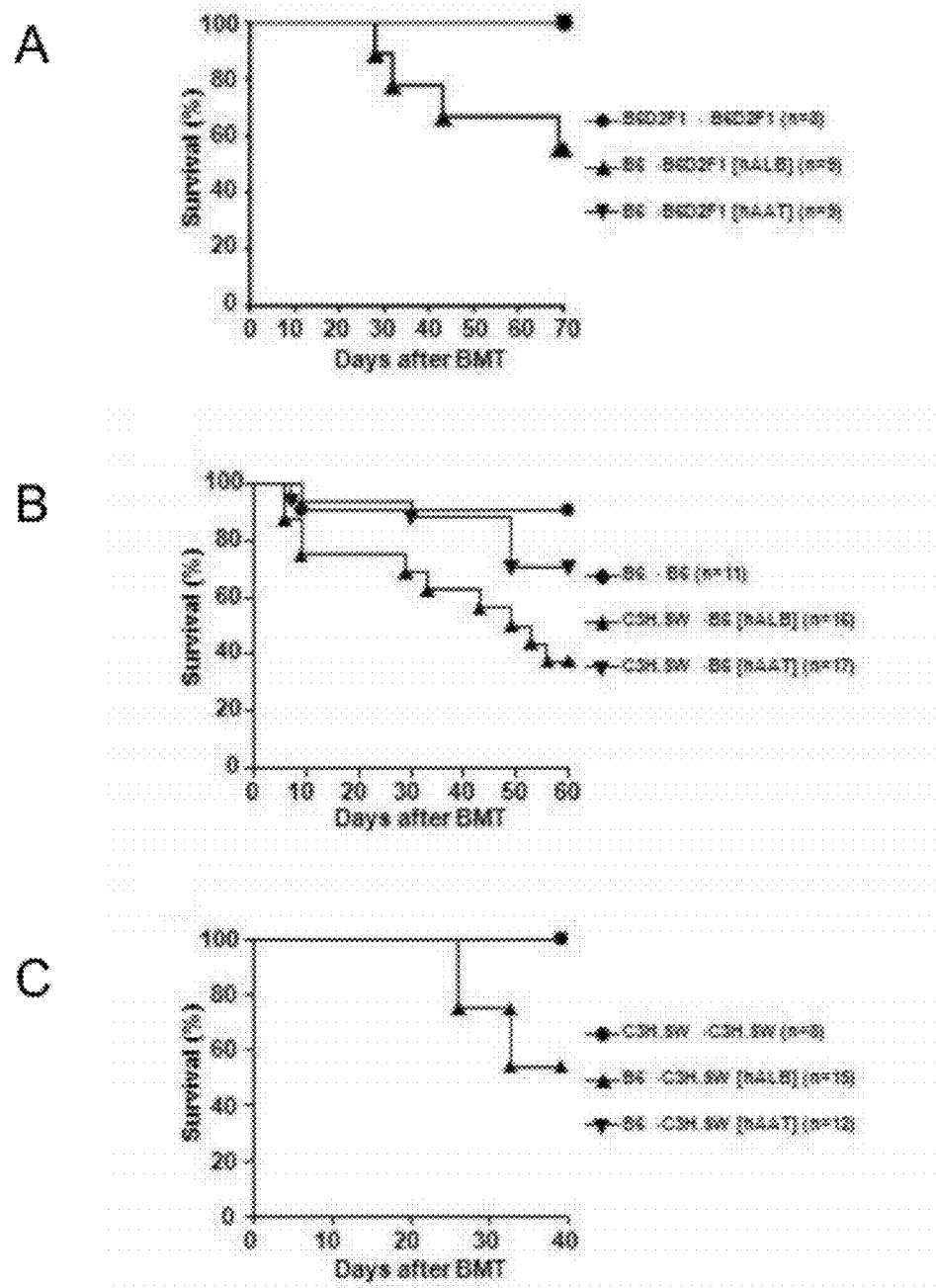
FIGS. 9A-9C represents affects of AAT to reduce mortality in bone marrow transplantations in a mouse model under various conditions. A) represents percent survival of mice after bone marrow transplantation (BMT). B) represents BMT transplanted mice under various conditions related to T cell depletion. C) represents BMT mouse model having T-cell depleted bone marrow and followed under various conditions.

As illustrated in FIG. 9A, hAAT administration at 4 mg per mouse significantly reduced mortality from GvHD when compared with allogeneic controls (100% survival vs. 50% survival at day 70, P<0.02). hAAT administration at 1 mg per mouse had only modest effects on mortality, while at 2 mg per mouse hAAT appeared to have prolonged animal survival All surviving mice displayed complete donor chimerism (97%+/−2%), as determined by fluorescence-activated cell sorter analysis, excluding both the possibility that graft failure had occurred and that the protection was the result of mixed chimerism.

To demonstrate that reduction of GvHD by hAAT is strain independent, hAAT was also administered to experimental groups comprised of C3H.SW (H-$2^b$)→B6 (H-$2^b$), a MHC matched mouse model of acute GvHD that is driven by donor CD8$^+$ T cells and is directed against minor histocompatibility antigens. Here, recipient B6 mice were conditioned and then transplanted with either syngeneic (B6) or allogeneic (C3H.SW) donor BM. As shown in FIG. 9B, administration of hAAT at 2 mg per mouse significantly improved survival when compared with control allogeneic human albumin-treated mice (78% survival vs. 40% survival at day 60, P<0.03).

In another example, the effect of hAAT in MHC matched minor disparate CD4$^+$ dependent but CD8$^+$ driven T cell mediated GvHD was examined using B6 (H-$2^b$)→C3H.SW (H-$2^b$) strain combination. As shown in FIG. 9C, administration of hAAT completely prevented mortality in allogeneic animals from GvHD when compared to control human albumin-treated allogeneic animals (100% survival vs. 50% survival at day 40, P<0.02).

Example 10

AAT Alters Mature Donor T Effector to Treg Ratio after Allogeneic BMT.

The expansion of mature donor cytopathic effector T cells (Teffs) and Tregs was determined and the ratio of Teffs to Tregs (Teffs:Tregs) was calculated in allogeneic transplants treated with hAAT. Mice (B6) were irradiated and transplanted with BM and CD8$^+$ T cells from the allogeneic C3H.SW donors. Since expansion of alloreactive T cells peaks at 3-4 weeks in this model, splenocytes from recipient animals were isolated at four weeks and analyzed for donor Teff and Treg cell expansion by donor specific congeneic markers. (Data not shown). Administration of hAAT resulted in reduced expansion of splenic CD8$^+$ donor Teffs. In contrast, the expansion of donor Tregs was increased, resulting in the reduction of the Teff:Treg ratio when compared with the control animals. To exclude the possibility of confounding effects of donor BM derived Tregs in these analyses, and to analyze the kinetics of mature donor Teffs:Tregs, we used B6 GFP$^+$ foxp3 knock-in mice as donors for Tregs (GFP$^+$ and Ly5.1$^+$) and mature Teffs (GFP$^-$ and Ly5.1$^+$). In a similar manner, B6 Ly5.2 (CD45.1) used as the source of donor BM are responsible for CD45.2$^+$ mature Teff (GFP$^-$) or Tregs (GFP$^+$). These cells were infused into the MHC matched but minor disparate C3H.SW animals and the expansion of the mature Teffs and Tregs was determined.

Figures 10A, 10B, 10C, 10D:
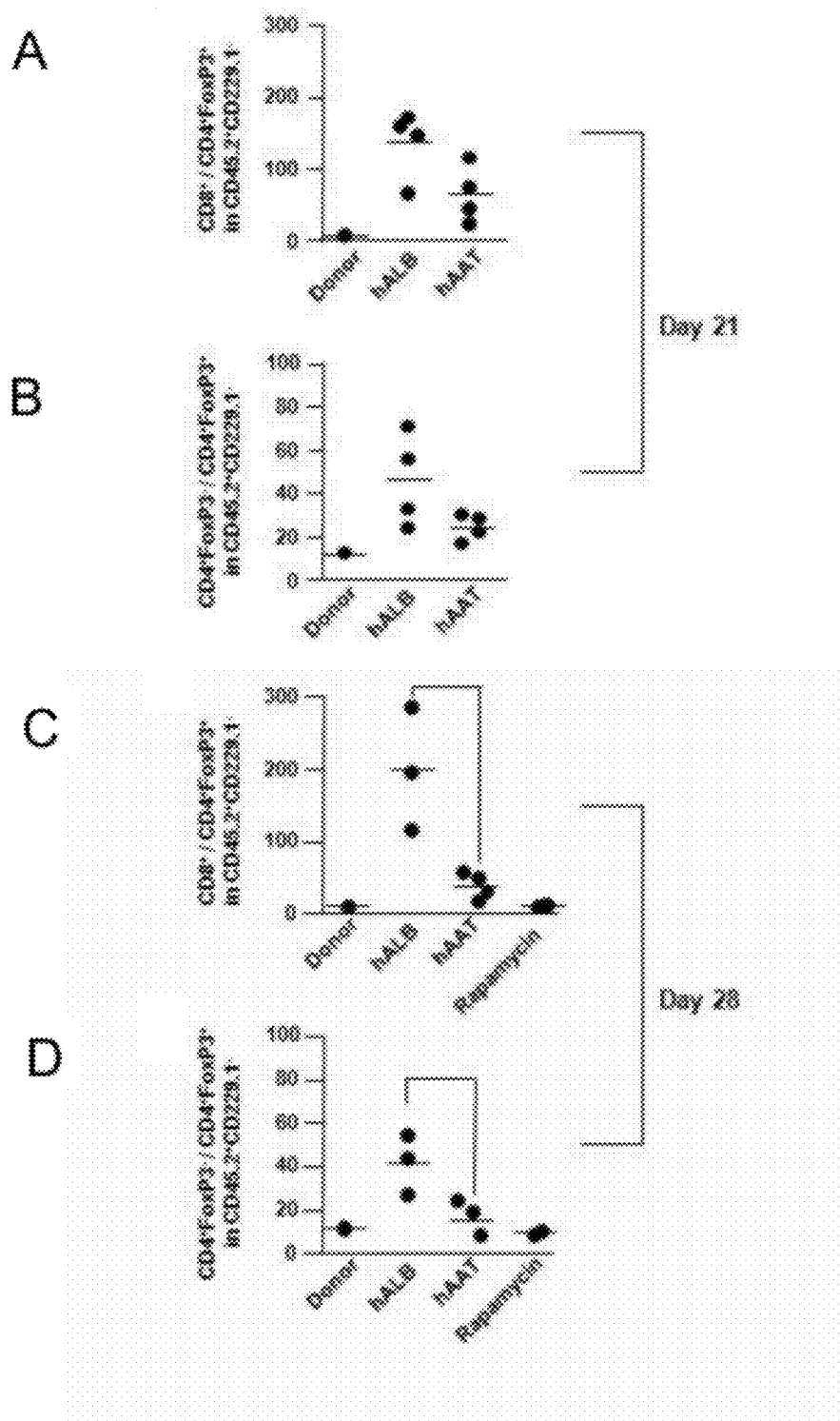
FIGS. 10A-10D represent affects of human AAT (hAAT) and a control on the ratio of donor Teff:Treg cells in a subject Each point represents one individual mouse (n=2-5/group). (A) CD4$^+$:Treg ratio on day +21, vehicle vs. hAAT, P=0.037 (B) CD8$^+$:Treg ratio on day +21, vehicle vs. hAAT, P=0.022. (C) CD4$^+$:Treg ratio on day +28, vehicle vs. hAAT, P=0.0223 and (D) CD8$^+$:Treg ratio on day +28, vehicle vs. hAAT, P=0.0127.

Since both CD4$^+$ and CD8$^+$ T cells are responsible for mortality in this model, the ratio of both mature donor CD4$^+$ Teff and mature CD8$^+$ Teffs to the mature donor GFP$^+$ Tregs were analyzed on days 21 and day 28 after BMT. As shown in FIGS. 10A-10D, the ratio Teffs:Tregs was significantly altered for both CD4$^+$ and CD8$^+$ Teffs on both days 21 and 28. The effect of hAAT was compared to rapamycin, an immunosuppressive agent that has been shown to enhance Tregs in these models. As shown in FIGS. 10C-10D, alteration in Teffs:Tregs ratio by hAAT was similar to the effects induced by rapamycin on day 28.

Given the alteration in the expansion and the ratio of the donor Teffs and Tregs cells, we next determined whether hAAT had direct effects on donor Teff responses in vitro. The proliferation of Treg depleted donor T cells (BALB/c) to allogeneic (B6) BM-derived dendritic cells (DC) was equivalent regardless of whether the donor T cells were pretreated with hAAT or vehicle (data not shown).

In order to determine the direct impact of hAAT on T cells without a confounding effect of hAAT on accessory cells, anti-CD3-induced T cell activation was examined in the presence of hAAT. Consistent with previous reports addition of AAT did not interfere with T cell responses (data not shown). In addition, hAAT allowed uninterrupted T cell lysis of host-type conA blast cells following priming (57% and 63%, at 50:1 E; T ratio, P=NS).

Figure 11:
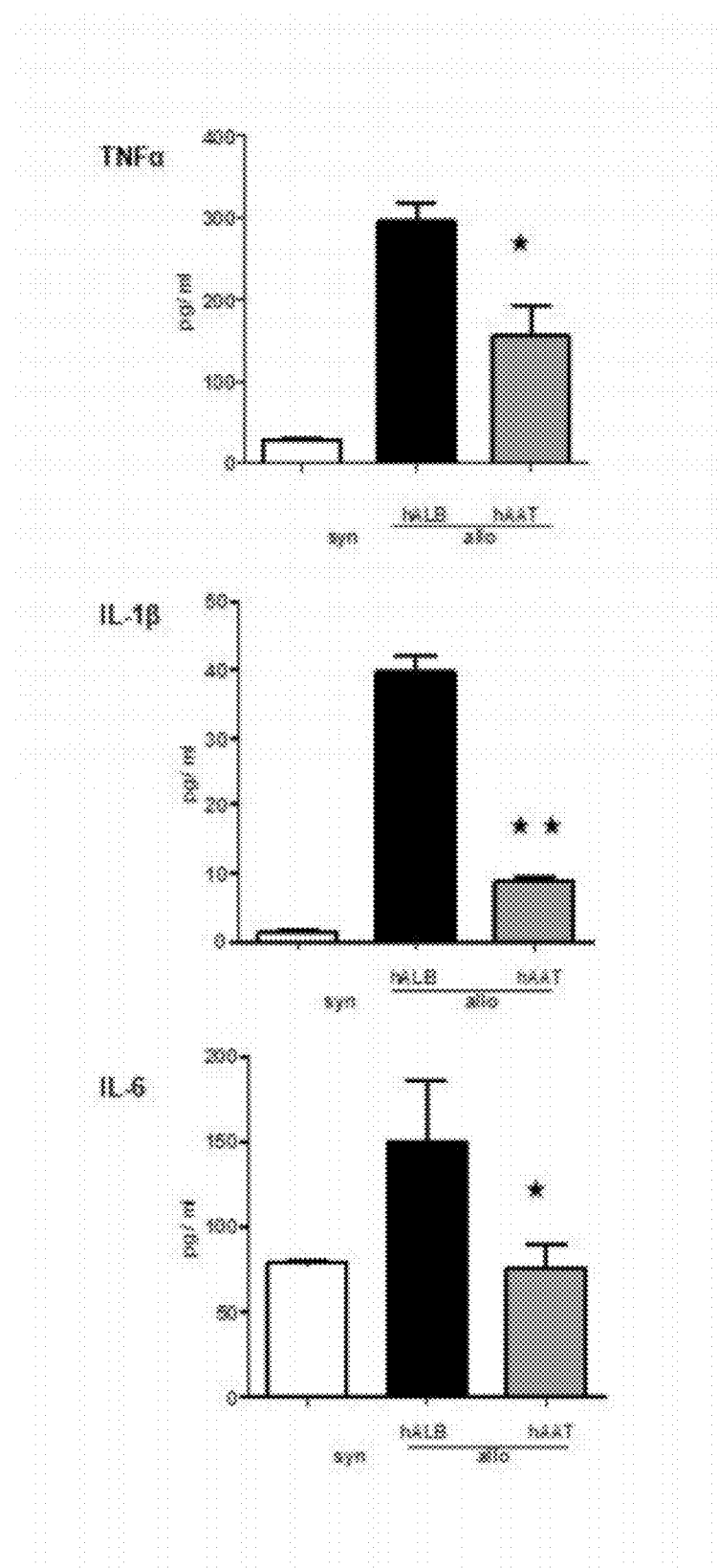
FIG. 11 represents affects of AAT on proinflammatory cytokines produced after BMT.

AAT inhibits proinflammatory cytokine release after allogeneic BMT. The presence of proinflammatory cytokines has been shown to enhance the expansion of Teffs while mitigating the responses of Tregs. In particular, IL-1β TNF-α and IL-6 have been shown to play a critical role in severity of GvHD. Therefore, alteration of Teffs:Tregs ratio and protection from GvHD may be a consequence of suppression of proinflammatory cytokine secretion by hAAT. Mice (B6D2F1) were irradiated and transplanted with BM and T cells that are either syngeneic F1 or allogeneic (B6) donors. Recipient animals were injected with either hAAT or albumin at 4 mg per mouse on days −2, 1, and 4 from transplantation, and serum samples were analyzed on day +7 from transplantation for TNF-α, IL-1β and IL-6. As shown in FIG. 11, administration of hAAT significantly reduced serum levels of all three proinflammatory cytokines when compared with controlallo-recipients.

Given the lack of direct effect of hAAT monotherapy on donor T cells, we next reasoned that the reduction in proinflammatory cytokines and GvHD severity might be the consequence of an effect of hAAT on host antigen presenting cells (APC). The effect of hAAT on dendritic cells was thus examined. BM-derived DC from B6 mice were incubated overnight with hAAT prior to stimulation with 100 ng/ml LPS for 8 hours. The secretion of proinflammatory cytokines from AAT-treated DCs was significantly reduced (data not shown). In contrast, the secretion of anti-inflammatory cytokine, IL-10, was significantly enhanced by hAAT when compared with albumin treated controls. The changes in IL-6 and IL-10 were also observed under similar conditions in host F4/80$^+$ macrophages (data not shown).

AAT Inhibits LPS-Induced NF-KB Translocation in DCs

In order to examine a possible mechanism for the reduction of LPS-induced proinflammatory cytokine secretion by hAAT in BM DCs, NF-κB translocation into the nucleus was determined AAT or human albumin were added to BM derived DCs and then stimulated with LPS. NF-κB translocation was analyzed by electrophoretic mobility shift assay (EMSA) in the nuclear fraction of cell lysates. Treatment with hAAT significantly reduced LPS induced translocation of NF-κB into the nucleus when compared with control DCs (data not shown).

In the current study, monotherapy with hAAT reduced proinflammatory cytokines and GvHD mortality in multiple models. The concentrations and doses of AAT used in the current study are derived and further extended from these reports, according to which 2 mg hAAT per mouse are sufficient to allow islet allograft acceptance (a dose that is comparable to that used routinely in humans that are deficient in AAT), and 0.5 mg/ml hAAT protects various cell types in vitro from multiple injuries. Thus, in vivo doses of 1, 2 and 4 mg per mouse were examined, and also tested in vitro concentrations up to 4 mg/ml. The present data demonstrate that exogenous administration of hAAT after allogeneic BMT suppresses proinflammatory cytokines, alter the ratio of T effector cells to T regulatory cells and more importantly reduces GvHD severity and related mortality.

Materials and Methods

Human alpha-1 antitrypsin and albumin. Clinical grade human alpha-1 antitrypsin (hAAT, Aralast™) and human albumin were obtained from Baxter (Deerfield, Ill.). Rapamycin was purchased from LC Laboratories (Woburn, Mass.), reconstituted in ethanol at 10 mg/ml and diluted in 5% Tween-80 (Sigma) and 5% PEG-400 (Hampton Research, Aliso Viejo, Calif.). Rapamycin was injected at 4 mg/Kg, i.p. daily from 1 day prior to BMT transplantation.

Mice: Female C57BL/6 (B6, H-2$^b$, CD45.2$^+$, CD229.1$^-$), C3H.SW (H-2$^b$, CD45.2$^+$, CD229.1$^+$) mice were purchased from the Jackson Laboratories (Bar Harbor, Me.). B6-Ly5.2 (H-2$^b$, CD45.1$^+$, CD45.2$^-$, CD229.1$^-$), B6D2F1 (B6, H-2$^{b/d}$, CD45.2$^+$, CD229.1$^-$) mice were purchased from the Charles River Laboratories (Wilmington, Mass.). GFP-FoxP3 knock-in mice (GFP-Foxp3, H-2$^b$, CD45.1$^+$, CD45.2$^+$, CD229.1$^-$) were provided by Dr. Rudensky (University of Washington, Seattle).

Bone marrow transplantation: Bone marrow transplantation was performed as described. Briefly, splenic T cells from donor mice were enriched by MACS cell separation system using anti-CD90.2 microbeads or pan T cell isolation kit (Miltenyi, Auburn, Calif.). Bone marrow T cells were depleted using anti-CD90.2 microbeads. Recipient mice were irradiated ($^{137}$Cs source) with 10 Gy total body irradiation (TBI) on day −1 and injected with either syngeneic or allogeneic T cells (1-2×10$^6$ or 2×10$^5$) along with 4-5×10$^6$ T cell-depleted bone marrow cells (TCDBM). Mice were housed in sterilized microisolator cages and received normal chow and autoclaved hyperchlorinated water for the first 3 weeks after BMT and filtered water thereafter. Survival was monitored daily, clinical GVHD score was assessed weekly Animal studies were approved by the University of Michigan Committee on the Use and Care of Animals.

Bone marrow dendritic cell generation: DCs were generated as described (35). Briefly, Bone marrow cells were isolated from mouse femurs and tibias and cultured in the presence of 20 ng/ml recombinant murine GM-CSF (Peprotech, Rocky Hill, N.J.) for 7 days. CD11c$^+$ dendritic cells were isolated from bone marrow culture by MACS cell separation system using CD11c micro beads (Miltenyi).

Flow cytometric analysis: Flow cytometric analysis was performed using FITC, PE, PerCPCy5.5 or APC-conjugated monoclonal antibodies (mAbs) to mouse CD4 (clone RM4-4), CD229.1 (3007) (BD Pharmingen, San Jose, Calif.), CD8a (53-6.7), CD25 (PC61.5), CD45.1 (A20), CD45.2 (104), (eBioscience, San Diego, Calif.). Cells were stained, analyzed on a FACSVantage SE (Becton Dickinson, San Jose, Calif.) or C6 cytometer (Accuri Cytometers, Ann Arbor, Mich.) as described.

Electrophoretic mobility shift assay (EMSA): CD11C$^+$ DCs were isolated from 16 B6 mice, uniformly divided into 4 dishes (100 mm), treated with hALB (1 mg/ml) or hAAT (1 mg/ml) for 4 hours and then treated with LPS (500 ng/ml) or diluent for another 3 hours. Nucleic extracts were incubated with $^{32}$P-ATP-labeled probe specific for NF-κB binding, derived from the class I MHC gene promoter for 30 min at room temperature. After reaction, the samples were separated by 5% polyacrylamide gel, dried and visualized by autoradiography.

Enzyme-linked immunosorbent assay (ELISA): ELISAs for TNFα, IL-1β, IL-6 and IL-10 (BD Pharmingen) were performed according to manufacturers' protocol. In vitro suppression assay: CD4$^+$CD25$^-$ and CD4$^+$CD25$^+$ T cells were isolated from spleen cells from BALB/c mice using MACS cell separation system (Miltenyi). The purity of CD4$^+$CD25$^-$ and CD4$^+$CD25$^+$ T cells was >85%. CD4$^+$CD25$^-$ T cells were serially diluted from 2×10$^4$ to 2,500 cells/well and incubated with 2×10$^4$ CD4$^+$CD25$^-$ T cells and 500 or 2,500 allogeneic B6 bone marrow-derived dendritic cells for 72, 96 or 120 hours. Incorporation of $^3$H-thymidine (1 μCi/well) by proliferating cells was measured during the last 12 hours of culture, as described.

Statistical analysis: Survival curves were plotted and compared by log-rank analysis; P<0.05 was considered statistically significant. A paired t-test was used to evaluate significant differences between groups in in vitro experiments. Data expressed mean±SE. FIG. 9

(A) B6D2F1 mice were irradiated with 1,000 cGy of total body irradiation in day −1 and transplanted with 5×10⁶ T cell-depleted BM cells and 2×10⁶ CD90⁺T cells from either syngeneic F1 or allogeneic B6 donors. Each allo recipient was injected i.p. with either 4 mg hAAT (n=9) or human albumin (n=9) for 6 days from day −2 to day +13. Data shown are combined from two similar experiments. Percent survival after BMT. ▼● vs. ▲, P<0.02 (B) B6 mice were given 1,000 cGy of total body irradiation in day −1 and transplanted with 5×10⁶ T cell-depleted BM cells and 2×10⁵ CD8⁺T cells from either syngeneic B6 or allogeneic C3H.SW donors. Each allo recipient was injected i.p. with either 2 mg hAAT (n=17) or human albumin (n=16) for 6 days from day −2 to day +13 and were monitored for GvHD survival. Data shown are combined from three similar experiments. Percent survival after BMT. ▼● vs. ▲, P=0.029.

(C) C3H.SW mice were irradiated as above and transplanted with 4×10⁶ T cell-depleted BM cells and 1×10⁶ CD90⁺T cells from either syngeneic C3H.SW or allogeneic B6 donors. The allo recipients were injected i.p. with either 2 mg hAAT (n=12) or human albumin (n=15) and were monitored for GvHD survival as above. Data shown are combined from two similar experiments. Percent survival after BMT. ▼● vs. ▲, P=0.019. FIG. 10 represents that hAAT alters the ratio of mature donor Teff:Treg cells C3H.SW mice were irradiated and transplanted with either allogeneic B6GFP⁺Foxp3 knock-in donors. The recipient animals received either hAAT or rapamycin or the control vehicle as above. Expansion of mature donor (CD45.2⁺CD45.1CD229.1GFP⁻) CD4 and CD8⁺ effectors and the mature donor (CD45.1CD45.2⁺CD229.iGFP⁺) Tregs were analyzed in the peripheral blood on day +21 and +28. ratio of CD8⁺ to CD4⁺ FoxP3⁺ T cell absolute numbers of mature donor-derived (CD45.2⁺CD45.iCD229.1⁺). Each point represents one individual mouse (n=2-5/group). (A) CD4⁺:Treg ratio on day +21, vehicle vs. hAAT, P=0.037 (B) CD8⁺:Treg ratio on day +21, vehicle vs. hAAT, P=0.022. (C) CD4⁺:Treg ratio on day +28, vehicle vs. hAAT, P=0.0223 and (D) CD8⁺:Treg ratio on day +28, vehicle vs. hAAT, P=0.0127

FIG. 11 represents injection of hAAT inhibits in vivo proinflammatory cytokine production after BMT B6D2F1 mice were exposed 1,000 cGy of total body irradiation and transplanted with 5×10⁶ T cell-depleted BM cells and 2×10⁶ T cells from either allogeneic (B6) or syngeneic (B6D2F1) donors. Each F1 recipient of the allogeneic cells were injected i.p. with 4 mg hAAT or human albumin on days −2, +1 and +4. Sera from the recipient animals (n=4-5 per group) were obtained by on day 7 after BMT and analyzed for TNFα, IL-1J3 and IL-6. Albumin treated allogeneic controls (solid bars) vs. hAAT allogeneic recipients (open, gray bars) for TNFα*, P<0.04. IL-1J3. Allo **, P<0.03. IL-6 *, P<0.04.

Example 11

In other embodiments, it was demonstrated that inhibition of IL-32 activation by alpha-1 antitrypsin suppresses alloreactivity and increases survival in an allogeneic murine marrow transplantation model.
Materials and Methods
Patients, Sample Collection, and Follow-Up Patient characteristics, treatment regimens, and clinical outcome data were collected prospectively and stored in the FHCRC database. Patients were transplanted for various hematologic malignancies; they were 12-65 (median 43) years of age at the time of HCT. Patients received cyclosporine or tacrolimus, combined with a short course of methotrexate or mycophenolate mofetil as GVHD prophylaxis. The source of stem cells were peripheral blood stem cells in 31 patients and bone marrow in 6 patients. All patients and controls had given informed consent to participate in research studies as required by the Institutional Review Board of the Fred Hutchinson Cancer Research Center (FHCRC). Patients with acute GVHD. White blood cells (WBC) were collected from 15 patients at a median of 24 (range: 18-38) days post-HCT; among these, 10 developed acute GVHD and were studied before systemic therapy was started. Five of the 10 acute GVHD patients had serially collected samples before onset of GVHD for a total of 15 samples. Eight samples (including 3 sequential ones) were collected from 5 patients who never developed GVHD during the first 100 days post-HCT. Four of 15 patients were serologically CMV+, as were 4 of the 15 transplant donors.

Patients with chronic GVHD. PBMC were collected from 22 patients with active chronic GVHD at a median of 806 (range: 349-5473) days post-HCT; among these, 14 were receiving immunosuppressive therapy, and 8 did not. Among the 22 patients with chronic GVHD, 12 were CMV+, as were 7 of the donors.

Healthy controls. Control samples were collected from 9 healthy individuals, 22-73 (median 37) years old.
Cell Separation and Reagents WBC were separated by Dextran sedimentation (early after HCT when blood cell counts were low) and PBMC were separated by Ficoll-Hypaque density gradient centrifugation (in patients with chronic GVHD). RNA was extracted from WBC and PBMC using Trizol as previously described. cDNA synthesis was performed from 500 ng of total RNA using Invitrogen Superscript RT (Invitrogen, Carlsbad, Calif.). Goat polyclonal anti-human IL-32 antibody AF3040, was obtained from R&D Systems (Minneapolis, Minn.), rabbit policlonal antiβ-actin antibody from Santa Cruz Biotechnology (Santa Cruz, Calif.) and each used according to the manufacturers' recommended conditions. Concanavalin A was purchased from Sigma-Aldrich Co. (St. Louis, Mo.); Aralast NP (human α-1-antitrypsin), a serum serine-protease inhibitor that blocks the enzymatic activity of neutrophil elastase, cathespin G, PR3, thrombin, trypsin, and chymotrypsin, was purchased from Baxter (Westlake Village, Calif.).
RNA Interference (RNAi) and Transient Transfection Stealth siRNA oligonucleotides, specifically designed to silence the expression of all IL32 isoforms, were obtained from Invitrogen (Carlsbad, Calif.). PBMC from healthy donors (1×10⁶) were electroporated with 500 ng of siRNA by nucleofection (Human Cell Nucleofector kit, Program V-024, Amaxa Biosystems, Cologne, Germany).
Human Cytokine Protein Array After transfection with either scrambled or IL32-specific siRNA, PBMC were cultured for 96 hours in RPMI 1640 medium, containing 5% fetal bovine serum (FBS), and penicillin/streptomycin (P/S) (50 U/ml and 50 μg/ml, respectively), and supernatants were collected. To determine the presence of various cytokines, we used the human proteome profiler array membrane kit Panel A (ARY005; R&D Systems, Minneapolis, Minn.; USA) according to the manufacturer's instructions. Equal volumes (1 ml) of supernatant were collected from cultured PBMC and added to the precoated membranes of the kit. The dot blot membranes (standardized for loading control) were analyzed using ImageQuant software (Molecular Dynamics, Sunnyvale, Calif.).

Mixed Leukocyte Cultures (MLCs)

MLCs were used to assess alloreactivity as a simple in vitro model of GVHD. Human PBMC were suspended in RPMI 1640 medium supplemented with 1% nonessential amino acids; 1% sodium pyruvate; 1% L-glutamine; and 10% heat-inactivated, pooled, normal human serum. One× $10^5$ responder cells and $1\times10^5$ irradiated (2,200 cGy) stimulator cells per well were co-cultured in triplicate in round-bottom 96-well plates for 6 days at 37° C. in a humidified 5% carbon dioxide/air atmosphere. MLCs were carried out either in unmodified medium or with the addition of AAT (at concentrations of 0.1 to 0.5 mg/ml) or albumin. All final culture volumes were 200 μl/well. Concanavalin A (Sigma-Aldrich Co. St. Louis, Mo.) was added (4 μg/well) on day 3 to responder cells plated without stimulator cells to provide a control for cell proliferation. On day 6, cultures were pulsed with 1 μCi of $^3$H-thymidine for 18 hours before harvesting; $^3$H-thymidine uptake was measured as the mean counts per minute (cpm) from the three replicates and harvested onto filter paper strips using a [beta]-scintillation counter (Packard BioScience Company, Meriden, Conn.). Results were expressed as stimulation index (SI)=(mean cpm of stimulated cells−mean cpm of nonstimulated cells: mean cpm of nonstimulated cells).

Markers of Inflammation

Supernatants from MLCs were collected and analyzed for cytokines and inflammatory markers with potential relevance to GVHD, including TNF-α, IL-6 and IL-8, as determined by enzyme-linked immunosorbent assays (ELISA). The probes used included human BAF210 TNF-α, BAF206 IL-6, BAF208 IL-8 (R&D Systems, Minneapolis, Minn.). When inflammatory marker concentrations were less than the assay detection limit, the sample was assigned the median value between 0 and the detection limit.

Analysis of Human and Murine Cytokines by Real-Time PCR

RNA was extracted by standard techniques. Applied Biosystems Pre-Designed Gene Expression Assays containing both primers and fluorescent Taq-Man probes were used to determine human or mouse gene expression. β-actin and GUSB were used as 'housekeeping' controls for normalization of quantitative RNA variation.

Human probes: IL-32, all isoforms (Hs00170403_m1), IL-32β and isoforms (Hs00997068_g1), IL-32α and (Hs00992439_g1), β-actin, (Hs00607939), GUSB (Hs03929099_m1), TNFα (Hs00174128_m1), IL-1β (Hs01555410_m1), PR3 (Hs01597752_m1), PAR2 (Hs00173741_m1).

Murine probes: TNFα (Mm00443258_m1), IL-1 (Mm01336189_m1), IL-1Ra (Mm01337566_m1) and PR$^3$ (Mm00478323_m1).

Each 20 μL reaction contained 2.0 γL 10×PCR$^β$ Buffer without Mg2+, 2.8 μL 25 mM MgCl2 (3.5 mM final concentration), 0.4 μl, ROX passive reference dye, 0.4 μL 10 mM dNTPs, 1.0 μl ABI primer/probe, and 0.16 μl (0.8 U) Fast Start Taq Polymerase (Roche, Indianapolis, Ind., USA), 8.24 μl H2O and 5 μl of the cDNA template. All reactions were carried out in triplicate in 384-well plates on an ABI7900HT (Applied Biosystems, Carlsbad, Calif.). For inclusion in the data set, standard deviations of the triplicates had to be less than 0.15 CT (cycle threshold). Additionally, we verified that the PCR efficiencies of the ABI assays were >95% and that the slopes of the linear portion of the amplification curves varied by less than 5%

Effect of AAT on GVHD Prevention in an MHC Matched, Minor Antigen Disparate Murine Transplant Model.

C57/BL6J mice (H-2$^b$) (Jackson Laboratory, Bar Harbor, Me.), 10-14 weeks old with average body weight of 28 g, received single-dose total body irradiation with 1000 cGy followed by intratail vein injection of T-cell-depleted bone marrow (BM, 5×10$^6$ cells), and CD8+ splenic lymphocytes (0.2×10$^6$ cells) from C3H.SW-H2$^b$/SnJ donors (H-2$^{bc}$) (Jackson Laboratory, Bar Harbor, Me.). BM was T-cell-depleted using the T Cell Isolation Kit II (Milteny Biotec, Auburn, Calif.). CD8+ T-cells were isolated from splenocytes by positive selection, using MACS CD8+ microbeads as directed by the manufacturer (Milteny Biotec, Auburn, Calif.).

Mice in the experimental group were given AAT intraperitoneally at 3 mg/dose, suspended in 125 μl, before irradiation and donor cell infusion, and every 2 days post-HCT for a total of 10 injections (see AAT treatment schedule). Mice in the control group were injected, also intraperitoneally, with 125 μl of human albumin on the same schedule. Each group consisted of 16 mice. GVHD was assessed by a standard scoring system. Body weights were obtained and recorded on day 0 and weekly thereafter. A weekly clinical index was generated by summation of 5 criteria scores: percentage of weight change, posture (hunching), activity, fur texture, and skin integrity (maximum score=10). Animals that received a score of 6.5 or higher were killed using CO2 euthanasia. Blood samples were collected sequentially for cytokine assays. To determine the presence of various cytokines in the two groups of mice, we used the mouse proteome profiler array membrane kit Panel A (ARY006; R&D Systems, Minneapolis, Minn.) according to the manufacturer's instructions. Equal volumes (100 μl) of plasma were collected from individual animals and added to the precoated membranes of the kit. The dot blot membranes (standardized for loading control) were analyzed using ImageQuant software (Molecular Dynamics, Sunnyvale, Calif.). The experiments were approved by the Institutional Animal Care and Use Committee (IACUC) of the FHCRC.

Chimerism Analysis

Chimerism analyses were done on mouse PBMC following separation of blood on FicollHypaque (density=1.074). $^{14}$ Cells at the interface were collected and washed in phosphate buffered saline by centrifugation. The contributions of recipient (C57/BL6J) and donor cells (C3H.SW-H2$^b$/SnJ) to peripheral blood were quantified by fluorescent variable number of tandem repeat (VNTR) PCR analysis, as described.

Histopathology

At autopsy skin, stomach and small bowel samples were obtained from AAT and albumin-treated mice, fixed in 4% paraformaldehyde, and embedded in paraffin before sectioning. The sections were stained with hematoxylin-eosin to assess for inflammatory lesions by light microscopy. The frequencies and severity of inflammatory lesions were estimated and compared between groups. At least 3 sections from each organ were scored.

Statistical Analysis

For gene expression purposes, all values were expressed as the mean±SEM. A Student t test was used to compare continuous variables between two groups; 1-way analysis of variance (ANOVA) was applied to compare continuous variables among three or more groups.

IL-32 expression in MLC. In one example, to determine a potential role of IL-32 in MLC reactivity, responder cells from MLC were processed for western blotting and RNA analysis (data not shown). IL-32 was upregulated both at the mRNA and protein levels in cells exposed to allogeneic stimulator cells in comparison to autologous controls. The supernatants of the same 7-day MLCs revealed high levels of TNF-, IL-6 and IL-8 (data not shown).

Figure 12A:
FIGS. 12A and 12B represent a histogram plot (A) of some affects of interleukin-32 (IL-32) and a control on cytokine expression and a Western blot (B) representative of affects of various concentrations of AAT on IL-32 (β and γ forms)
Figure 12B:
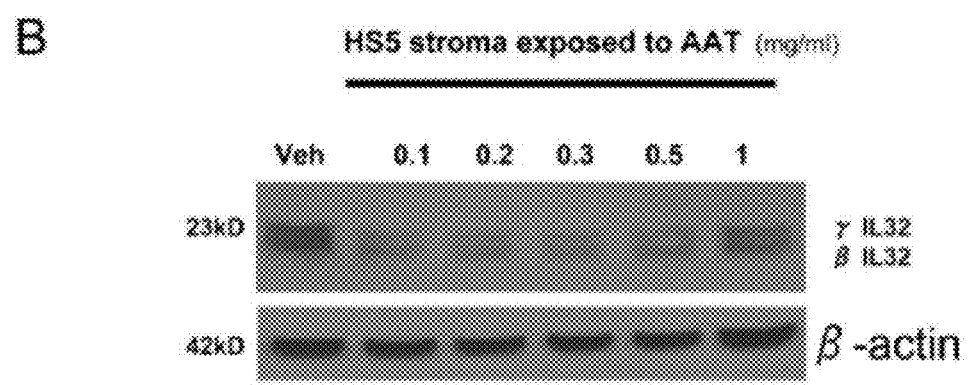

Repression of IL-32 by siRNA or addition of AAT broadly inhibits inflammatory mediators. To study the role of endogenous IL-32 in PBMC, IL-32-specific siRNA oligomeres were used, which target each of the IL-32 isoforms as confirmed by BLAST (basic local alignment search tool) alignment. As shown in FIG. 12A, down-regulation of IL-32 by siRNA resulted in a global reduction of cytokine levels in the supernatants, as illustrated by an array of 36 cytokines. The only cytokine that was up-regulated (by 56% and 60% in two biological duplicates) was 1-309, a chemokine secreted by regulatory T cells. To determine the impact of AAT on IL-32 protein levels human stroma cell line HS5 were used, which expresses and secretes IL-32 and can be grown in serum-free medium. As shown in FIG. 12B, the addition of AAT (at 0.1-1.0 mg/ml) resulted in reductions of endogenous IL-32β and γisoforms. The western blot is representative of three similar experiments.

Figures 13A, 13B:
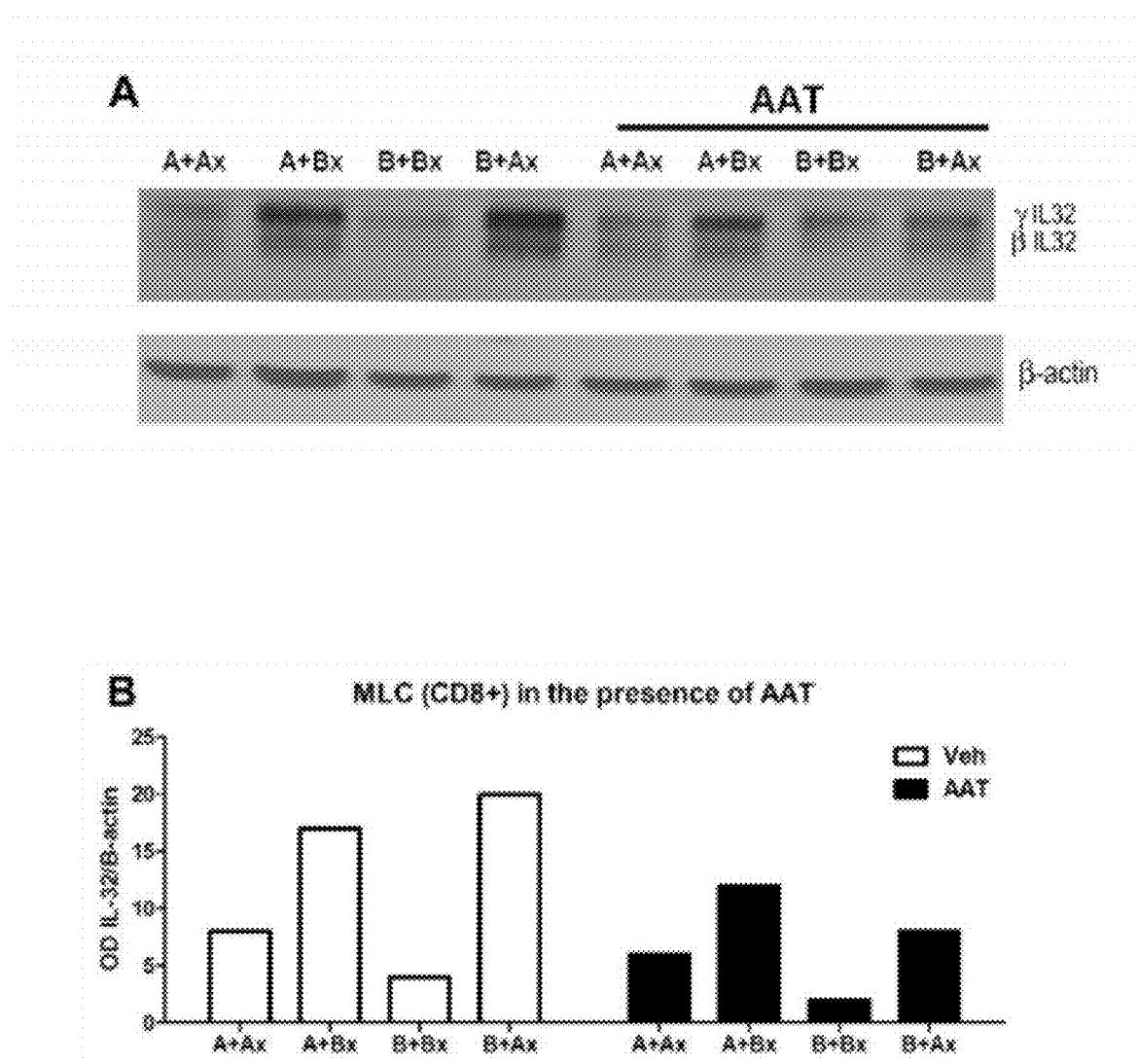
FIGS. 13A-13D represent a Western Blot (A) and histogram plots (B-D) of AAT affects on proliferation and TNF secretion of mixed lymphocyte cultures (MLCs)
Figure 13C:
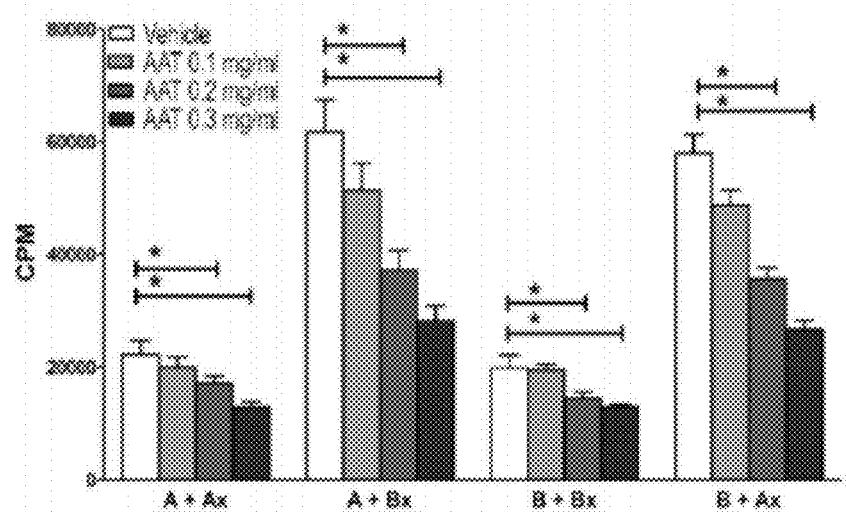
Figure 13D:
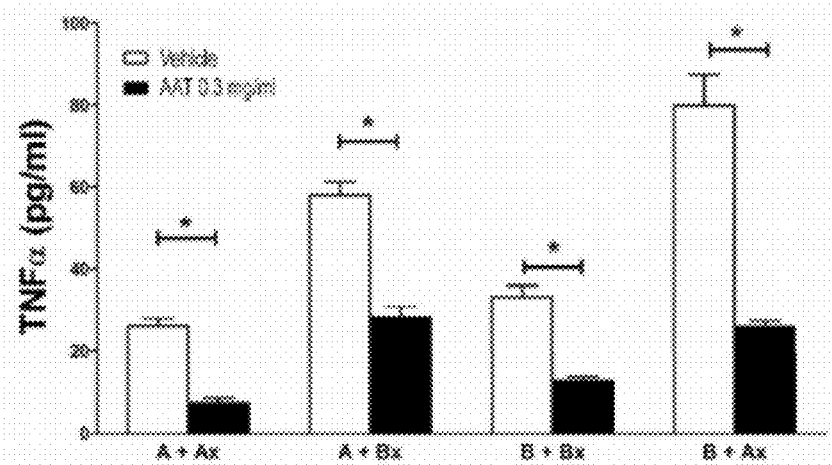

IL-32 and AAT effect on secreted cytokines in MLC. In another example, the MLCs to which AAT was added at concentrations ranging from 0.1 to 0.5 mg/ml were carried out. CD8+ cells sorted from MLCs showed levels of IL-32β and γisoforms at least 2-fold lower than in the absence of AAT (FIGS. 13A and 13B). Concurrently, there was significant dose-dependant suppression of the proliferative capacity as determined by $^3$H thymidine uptake (FIG. 13C), and a 2-fold reduction in TNFα levels (FIG. 13D). These data demonstrate that AAT had a profound effect on reducing alloreactivity in parallel with inhibition of IL-32 and TNFα production.

IL32 gene expression in blood cells of patients with clinical GVHD. Then IL32 was examined as a possible biomarker for GVHD by examining expression in WBC and PBMC from patients at various time intervals after HCT. Expression of IL32 in WBC was two-fold higher in patients with acute GVHD than in patients who did not show clinical evidence of GVHD (p<0.02; data not shown); IL32 expression levels in PBMC of patients with chronic GVHD, untreated (n=8) or treated with steroids, cyclosporine or both (n=14) did not differ from IL32 expression levels in PBMC of healthy controls (n=9) (p=0.74 and 0.50, respectively) (data not shown).

Figures 14A, 14B:
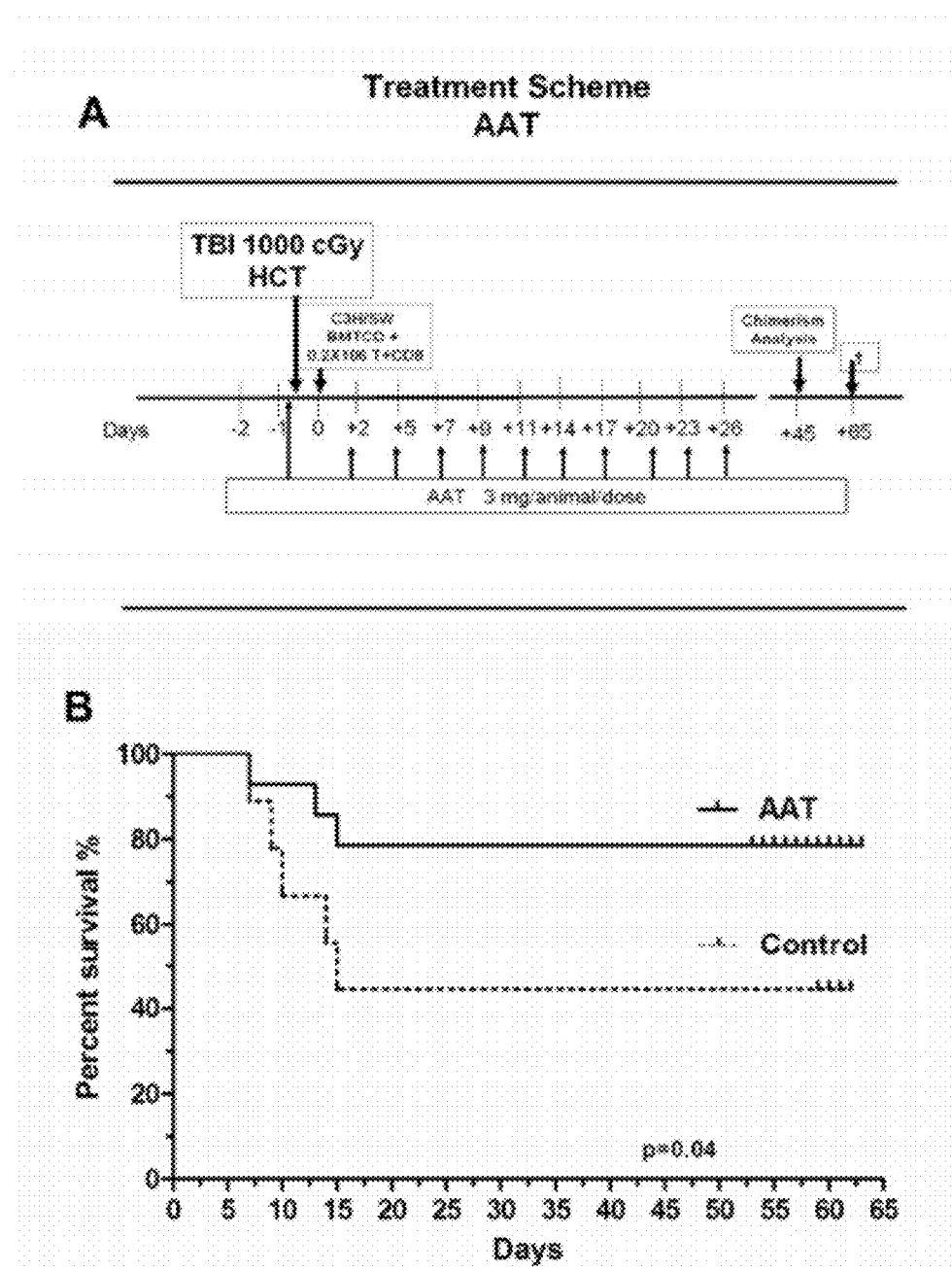
FIGS. 14A-14E represent effects of AAT on GvHD severity and mortality where (A) represents the aAT treatment regimen, (B) represents survival, (C) represents severity of GvHD, (D) represents change in body weight over time and (E) represents donor chimerism.
Figures 14C, 14D, 14E:
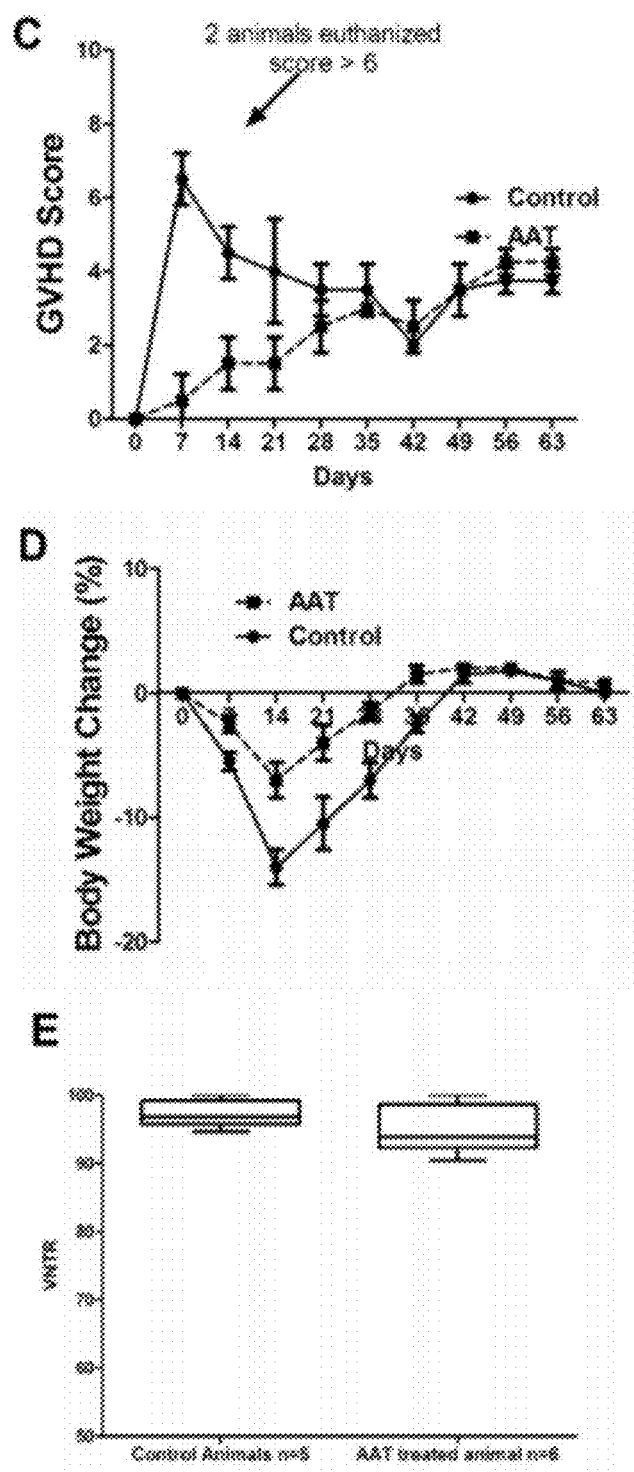

AAT abrogates GVHD and reduces mortality in an MHC matched, minor antigen disparate murine transplant model Lethally irradiated (1000 cGy) C57/BL6J (H-2$^b$) mice were injected iv with 5×10$^6$ T cell-depleted BM cells and 0.2×10$^6$ CD8+ splenic T cells from C3H.SW-H2$^b$/SnJ mice (H-2$^{bc}$). Recipient mice were given 3 mg of AAT (in 125 µl) on day −1 and again on day +2 and every 72 hours for a total of 10 injections (FIG. 14A). Albumin controls received the same volume of human serum albumin on the same schedule. As shown in FIG. 14B, by day 65 after transplantation survival was 80% in AAT-treated mice versus 40% in albumin treated controls (n=15; p=0.04, log rank). In both albumin controls and AAT-treated mice C3H.SW-H2$^b$/SnJ donor cells accounted for more than 95% of cells in peripheral blood (p=0.25) (FIG. 14C). It is contemplated herein that certain embodiments concern inhibiting IL-32 mRNA and/or expression in a subject in need thereof using compositions disclosed herein, for example, AAT.

Albumin controls experienced significantly greater weight loss and showed higher GVHD scores than AAT treated mice (FIGS. 14D and 14E). Two AAT-treated mice that developed signs of gut-GVHD by day 45, i.e. after discontinuation of AAT, showed complete resolution of GVHD upon re-institution of AAT therapy, given every 72 hours, for 4-5 doses.

Histologic examination of albumin-treated mice showed patchy epithelial damage in the hair follicles and edema (data not shown). The forestomach and duodenum showed patchy lymphocytic infiltration of epithelium and damage to the glands as evidenced by exocytosis and apoptosis (data not shown). Mice treated with AAT, in contrast, had normal skin and only rare areas of infiltration in stomach and duodenum (data not shown). These results indicate that AAT significantly attenuated clinical and histologic manifestations of GVHD and reduced GVHD related morbidity and mortality.

Figures 15A, 15B:
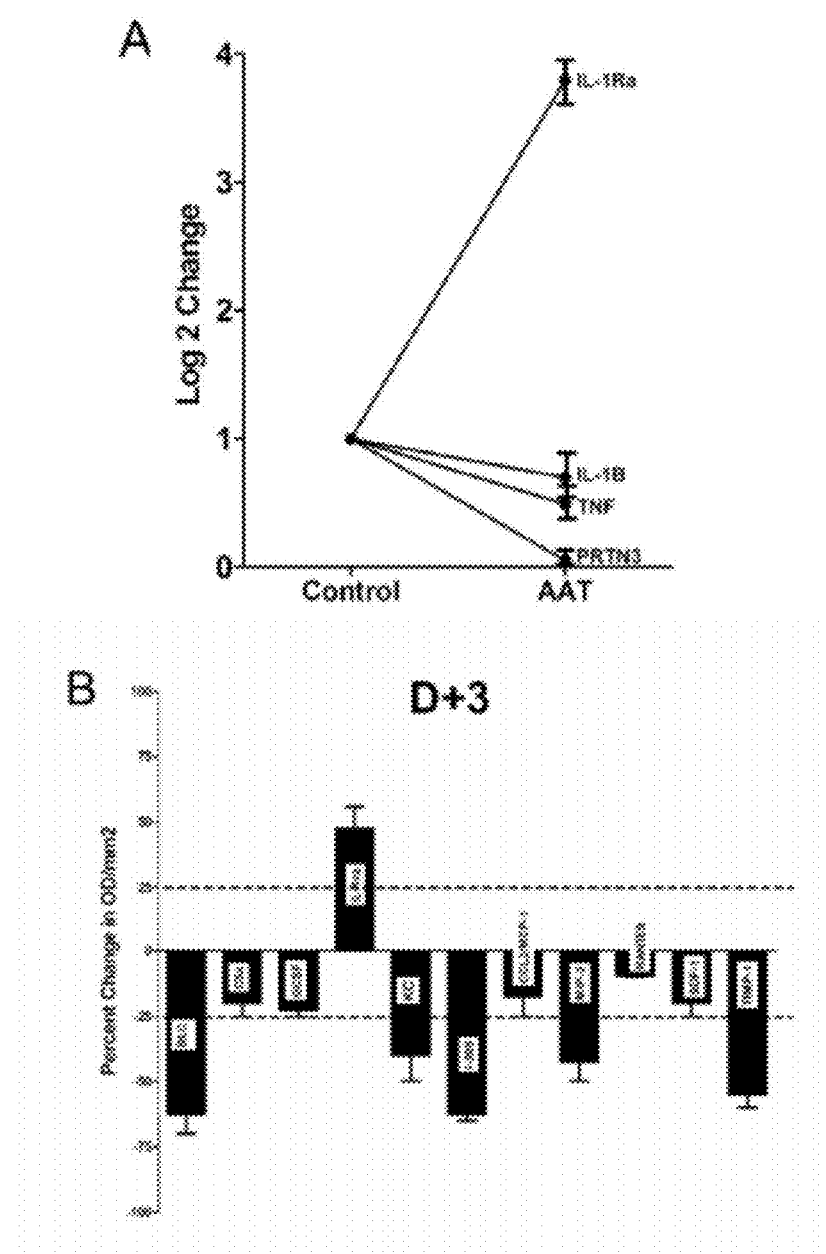
FIGS. 15A-15D represent effect of AAT on cytokine RNA and protein expression after BMT. A) represents various cytokine plots and B) C) and D) represent cytokine plasma levels at days 3, 7 and 10 after BMT.
Figures 15C, 15D:
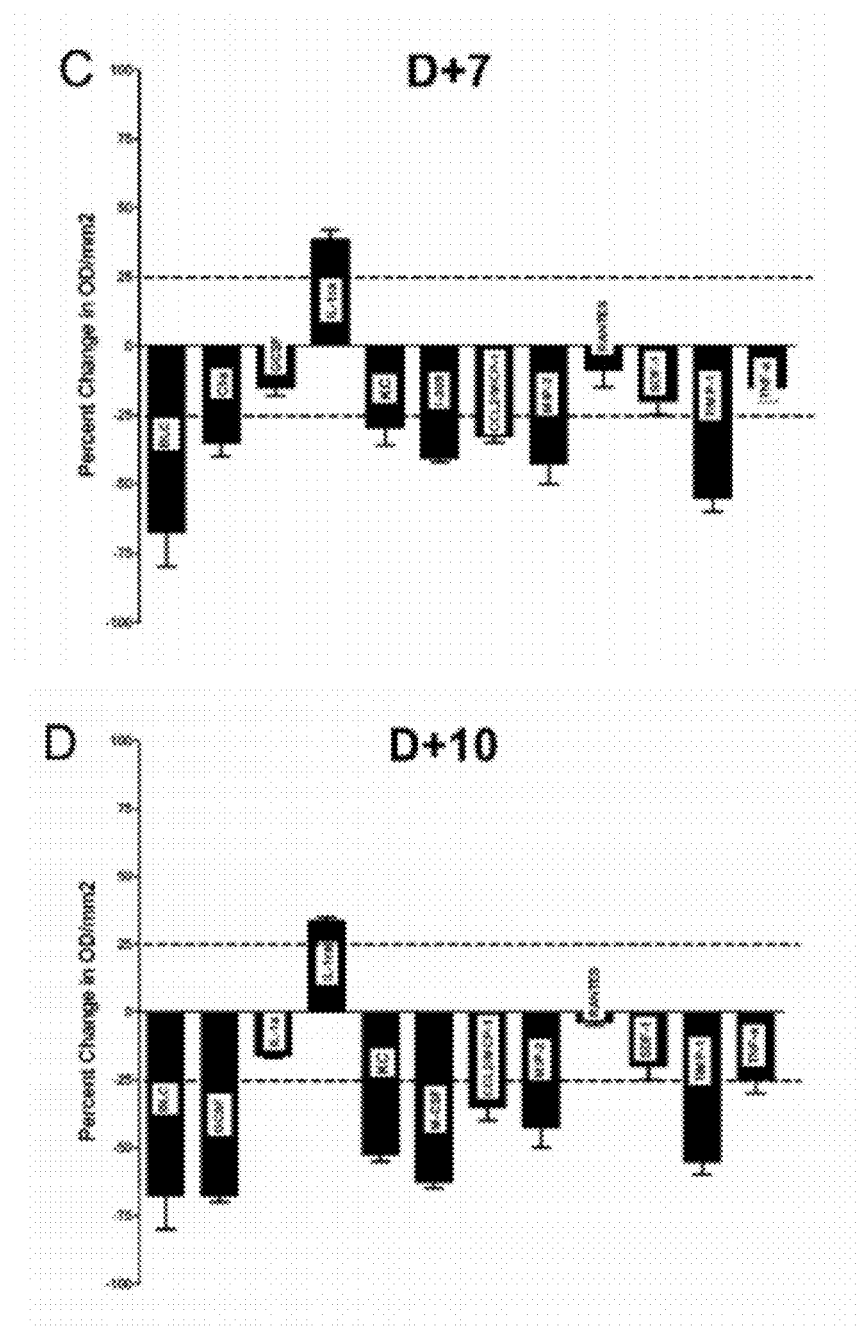

AAT suppresses pro-inflammatory signals and upregulates IL-1Rα in MHC matched, minor antigen disparate murine transplant recipients. Steady-state levels of IL-1β, TNF-α, and PR3 mRNA on day 21 was significantly lower in AAT treated compared to albumin-treated animals (FIG. 15A). Moreover, in a panel of 40 cytokines as illustrated in FIG. 7B-D, there was a global suppression of cytokine levels except for IL1Ra in the plasma of AAT-treated mice. Also suppressed were, among others, factors such as CXCL13/BLC/BCA-1, a B cell-attracting chemokine 1(BCA-1), and CXCL2/MIP-2, known as macrophage inflammatory protein 2α-(MIP2-), a chemokine chemotactic for polymorphonuclear leukocytes.

It was demonstrated that a correlation of IL-32 expression with responses in MLC and with the manifestations of acute GVHD exists. Although IL-32 is produced locally, the cytokine was readily detected in the systemic circulation, and IL32 mRNA concentrations in PBMC discriminated between patients with and without acute GVHD. This observation raised the possibility that inhibition of IL-32 activation would interfere with alloactivation and possibly prevent or attenuate the development and manifestations of GVHD. The present data show that AAT strongly suppressed CD8+ cell proliferation in allogeneic MLCs, and inhibition of proliferation was associated with suppression of IL-32, as well as other pro-inflammatory proteins, such as TNFα, IL-8 and IL-6.

Alternatively, the benefit of AAT in that setting may be related to inhibition of IL-32 activation in other tissues, e.g. epithelial cells. The efficacy of AAT in GVHD prevention or treatment is consistent with observations of the immunosuppressive or immunomodulatory effect of AAT in other models. In tune with those findings, over-expression of AAT by gene delivery using recombinant adeno-associated virus significantly reduced insulinitis and prevented the development of overt hyperglycemia in NOD mice.

Administration of AAT profoundly affected expression of IL-32. The lack of inhibition of IL-1Ra in the context of GVHD prevention is consistent with previous reports that IL-1Ra inhibited mouse islet allograft rejection and elevated IL-1Ra levels in long-lasting islet allografts explanted from AAT treated animals. Thus, compositions disclosed herein can be combined with other known compositions in order to potentially achieve even better inhibition of GvHD and prolonged graft survival.

FIGS. 12A and 12B.—Effect of IL-32 specific siRNA and AAT on expression of inflammatory mediators. A.) Change in cytokines expression in PBMC transfected with IL-32-specific or scrambled siRNA (control). Cytokine expression was assayed using profiler cytokine array (R&D Systems). Cytokine concentrations from siRNA transfected PBMC supernatant are expressed as percent change in comparison to control supernatants. Shown are changes (mean±SEM) in 29 cytokines. The horizontal line indicates a decrease of 25% in comparison to controls transfected with scrambled sequence. Levels were determined after 72 hours of culture. The membrane contained probes for C5a, ICAM-1, IL-4, IL-13, IL-32α, MIP-1β, CD40 ligand, IFN-γ, IL-5, IL-16, IP-10, RANTES, G-CSF, IL-1α, IL-6, IL-17, I-TAC, SDF-1, GM-CSF, IL-1, IL-8, IL-17E, MCP-1, Serpin-E1, GROα, IL-1ra, IL-10, IL-23, MIF, TNFα, I-309, IL-2, IL-12p70, IL-27 MIP-1α, and TREM-1. B) Western blot of protein extract of the human stroma cell line HS5 exposed to vehicle only (veh) or various concentrations of AAT (in serum-free medium). Shown are levels of IL-32β and γ isoforms at concentrations of ATT between 0.1 and 1 mg/ml.

FIGS. 13A-13D Inhibition of proliferation and TNF secretion in MLC by AAT. (A) Western blot of IL-32β and levels in CD8+ cells from 7-day MLCs under control conditions and in the presence of AAT (0.3 mg/ml). IL-32 and isoforms in the presence of AAT. The western blot is representative of 3 similar experiments. (B) Expression changes in IL-32 protein levels in allogeneic MLCs and autologous controls as determined by densitometry (OD) of the same biological experiment. Open columns reflect results in the absence of AAT; solid columns in the presence of AAT. (C) Proliferation in MLC (as measured by $^3$H thymidine uptake; CPM, mean±SEM). (D) TNF-ELISA. Secretion of TNF in the presence and absence of AAT. * indicates p<0.05 (Student t test).

FIGS. 14A-14E. Effect of AAT on GVHD severity and mortality. (A) AAT treatment scheme (see also text). (B) Survival. Survival of AAT-treated mice versus albumin-treated controls (n=15 each group, p=0.04). (C) Severity of GVHD. GVHD was scored based on percentage of weight loss, skin integrity, posture, mobility, and fur texture. Clinical signs were graded on a scale of 0 to 2, where 0 was absent, 1 was moderate, and 2 was severe, and the individual scores were added up. Shown are GVHD clinical scores for 30 days after transplantation (mean±SEM per time point) (D) Change in body weight of transplanted mice over time post-transplant (mean±SEM; n=15). (E) Donor chimerism. Proportion of donor cells among PBMC in AAT-treated (n=6) versus albumin-treated (n=5) mice at day 45 (p=0.25).

FIGS. 15A-15D. Effect of AAT on cytokine RNA and protein expression in PBMC and plasma after transplantation. (A) IL-1Ra, IL-1β, TNF-α, and PR3 RNA levels, determined by RT-PCR, in PBMC. Levels in AAT-treated mice (n=6) are expressed relative to levels in albumin treated controls; mean±SEM (n=6) (log 2). (B, C and D) Mean±SEM cytokine plasma levels at 3, 7 and 10 days after transplantation. Shown is a panel selected from a mouse array of 40 cytokines, showing significant changes. Changes in cytokine concentration are expressed as percent change compared to albumin control. The horizontal dotted line indicates an increase/decrease of 25%.

All of the COMPOSITIONS and METHODS disclosed and claimed herein may be made and executed without undue experimentation in light of the present disclosure. While the COMPOSITIONS and METHODS have been described in terms of preferred embodiments, it will be apparent to those of skill in the art that variation may be applied to the COMPOSITIONS and METHODS and in the steps or in the sequence of steps of the METHODS described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed:

1. A method for treating acute graft versus host disease (GvHD) in a human subject in need thereof, said method comprising administering to the human subject a composition comprising alpha 1-antitrypsin (AAT) and treating GvHD in the human subject.

2. The method of claim 1, wherein the composition further comprises one or more anti-inflammatory agents.

3. The method of claim 1, wherein the AAT is full-length and is part of a fusion polypeptide.

4. The method of claim 3, wherein the fusion polypeptide comprises the full-length AAT fused to an immunoglobulin constant region.

5. The method of claim 1, wherein the human subject has undergone allogeneic bone marrow implantation.

* * * * *

UNITED STATES PATENT AND TRADEMARK OFFICE
CERTIFICATE OF CORRECTION

PATENT NO. : 9,457,070 B2
APPLICATION NO. : 13/209349
DATED : October 4, 2016
INVENTOR(S) : Dinarello et al.

It is certified that error appears in the above-identified patent and that said Letters Patent is hereby corrected as shown below:

On the Title Page

On Page 2, in item (56), under "OTHER PUBLICATIONS", in Column 1, Line 2, delete "adena-associated virus serotype 2 alpha1" and insert -- adeno-associated virus serotype 2 alpha 1 --

On Page 2, in item (56), under "OTHER PUBLICATIONS", in Column 1, Line 6, delete "adena-associated virus 1" and insert -- adeno-associated virus alpha 1 --

On Page 2, in item (56), under "OTHER PUBLICATIONS", in Column 1, Line 11, delete "A-1" and insert -- α-1 --

On Page 2, in item (56), under "OTHER PUBLICATIONS", in Column 1, Lines 25-26, delete "Fo the Initial Treatment of Acute Graft-Versus-Disease;" and insert -- For the Initial Treatment of Acute Graft-versus-Host Disease; --

On Page 2, in item (56), under "OTHER PUBLICATIONS", in Column 1, Lines 33-34, delete "dana-farber.org/Research/Chnical-" and insert -- dana-farber.org/Research/Clinical- --

On Page 2, in item (56), under "OTHER PUBLICATIONS", in Column 2, Line 7, delete "Hill et al (JCI, 1999, 104:459-467).".

On Page 2, in item (56), under "OTHER PUBLICATIONS", in Column 2, Line 23, delete "5126-5126," and insert -- 5126-5129, --

On Page 2, in item (56), under "OTHER PUBLICATIONS", in Column 2, Line 44, delete "1004-1004." and insert -- 1000-1004. --

Signed and Sealed this
Twenty-second Day of August, 2017

Joseph Matal
*Performing the Functions and Duties of the
Under Secretary of Commerce for Intellectual Property and
Director of the United States Patent and Trademark Office*

CERTIFICATE OF CORRECTION (continued)
U.S. Pat. No. 9,457,070 B2

In the Specification

In Column 1, Line 65, delete "(α1-" and insert -- α1- --

In Column 2, Line 3, delete "ATT" and insert -- AAT --

In Column 2, Line 14, delete "ATT" and insert -- AAT --

In Column 2, Line 25, delete "Talectris/Grifols" and insert -- Talecris/Grifols --

In Column 2, Line 30, delete "therapy/delivery" and insert -- therapy/delivery) --

In Column 3, Line 27, delete ""host" disease" and insert -- host disease" --

In Column 4, Line 20, delete "breadth," and insert -- breath, --

In Column 4, Line 21, delete "breach," and insert -- breath, --

In Column 5, Line 54, delete "embodiments" and insert -- embodiments, --

In Column 6, Line 4, delete "immunsuppressives" and insert -- immunosuppressives --

In Column 7, Line 51, delete "FIGS. 1A-1D illustrates" and insert -- FIGS. 1A-1D illustrate --

In Column 8, Line 7, delete "FIGS. 2A-2D illustrates" and insert -- FIGS. 2A-2D illustrate --

In Column 8, Line 14, delete "FIGS. 3A-3C illustrates" and insert -- FIGS. 3A-3C illustrate --

In Column 8, Line 21, delete "Hematoxilyn" and insert -- Hematoxylin --

In Column 8, Line 26, delete "FIGS. 4A-4H illustrates" and insert -- FIGS. 4A-4H illustrate --

In Column 8, Line 34, delete "FIGS. 5A-5D illustrates" and insert -- FIGS. 5A-5D illustrate --

In Column 8, Line 46, delete "FIGS. 6A-6D illustrates" and insert -- FIGS. 6A-6D illustrate --

In Column 8, Line 55, delete "FIGS. 7A-7E illustrates" and insert -- FIGS. 7A-7E illustrate --

In Column 9, Line 7, delete "FIGS. 8A-8D illustrates" and insert -- FIGS. 8A-8D illustrate --

In Column 9, Line 9, delete "(8B)" and insert -- (8B), --

In Column 9, Line 10, delete "FIGS. 9A-9C represents" and insert -- FIGS. 9A-9C represent --
In Column 9, Line 19, delete "subject" and insert -- subject. --

In Column 9, Line 21, delete "P=0.037" and insert -- P=0.037. --

In Column 9, Line 32, delete "forms)" and insert -- forms). --

In Column 9, Line 35, delete "(MLCs)" and insert -- (MLCs). --

In Column 9, Line 37, delete "aAT" and insert -- AAT --

In Column 9, Line 43, delete "B) C)" and insert -- B), C) --

In Column 10, Line 11, delete "limiting" and insert -- limiting. --

In Column 10, Line 65, delete "breadth," and insert -- breath, --

In Column 10, Line 67, delete "breach," and insert -- breath, --

In Column 13, Line 36, delete "ATT" and insert -- AAT --

In Column 14, Line 2, delete "Gly;" and insert -- Gly, --

In Column 14, Line 11, delete "(SEQ" and insert -- (SEQ. --

In Column 14, Line 18, delete "ID)" and insert -- ID --

In Column 14, Line 31, delete "include but are not limited to" and insert -- include, but are not limited to, --

In Column 14, Line 34, delete "20)" and insert -- 20); --

In Column 14, Line 35, delete "22)" and insert -- 22); --

In Column 14, Line 39, delete "ID)" and insert -- ID --

In Column 14, Line 50, delete "ED" and insert -- ID --

In Column 14, Line 59, delete "Accordance" and insert -- accordance --

In Column 15, Line 12, delete "regima" and insert -- regimen --

In Column 15, Line 48, delete "cant" and insert -- can't --

In Column 18, Line 59, delete "-Prolinamide;" and insert -- -L-Prolinamide; --

CERTIFICATE OF CORRECTION (continued)
U.S. Pat. No. 9,457,070 B2

In Column 19, Line 13, delete "therewith," and insert -- therewith. --

In Column 19, Lines 24-25, delete "-prolinamide benzyloxycarbonyl)-" and insert -- -L-prolinamide; (benzyloxycarbonyl)- --

In Column 19, Line 43, delete "ID" and insert -- ID NO. --

In Column 24, Lines 33-34, delete "include but are not limited to" and insert -- include, but are not limited to, --

In Column 24, Line 41, delete "quinolonses," and insert -- quinolones, --

In Column 24, Lines 48-49, delete "gancyclovir," and insert -- ganciclovir, --

In Column 24, Line 49, delete "valacylocir," and insert -- valacyclovir, --

In Column 24, Line 50, delete "edoxudine" and insert -- edoxudine. --

In Column 24, Line 61, delete "pirethrins/piperonyl" and insert -- pyrethrins/piperonyl --

In Column 25, Line 9, delete "immunsuppressives," and insert -- immunosuppressives, --

In Column 25, Line 66, delete "FIG. 1A-1D." and insert -- FIGS. 1A-1D. --

In Column 26, Line 55, delete "FIG. 2A-2D illustrates" and insert -- FIGS. 2A-2D illustrate --

In Column 27, Line 42, delete "FIG. 3A-3C illustrates" and insert -- FIGS. 3A-3C illustrate --

In Column 27, Line 55, delete "Hematoxilyn" and insert -- Hematoxylin --

In Column 28, Line 7, delete "Hematoxilin" and insert -- Hematoxylin --

In Column 28, Line 22, delete "FIG. 4A-4H illustrates" and insert -- FIGS. 4A-4H illustrate --

In Column 29, Line 3, delete "IL-IL-1β/IFNγ" and insert -- IL-1β/IFNγ --

In Column 29, Line 29, delete "FIG. 5A-5D illustrates" and insert -- FIGS. 5A-5D illustrate --

In Column 30, Line 17, delete "FIG. 6A-6D illustrates" and insert -- FIGS. 6A-6D illustrate --

In Column 30, Line 46, delete "FIG. 7A-7E illustrates" and insert -- FIGS. 7A-7E illustrate --
In Column 31, Line 35, delete "FIG. 8A-8D illustrates" and insert -- FIGS. 8A-8D illustrate --

In Column 31, Line 37, delete "(8B)" and insert -- (8B), --

In Column 31, Line 52, delete "1986)." and insert -- 1986. --

In Column 33, Line 67, delete "(2001)." and insert -- (2001)). --

In Column 36, Line 18, delete "TNFαα" and insert -- TNFα --

In Column 37, Line 56, delete "survival" and insert -- survival. --

In Column 41, Line 2, delete "9" and insert -- 9. --

In Column 41, Line 28, delete "cells" and insert -- cells. --

In Column 41, Line 36, delete "+28. ratio" and insert -- +28 ratio --

In Column 41, Line 39, delete "P=0.037" and insert -- P=0.037. --

In Column 41, Line 43, delete "P=0.0127" and insert -- P=0.0127. --

In Column 42, Line 33, delete "Ficoll-Hypaque" and insert -- Ficoll-Paque --

In Column 42, Line 40, delete "policlonal" and insert -- polyclonal --

In Column 42, Line 46, delete "cathespin" and insert -- cathepsin --

In Column 43, Line 67, delete "5%" and insert -- 5%. --

In Column 44, Line 10, delete "(Milteny" and insert -- (Miltenyi --

In Column 44, Line 13, delete "(Milteny" and insert -- (Miltenyi --

In Column 44, Line 43, delete "FicollHypaque" and insert -- Ficoll-Paque --

In Column 45, Line 8, delete "oligomeres" and insert -- oligomers --

In Column 45, Line 28, delete "13 B)." and insert -- 13B). --

In Column 46, Line 22, delete "FIG. 7B-D," and insert -- FIGS. 7B-D, --

In Column 46, Line 27, delete "2α-(MIP2-)," and insert -- 2α-(MIP-2), --
In Column 46, Line 50, delete "insulinitis" and insert -- insulitis --

In Column 46, Line 62, delete "A.)" and insert -- (A) --

CERTIFICATE OF CORRECTION (continued)
U.S. Pat. No. 9,457,070 B2

In Column 47, Line 14, delete "ATT" and insert -- AAT --

In Column 47, Line 15, delete "13A-13D" and insert -- 13A-13D. --

In Column 48, Line 3, delete "point)" and insert -- point). --

In the Claims

In Column 73, Line 2, in Claim 1, delete "acute graft" and insert -- graft --